(12) United States Patent
Rogers et al.

(10) Patent No.: US 6,335,020 B1
(45) Date of Patent: Jan. 1, 2002

(54) ALLERGENIC PEPTIDES FROM RAGWEED POLLEN

(75) Inventors: Bruce Rogers, Cambridge, MA (US); David G. Klapper, Chapel Hill, NC (US); Thorunn Rafnar, Baltimore, MD (US); Mei-chang Kuo, Winchester, MA (US)

(73) Assignee: Immulogic Pharmaceutical Corp., Waltham, MA (US)

( * ) Notice: Subject to any disclaimer, the term of this patent is extended or adjusted under 35 U.S.C. 154(b) by 0 days.

(21) Appl. No.: 08/464,000

(22) Filed: Jun. 5, 1995

Related U.S. Application Data

(63) Continuation of application No. 08/290,448, filed on Aug. 15, 1994, now Pat. No. 5,698,204, which is a continuation of application No. 07/529,951, filed on May 29, 1990, now abandoned, which is a continuation-in-part of application No. 07/325,365, filed on Mar. 17, 1989, now abandoned.

(51) Int. Cl.[7] ............................................. A61K 39/35
(52) U.S. Cl. ..................... 424/275.1; 530/350; 530/370; 530/379; 435/69.3
(58) Field of Search ........................... 424/275.1, 278.1, 424/69.3; 530/370, 379, 350; 435/69.3

(56) References Cited

U.S. PATENT DOCUMENTS 4,338,297 A  7/1982  Michael et al. ............... 424/91

OTHER PUBLICATIONS

Goodfriend, L. et al. (1985) "RA–5G A Homologue of RA–5 in Giant Ragweed Ambrosia–trifida pollen isolation Hla–dr–associated activity and amino–acid sequence" Molecular Immunology 22(8):899–906.
Ishizeka, K.et al. (1975) *J. of Immunology* 114(1):110–115.
King, T.P. and P.S. Norman (1962) *Biochemistry* 1(4):709–720.
King, T.P. et al. (1964) Isolation and characterization of allergens from ragweed pollen. II. *Biochemistry* 3(3):458–468.
King, T.P. et al. (1981) "Limited Proteolysis of Antigens E and K from Ragweed Pollen" *Arch. Biochem. Biophy* 212(1):127–135.
King, T.P. et al. (1974) "Chemical modification of the major allergen of ragweed pollen, antigen E. Immunochemistry" Immunochemistry 11:83–92.
King et al. (1981) "Limited Proteolysis of Antigens E and K from Ragweed Pollen" *Archives of Biochemistry and Biphysics*, 212(1):127–135.
King T. P. (1972) "Separation of Proteins by Ammonium Sulfate Gradient Solubilization" *Biochemistry* 11(3):367–371.
Lamb et al. (1983) "Induction of Tolerance in Influenza Virus–Immune T Lymphocyte Clones with Synthetic Peptides of Influenza Hemagglutinin" *J. Exp. med.* 157:1434–1447.
Lerner, R.A. (1982) "Tapping the immunological repertoire to produce antibodies of predetermined specificity" *Nature* 299:592–596.
Litwin, A. et al. (1988) International Archives of Applied Immunology, 87:361–366.
Litwin et al. (1991) "Regulation of the Human Immune Response to Ragweed Pollen by Immunotherapy. A Controlled Trial Comparing the Effect of Immunosuppressive Peptic Fragments of Short Ragweed with Strandard Treatment" *Clinical and Experimental Allergy* 21:457–465.
Lowenstein, H. et al. (1981) "Antigens of ambrosia–elatior short ragweed pollen 2. immunochemical identification of known antigens by quantitative immuno electrochemical identification of known antigens by quantitative immuno-electrophoresis" *Immunology* 127(2):637–642.
Marsh, D.G. et al. (1987) "Immune Responsiveness to ambrosia–Artemisiifolia short ragweed pollen allergen AMB–A–VI RA6 is associated with HLA–DR5 in allergic Humans" *Immunogenetics* 26:230–236.
Marsh et al. (1986) "Allergen Nonmenclature" *Terminology, Terminologie* 64(5):767–770.
Marsh et al. (1988) "Allergen nomenclature" *Allergy* 43:161–168.
Michael et al. (1990) "Modulation of the Immune Response to Ragweed Allergens by Peptic Fragments" *Clinical Experimental Allergy* 20:669–674.
Muckerheide, A. et al. (1980) Cellular Immunology 50:340–347.
Olson, J.R. and D.G. Klapper (1986) "Two Major Human Allrgenic Sites on Ragweed Pollen Allergen Antigen E Identified By Using Monoclonal Antibodies" *J. of Immunology* 136(6):2109–2115.
Olson et al. (1986) "Two Major Human Allergenic sites on ragweed Pollen Allergen Antigen E Identified By Using Monoclonal Antibodies" *J. of Immunol.* 136(6)2109–2115.
Paull et al. (1979) "Structure and activity of ragweed antigen E" *The Journal of Allergy and Clinical Immunology* 64(6)(1):539–545.
Scherer, M.T., et al. (1989) Cold Spring Harbor Symposia on Quantitative Biology vol. LIV, Cold Spring Harbor Laboratory Press, pp. 497–504.
Smith, J.J. et al. (1988) Molecular Immunology 25(4):355–365.
Takatsu et al. (1975) "Immunogenic Properties of Modified Antigen E" *Journal of Immunology* 115(6):1469–1476.
Young et al. (1983) "Efficient isolation of genes by using antibody probes" *Proc. Natl. Acad. Sci. USA* 80:1194–1198.

*Primary Examiner*—Laurie Scheiner
(74) *Attorney, Agent, or Firm*—Lahive & Cockfield, LLP

(57) ABSTRACT

Antigen E or *Amb a* I of ragweed pollen has been shown to be a family or families of proteins. cDNAs encoding *Amb a* I, the major human allergen of ragweed and *Amb a* II, peptides derived from *Amb a* I or *Amb a* II, antibodies against the peptides; and methods of treating individuals for sensitivity to ragweed are disclosed.

15 Claims, 36 Drawing Sheets

DE UNC CLONE 1

```
          10        20        30        40        50        60
           |         |         |         |         |         |
GAATTCGGCTGGAGAACGAATAAAGACGTGCTTGAAAATGGTGCTATTTTTGTTGCATCC
  E  F  G  W  R  T  N  K  D  V  L  E  N  G  A  I  F  V  A  S 70        80        90       100       110       120
           |         |         |         |         |         |
GGGGTCGATCCAGTGCTAACCCCTGAGCAAAGCGCAGGGATGATTCCAGCCGAACCAGGA
  G  V  D  P  V  L  T  P  E  Q  S  A  G  M  I  P  A  E  P  G 130       140       150       160       170       180
           |         |         |         |         |         |
GAGTCCGCTCTAAGCCTCACTAGTAGTGCTGGTGTACTCTCATGCCAACCCGGAGCACCT
  E  S  A  L  S  L  T  S  S  A  G  V  L  S  C  Q  P  G  A  P 190       200       210       220       230       240
           |         |         |         |         |         |
TGCTAAGCACCCGACCAATTACTAAGCACTTATAATGATCATTAATACTTTTTTTTATTT
  C  -  A  P  D  Q  L  L  S  T  Y  N  D  H  -  Y  F  F  L  F 250       260       270       280       290       300
           |         |         |         |         |         |
TATTTTTGATATTTTATATGTACTAAGGTAATGGAAATGAACCTTTACCTTCTAGTACTC
  Y  F  -  Y  F  I  C  T  K  V  M  E  M  N  L  Y  L  L  V  L 310       320
           |         |
TAAAAAAAAAAAAAAACCGAATTC
  -  K  K  K  K  P  N
```

Fig. 2

```
*******************************************
*  TRANSLATION OF A NUCLEIC ACID SEQUENCE  *
*******************************************
Done on DNA sequence AMB_A_IB_K.

DE   SEQUENCE OF AMB A IB CLONE.

Total number of bases is: 1328.
Analysis done on the complete sequence.
Done on (absolute) phase(s): 1.
Using the Universal genetic code.
```

```
         10        20        30        40        50        60
          |         |         |         |         |         |
TACATCTTGTATTTTACCTTAGCCCTTGTCACTTTGCTGCAACCTGTTCGTTCTGCAGAA
   Y  I  L  Y  F  T  L  A  L  V  T  L  L  Q  P  V  R  S  A  E 70        80        90       100       110       120
          |         |         |         |         |         |
GATGTTGAAGAATTCTTACCTTCAGCTAACGAAACAAGGAGGAGCCTGAAAGCATGTGAA
  D  V  E  E  F  L  P  S  A  N  E  T  R  R  S  L  K  A  C  E 130       140       150       160       170       180
          |         |         |         |         |         |
GCACACAACATTATAGACAAGTGCTGGAGGTGCAAAGCCGATTGGGCGAATAACCGACAA
  A  H  N  I  I  D  K  C  W  R  C  K  A  D  W  A  N  N  R  Q 190       200       210       220       230       240
          |         |         |         |         |         |
GCGTTAGCCGATTGTGCCCAAGGTTTTGCAAAGGGAACCTACGGTGGAAAACATGGTGAT
  A  L  A  D  C  A  Q  G  F  A  K  G  T  Y  G  G  K  H  G  D 250       260       270       280       290       300
          |         |         |         |         |         |
GTCTACACGGTCACCAGTGATAAAGATGATGATGTTGCAAATCCAAAAGAAGGCACACTC
  V  Y  T  V  T  S  D  K  D  D  D  V  A  N  P  K  E  G  T  L 310       320       330       340       350       360
          |         |         |         |         |         |
CGGTTTGCTGCTGCCCAAAACAGGCCCTTGTGGATCATTTTTAAAAGAAATATGGTGATT
  R  F  A  A  A  Q  N  R  P  L  W  I  I  F  K  R  N  M  V  I 370       380       390       400       410       420
          |         |         |         |         |         |
CATTTGAATCAAGAGCTTGTCGTAAACAGCGACAAGACCATCGATGGCCGAGGGGTGAAA
  H  L  N  Q  E  L  V  V  N  S  D  K  T  I  D  G  R  G  V  K
```

Fig. 3

```
        430         440         450         460         470         480
         |           |           |           |           |           |
GTTAACATCGTTAACGCCGGTCTCACCCTCATGAATGTCAAGAATATAATCATTCATAAC
 V  N  I  V  N  A  G  L  T  L  M  N  V  K  N  I  I  H  N 490         500         510         520         530         540
         |           |           |           |           |           |
ATAAATATCCATGATATTAAAGTTTGTCCAGGAGGCATGATTAAGTCCAACGATGGTCCA
 I  N  I  H  D  I  K  V  C  P  G  G  M  I  K  S  N  D  P 550         560         570         580         590         600
         |           |           |           |           |           |
CCAATTTTAAGACAACAAAGTGATGGTGATGCTATAAATGTTGCTGGTAGTTCACAAATA
 P  I  L  R  Q  Q  S  D  G  D  A  I  N  V  A  G  S  S  Q  I 610         620         630         640         650         660
         |           |           |           |           |           |
TGGATCGACCATTGCTCGCTCAGTAAGGCTTCCGATGGGCTGCTCGATATCACCCTCGGC
 W  I  D  H  C  S  L  S  K  A  S  D  G  L  L  D  I  T  L  G 670         680         690         700         710         720
         |           |           |           |           |           |
AGCTCACACGTGACCGTTTCCAACTGCAAATTCACCCAACACCAATTTGTATTATTGCTC
 S  S  H  V  T  V  S  N  C  K  F  T  Q  H  Q  F  V  L  L  L 730         740         750         760         770         780
         |           |           |           |           |           |
GGGGCTGATGACACCCATTATCAAGATAAAGGCATGCTAGCAACGGTAGCATTCAACATG
 G  A  D  D  T  H  Y  Q  D  K  G  M  L  A  T  V  A  F  N  M 790         800         810         820         830         840
         |           |           |           |           |           |
TTCACCGATCACGTTGACCAAAGAATGCCTAGATGTAGATTTGGGTTTTTCCAAGTCGTT
 F  T  D  H  V  D  Q  R  M  P  R  C  R  F  G  F  F  Q  V  V 850         860         870         880         890         900
         |           |           |           |           |           |
AACAACAACTACGACAGATGGGGAACGTACGCCATCGGTGGTAGCTCGGCCCCAACTATA
 N  N  N  Y  D  R  W  G  T  Y  A  I  G  G  S  S  A  P  T  I 910         920         930         940         950         960
         |           |           |           |           |           |
CTCAGCCAAGGGAACAGATTCTTCGCCCCCGATGATATCATCAAGGAAAATGTCTTAGCG
 L  S  Q  G  N  R  F  F  A  P  D  D  I  I  K  E  N  V  L  A
```

Fig. 3
(Contiued)

```
       970       980       990      1000      1010      1020
        |         |         |         |         |         |
AGGACTGGTACTGGCAACGCAGAGTCGATGTCGTGGAACTGGAGAACAGATAAAGACTTG
  R  T  G  T  G  N  A  E  S  M  S  W  N  W  R  T  D  K  D  L 1030      1040      1050      1060      1070      1080
        |         |         |         |         |         |
CTTGAAAATGGTGCTATTTTTCTCCCATCCGGGTCTGATCCAGTGCTAACCCCTGAGCAA
  L  E  N  G  A  I  F  L  P  S  G  S  D  P  V  L  T  P  E  Q 1090      1100      1110      1120      1130      1140
        |         |         |         |         |         |
AAAGCAGGGATGATTCCAGCTGAACCAGGAGAAGCCGTTCTAAGACTCACTAGTAGTGCT
  K  A  G  M  I  P  A  E  P  G  E  A  V  L  R  L  T  S  S  A 1150      1160      1170      1180      1190      1200
        |         |         |         |         |         |
GGTGTACTCTCATGCCATCAAGGAGCACCTTGCTAAGCACCTGGCCAATTCCTAAGCTTT
  G  V  L  S  C  H  Q  G  A  P  C  -  A  P  G  Q  F  L  S  F 1210      1220      1230      1240      1250      1260
        |         |         |         |         |         |
TATAATAATCATAAATACTTATTTTATTTTATTTTTGATATTTTATATGAACCATTACGT
  Y  N  N  H  K  Y  L  F  Y  F  I  F  D  I  L  Y  E  P  L  R 1270      1280      1290      1300      1310      1320
        |         |         |         |         |         |
TCAAGTACTCTATTAACATGTTTTAAATTCATAAGAGTTTATTGATAAAAAAAAAAAAAA
  S  S  T  L  L  T  C  F  K  F  I  R  V  Y  -  -  K  K  K  K

CCGAATTC
  P  N
```

Fig. 3
(Contiued)

```
*********************************************
*   TRANSLATION OF A NUCLEIC ACID SEQUENCE   *
*********************************************

Done on DNA sequence KKLAPPER1.

DE   UNC CLONE 1

Total number of bases is: 323.
Analysis done on the complete sequence.
Done on (absolute) phase(s): 1.
Using the Universal genetic code.
```

```
            10        20        30        40        50        60
             |         |         |         |         |         |
         GAATTCGGCTGGAGAACGAATAAAGACGTGCTTGAAAATGGTGCTATTTTTGTTGCATCC

E  F  G  W  R  T  N  K  D  V  L  E  N  G  A  I  F  V  A  S 70        80        90       100       110       120
             |         |         |         |         |         |
         GGGGTCGATCCAGTGCTAACCCCTGAGCAAAGCGCAGGGATGATTCCAGCCGAACCAGGA

G  V  D  P  V  L  T  P  E  Q  S  A  G  M̄  I  P  A  E  P  G 130       140       150       160       170       180
             |         |         |         |         |         |
         GAGTCCGCTCTAAGCCTCACTAGTAGTGCTGGTGTACTCTCATGCCAACCCGGAGCACCT

E  S  A  L  S  L  T  S  S  A  G  V  L  S  C  Q  P  G  A  P 190       200       210       220       230       240
             |         |         |         |         |         |
         TGCTAAGCACCCGACCAATTACTAAGCACTTATAATGATCATTAATACTTTTTTTTATTT

```
          250       260       270       280       290       300
           |         |         |         |         |         |
TATTTTTGATATTTTATATGTACTAAGGTAATGGAAATGAACCTTTACCTTCTAGTACTC

Y  F  -  Y  F  I  C  T  K  V  M  E  M  N  L  Y  L  L  V  L 310       320
           |         |
TAAAAAAAAAAAAAAACCGAATTC
```

Fig. 4
(Contiued)

IPC CLONE #1

From:

```
              10         20         30         40         50         60
               |          |          |          |          |          |
  1 GAATTCCGAT TCTTGGAGGA ATTACCGAAG TTAAAGACAA TGATAACAGC GTCGATITCG
    CTTAAGGCTA AGAACCTCCT TAATGGCTTC AATTTCTGTT ACTATTGTCG CAGCTAAAGC

61 ACGAGCTTGC TAAATTCGCC ATCGCTGAAC ACAACAAGAA GGAGAATGCT GCTCTGGAGT
    TGCTCGAACG ATTTAAGCGG TAGCGACTTG TGTTGTTCTT CCTCTTACGA CGAGACCTCA

121 TTGGAAAAGT AATAGAAAAA AAGCAGCAGG CGGTACAGGG CACCATGTAT TATATAAAAG
    AACCTTTTCA TTATCTTTTT TTCGTCGTCC GCCATGTCCC GTGGTACATA ATATATTTTC

181 TGGAAGCAAA TGATGGTGGT GAGAAGAAAA CTTATGAAGC CAAGGTGTGG GTTAAGCTAT
    ACCTTCGTTT ACTACCACCA CTCTTCTTTT GAATACTTCG GTTCCACACC CAATTCGATA

241 GGGAAAATTT CAAGGAATTG CAGGAACTCA AACTTGTTTG ATGGACGGGT GTGTGCTATG
    CCCTTTTAAA GTTCCTTAAC GTCCTTGAGT TTGAACAAAC TACCTGCCCA CACACGATAC

301 ACAAAATAGC TCGAGCAGGT GAAGCATGAA TGTATAAATA TTCTTTTTAA GTTTAATAAT
    TGTTTTATCG AGCTCGTCCA CTTCGTACTT ACATATTTAT AAGAAAAATT CAAATTATTA

361 AAACATTTCT TGTAATATGG TACAGGTTTA TGTACTTTGG TATGTATAAC AGAAAACATA
    TTTGTAAAGA ACATTATACC ATGTCCAAAT ACATGAAACC ATACATATTG TCTTTTGTAT

421 TCATAAATTC AAACTTAGAA TTTTGGGAAT TC
    AGTATTTAAG TTTGAATCTT AAAACCCTTA AG
```

Total number of bases is: 452.
DNA sequence composition:   162 A;   59 C;   107 G;   124 T;

Sequence name: NIPC_CLONE1.

Fig. 5

IPC CLONE #5

From:

```
             10         20         30         40         50         60
              |          |          |          |          |          |
  1 GAATTCCCGA TTCTTGGAGG AATTACCGAA GTTAAAGACA ATGATAACAG CGTCGATTTC
    CTTAAGGGCT AAGAACCTCC TTAATGGCTT CAATTTCTGT TACTATTGTC GCAGCTAAAG

61 GACGAGCTTG CTAAATTCGC CATCACTCAA CACAACAAGA AGGAGAATGC TGCTCTGGAG
    CTGCTCGAAC GATTTAAGCG GTAGTGACTT GTGTTGTTCT TCCTCTTACG ACGAGACCTC

121 TTTGGAAAAG TAATAGAAAA AAAGCAGCAG GCGGTACAGG GCACCATGTA TTATATAAAA
    AAACCTTTTC ATTATCTTTT TTTCGTCGTC CGCCATGTCC CGTGGTACAT AATATATTTT

181 GCGGAAGCAA ATGATGGTGG TGAGAAGAAA ACTTATGAAG CCAAGGTGTG GGTTAAGCTA
    CGCCTTCGTT TACTACCACC ACTCTTCTTT TGAATACTTC GGTTCCACAC CCAATTCGAT

241 TGGGAAAATT TCAAGGAATT TGCAAGGAAC TCAAACCTTG TTTGATGATG CCACCTCACC
    ACCCTTTTAA AGTTCCTTAA ACGTTCCTTG AGTTTGGAAC AAACTACTAC GGTGGAGTGG

301 TTAACTCCAT ATGGACGGTG TGCTATGACA AAATAGCTCA AGGAGGTGAA GCATAAATGT
    AATTGAGGTA TACCTGCCAC ACGATACTGT TTTATCGAGT TCCTCCACTT CGTATTTACA

361 ATAAATATTC TTTTTAAGTT TAATAATAAA CATTTCTTGT AATATAGTAC AAGTTTATGT
    TATTTATAAG AAAAATTCAA ATTATTATTT GTAAAGAACA TTATATCATG TTCAAATACA

421 ACTTTGGTAT GTATAACAGA AAACATATCA TAAATTCAAA CTTAATGTTT TTTTTTCTCG
    TGAAACCATA CATATTGTCT TTTGTATAGT ATTTAAGTTT GAATTACAAA AAAAAAGAGC

481 CGGAATTC
    GCCTTAAG
```

Total number of bases is: 488.
DNA sequence composition:    174 A;    74 C;    103 G;    137 T;

Sequence name: NIPC_CLONE5.

Fig. 6

IPC CLONE #6

From:

```
            10         20         30         40         50         60
             |          |          |          |          |          |
   1 TCGATTCGCT GTCGATGAAC ACAACAAGAA GCAGAATACC CTGCTGGAAT TTAAGAAGGT
     AGCTAAGCGA CAGCTACTTG TGTTGTTCTT CGTCTTATGG GACGACCTTA AATTCTTCCA

61 ACTGAATACA AAGGAGCAGG TAGTAGCTGG TATAATGTAT TATATCACAC TTGAAGCAAC
     TGACTTATGT TTCCTCGTCC ATCATCGACC ATATTACATA ATATAGTGTG AACTTCGTTG

121 TGATGGTGGT GAGAAAAAGA CTTATGAAGC CAAGGTTTGG GTTAAGCCAT GGGAAAACTT
     ACTACCACCA CTCTTTTTCT GAATACTTCG GTTCCAAACC CAATTCGGTA CCCTTTTGAA

181 CAAAGAATTC
     GTTTCTTAAG
```

Total number of bases is: 190.
DNA sequence composition:    69 A;    29 C;    47 G;    45 T;

Sequence name: NIPC_CLONE6.

Fig. 7

```
*********************************************
* TRANSLATION OF A NUCLEIC ACID SEQUENCE *
*********************************************
Done on DNA sequence AMB_A_IA.

DE    SEQUENCE OF AMB A IA CLONE.

Total number of bases is: 1196.
Analysis done on the complete sequence.
Done on (absolute) phase(s): 1.
Using the Universal genetic code.
```

```
              10        20        30        40        50        60
               |         |         |         |         |         |
         TTGTATTTTACCTTAGCCCTTGTCACTTTGCTGCAACCTGTTCGTTCTGCCGAAGATCTC
           L  Y  F  T  L  A  L  V  T  L  L  Q  P  V  R  S  A  E  D  L 70        80        90       100       110       120
               |         |         |         |         |         |
         CAGGAAATCTTACCAGTTAACGAAACAAGGAGGCTGACAACAAGTGGAGCATACAACATT
           Q  E  I  L  P  V  N  E  T  R  R  L  T  T  S  G  A  Y  N  I 130       140       150       160       170       180
               |         |         |         |         |         |
         ATAGACGGGTGCTGGAGGGGCAAAGCCGATTGGGCGGAAAACCGAAAAGCGTTAGCCGAT
            I  D  G  C  W  R  G  K  A  D  W  A  E  N  R  K  A  L  A  D 190       200       210       220       230       240
               |         |         |         |         |         |
         TGTGCCCAAGGTTTTGGGAAGGGAACAGTGGGCGGAAAAGATGGTGATATATACACGGTC
            C  A  Q  G  F  G  K  G  T  V  G  G  K  D  G  D  I  Y  T  V 250       260       270       280       290       300
               |         |         |         |         |         |
         ACCAGTGAGCTAGATGATGATGTTGCAAATCCAAAAGAAGGCACACTCCGGTTTGGTGCC
            T  S  E  L  D  D  D  V  A  N  P  K  E  G  T  L  R  F  G  A 310       320       330       340       350       360
               |         |         |         |         |         |
         GCCCAAAACAGGCCCTTGTGGATCATTTTTGAAAGAGATATGGTGATTCGTTTGGATAAA
            A  Q  N  R  P  L  W  I  I  F  E  R  D  M  V  I  R  L  D  K 370       380       390       400       410       420
               |         |         |         |         |         |
         GAGATGGTGGTAAACAGTGACAAGACCATCGATGGCCGAGGGGCGAAAGTTGAAATCATT
            E  M  V  V  N  S  D  K  T  I  D  G  R  G  A  K  V  E  I  I
```

Fig. 11

```
         430        440        450        460        470        480
          |          |          |          |          |          |
AACGCTGGTTTCACCCTTAATGGTGTCAAGAATGTAATCATTCATAACATAAATATGCAT
 N  A  G  F  T  L  N  G  V  K  N  V  I  I  H  N  I  N  M  H 490        500        510        520        530        540
          |          |          |          |          |          |
GATGTTAAAGTGAATCCAGGAGGCCTGATTAAGTCCAACGATGGTCCAGCAGCTCCAAGA
 D  V  K  V  N  P  G  G  L  I  K  S  N  D  G  P  A  A  P  R 550        560        570        580        590        600
          |          |          |          |          |          |
GCTGGTAGTGATGGTGATGCTATAAGTATTTCTGGTAGTTCACAAATATGGATCGACCAT
 A  G  S  D  G  D  A  I  S  I  S  G  S  S  Q  I  W  I  D  H 610        620        630        640        650        660
          |          |          |          |          |          |
TGTTCGCTCAGTAAGTCTGTTGATGGGCTGGTAGATGCCAAGCTCGGCACCACACGCTTA
 C  S  L  S  K  S  V  D  G  L  V  D  A  K  L  G  T  T  R  L 670        680        690        700        710        720
          |          |          |          |          |          |
ACCGTTTCCAACAGCTTATTCACCCAACACCAGTTTGTACTATTATTCGGGGCTGGTGAC
 T  V  S  N  S  L  F  T  Q  H  Q  F  V  L  L  F  G  A  G  D 730        740        750        760        770        780
          |          |          |          |          |          |
GAAAATATTGAAGATAGAGGCATGCTAGCAACGGTCGCTTTCAACACGTTCACTGATAAC
 E  N  I  E  D  R  G  M  L  A  T  V  A  F  N  T  F  T  D  N 790        800        810        820        830        840
          |          |          |          |          |          |
GTTGACCAAAGAATGCCTAGATGTCGACATGGGTTTTTCCAAGTCGTTAACAACAACTAT
 V  D  Q  R  M  P  R  C  R  H  G  F  F  Q  V  V  N  N  N  Y 850        860        870        880        890        900
          |          |          |          |          |          |
GATAAATGGGGATCGTATGCCATCGGTGGTAGCGCGTCCCCAACCATACTCAGCCAAGGG
 D  K  W  G  S  Y  A  I  G  G  S  A  S  P  T  I  L  S  Q  G 910        920        930        940        950        960
          |          |          |          |          |          |
AACAGATTCTGCGCCCCCGATGAACGCAGCAAGAAAAATGTCCTAGGAAGGCATGGTGAA
 N  R  F  C  A  P  D  E  R  S  K  K  N  V  L  G  R  H  G  E
```

Fig. 11
(Contiued)

```
         970       980       990      1000      1010      1020
          |         |         |         |         |         |
GCCGCCGCAGAGTCGATGAAGTGGAACTGGAGAACGAATAAAGACGTGCTTGAAAATGGT
 A  A  A  E  S  M  K  W  N  W  R  T  N  K  D  V  L  E  N  G 1030      1040      1050      1060      1070      1080
          |         |         |         |         |         |
GCTATTTTTGTTGCATCCGGGGTCGATCCAGTGCTAACCCCTGAGCAAAGCGCAGGGATG
 A  I  F  V  A  S  G  V  D  P  V  L  T  P  E  Q  S  A  G  M 1090      1100      1110      1120      1130      1140
          |         |         |         |         |         |
ATTCCAGCCGAACCAGGAGAGTCCGCTCTAAGCCTCACTAGTAGTGCTGGTGTACTCTCA
 I  P  A  E  P  G  E  S  A  L  S  L  T  S  S  A  G  V  L  S 1150      1160      1170      1180      1190
          |         |         |         |         |
TGCCAACCCGGAGCACCTTGCTAAGCACCCGACCAATTACTAAGCACTTATAATGA
 C  Q  P  G  A  P  C  -  A  P  D  Q  L  L  S  T  Y  N
```

Fig. 11
(Contiued)

```
*******************************************
* TRANSLATION OF A NUCLEIC ACID SEQUENCE *
*******************************************
Done on DNA sequence AMB_A_IB.

DE   SEQUENCE OF AMB A IB CLONE.

Total number of bases is: 1349.
Analysis done on the complete sequence.
Done on (absolute) phase(s): 1.
Using the Universal genetic code.
```

```
            10        20        30        40        50        60
             |         |         |         |         |         |
        ATGGGGATCAAACACTGTTGTTACATCTTGTATTTTACCTTAGCCCTTGTCACTTTGCTG
         M  G  I  K  H  C  C  Y  I  L  Y  F  T  L  A  L  V  T  L  L 70        80        90       100       110       120
             |         |         |         |         |         |
        CAACCTGTTCGTTCTGCAGAAGATGTTGAAGAATTCTTACCTTCAGCTAACGAAACAAGG
         Q  P  V  R  S  A  E  D  V  E  E  F  L  P  S  A  N  E  T  R 130       140       150       160       170       180
             |         |         |         |         |         |
        AGGAGCCTGAAAGCATGTGAAGCACACAACATTATAGACAAGTGCTGGAGGTGCAAAGCC
         R  S  L  K  A  C  E  A  H  N  I  I  D  K  C  W  R  C  K  A 190       200       210       220       230       240
             |         |         |         |         |         |
        GATTGGGCGAATAACCGACAAGCGTTAGCCGATTGTGCCCAAGGTTTTGCAAAGGGAACC
         D  W  A  N  N  R  Q  A  L  A  D  C  A  Q  G  F  A  K  G  T 250       260       270       280       290       300
             |         |         |         |         |         |
        TACGGTGGAAAACATGGTGATGTCTACACGGTCACCAGTGATAAAGATGATGATGTTGCA
         Y  G  G  K  H  G  D  V  Y  T  V  T  S  D  K  D  D  D  V  A 310       320       330       340       350       360
             |         |         |         |         |         |
        AATCCAAAAGAAGGCACACTCCGGTTTGCTGCTGCCCAAAACAGGCCCTTGTGGATCATT
         N  P  K  E  G  T  L  R  F  A  A  A  Q  N  R  P  L  W  I  I 370       380       390       400       410       420
             |         |         |         |         |         |
        TTTAAAAGAAATATGGTGATTCATTTGAATCAAGAGCTTGTCGTAAACAGCGACAAGACC
         F  K  R  N  M  V  I  H  L  N  Q  E  L  V  V  N  S  D  K  T
```

Fig. 12

```
          430        440        450        460        470        480
           |          |          |          |          |          |
ATCGATGGCCGAGGGGTGAAAGTTAACATCGTTAACGCCGGTCTCACCCTCATGAATGTC
 I  D  G  R  G  V  K  V  N  I  V  N  A  G  L  T  L  M  N  V 490        500        510        520        530        540
           |          |          |          |          |          |
AAGAATATAATCATTCATAACATAAATATCCATGATATTAAAGTTTGTCCAGGAGGCATG
 K  N  I  I  I  H  N  I  N  I  H  D  I  K  V  C  P  G  G  M 550        560        570        580        590        600
           |          |          |          |          |          |
ATTAAGTCCAACGATGGTCCACCAATTTTAAGACAACAAAGTGATGGTGATGCTATAAAT
 I  K  S  N  D  G  P  P  I  L  R  Q  Q  S  D  G  D  A  I  N 610        620        630        640        650        660
           |          |          |          |          |          |
GTTGCTGGTAGTTCACAAATATGGATCGACCATTGCTCGCTCAGTAAGGCTTCCGATGGG
 V  A  G  S  S  Q  I  W  I  D  H  C  S  L  S  K  A  S  D  G 670        680        690        700        710        720
           |          |          |          |          |          |
CTGCTCGATATCACCCTCGGCAGCTCACACGTGACCGTTTCCAACTGCAAATTCACCCAA
 L  L  D  I  T  L  G  S  S  H  V  T  V  S  N  C  K  F  T  Q 730        740        750        760        770        780
           |          |          |          |          |          |
CACCAATTTGTATTATTGCTCGGGGCTGATGACACCCATTATCAAGATAAAGGCATGCTA
 H  Q  F  V  L  L  G  A  D  D  T  H  Y  Q  D  K  G  M  L 790        800        810        820        830        840
           |          |          |          |          |          |
GCAACGGTAGCATTCAACATGTTCACCGATCACGTTGACCAAAGAATGCCTAGATGTAGA
 A  T  V  A  F  N  M  F  T  D  H  V  D  Q  R  M  P  R  C  R 850        860        870        880        890        900
           |          |          |          |          |          |
TTTGGGTTTTTCCAAGTCGTTAACAACAACTACGACAGATGGGGAACGTACGCCATCGGT
 F  G  F  F  Q  V  V  N  N  N  Y  D  R  W  G  T  Y  A  I  G 910        920        930        940        950        960
           |          |          |          |          |          |
GGTAGCTCGGCCCCAACTATACTCAGCCAAGGGAACAGATTCTTCGCCCCCGATGATATC
 G  S  S  A  P  T  I  L  S  Q  G  N  R  F  F  A  P  D  D  I
```

Fig. 12
(Contiued)

```
         970       980       990      1000      1010      1020
          |         |         |         |         |         |
ATCAAGAAAAATGTCTTAGCGAGGACTGGTACTGGCAACGCAGAGTCGATGTCGTGGAAC
 I  K  K  N  V  L  A  R  T  G  T  G  N  A  E  S  M  S  W  N 1030      1040      1050      1060      1070      1080
          |         |         |         |         |         |
TGGAGAACAGATAGAGACTTGCTTGAAAATGGTGCTATTTTTCTCCCATCCGGGTCTGAT
 W  R  T  D  R  D  L  L  E  N  G  A  I  F  L  P  S  G  S  D 1090      1100      1110      1120      1130      1140
          |         |         |         |         |         |
CCAGTGCTAACCCCTGAGCAAAAAGCAGGGATGATTCCAGCTGAACCAGGAGAAGCCGTT
 P  V  L  T  P  E  Q  K  A  G  M  I  P  A  E  P  G  E  A  V 1150      1160      1170      1180      1190      1200
          |         |         |         |         |         |
CTAAGACTCACTAGTAGTGCTGGTGTACTCTCATGCCATCAAGGAGCACCTTGCTAAGCA
 L  R  L  T  S  S  A  G  V  L  S  C  H  Q  G  A  P  C  -  A 1210      1220      1230      1240      1250      1260
          |         |         |         |         |         |
CCTGGCCAATTCCTAAGCTTTTATAATAATCATAAATACTTATTTATTTTATTTTTGAT
 P  G  Q  F  L  S  F  Y  N  N  H  K  Y  L  F  Y  F  I  F  D 1270      1280      1290      1300      1310      1320
          |         |         |         |         |         |
ATTTTATATGAACCATTACGTTCAAGTACTCTATTAACATGTTTTAAATTCATAAGAGTT
 I  L  Y  E  P  L  R  S  S  T  L  L  T  C  F  K  F  I  R  V 1330      1340
          |         |
TATTGATAAAAAAAAAAAAAAAACCGAATTC
 Y  -  -  K  K  K  K  P  N
```

Fig. 12
(Contiued)

```
*******************************************
* TRANSLATION OF A NUCLEIC ACID SEQUENCE *
*******************************************
Done on DNA sequence AMB_A_IC.

DE    SEQUENCE OF AMB A IC CLONE.

Total number of bases is: 1320.
Analysis done on the complete sequence.
Done on (absolute) phase(s): 1.
Using the Universal genetic code.
```

```
             10        20        30        40        50        60
              |         |         |         |         |         |
         ATGGGGATCAAACAATGTTGTTACATCTTGTATTTTACCTTAGCACTTGTCGCTTTGCTG
          M  G  I  K  Q  C  C  Y  I  L  Y  F  T  L  A  L  V  A  L  L 70        80        90       100       110       120
              |         |         |         |         |         |
         CAACCTGTTCGTTCTGCCGAAGGTGTCGGGGAAATCTTACCTTCAGTTAACGAAACGAGG
          Q  P  V  R  S  A  E  G  V  G  E  I  L  P  S  V  N  E  T  R 130       140       150       160       170       180
              |         |         |         |         |         |
         AGCCTGCAAGCATGTGAAGCACTCAACATTATAGACAAGTGCTGGAGGGGCAAAGCCGAT
          S  L  Q  A  C  E  A  L  N  I  I  D  K  C  W  R  G  K  A  D 190       200       210       220       230       240
              |         |         |         |         |         |
         TGGGAGAACAACCGACAAGCGTTAGCCGACTGTGCCCAAGGTTTTGCAAAGGGAACCTAC
          W  E  N  N  R  Q  A  L  A  D  C  A  Q  G  F  A  K  G  T  Y 250       260       270       280       290       300
              |         |         |         |         |         |
         GGCGGAAAATGGGGTGATGTCTACACGGTCACCAGCAATCTAGATGATGATGTTGCAAAT
          G  G  K  W  G  D  V  Y  T  V  T  S  N  L  D  D  D  V  A  N 310       320       330       340       350       360
              |         |         |         |         |         |
         CCAAAAGAAGGCACACTCCGGTTTGCTGCCGCCCAAAACAGGCCCTTGTGGATCATTTTT
          P  K  E  G  T  L  R  F  A  A  A  Q  N  R  P  L  W  I  I  F 370       380       390       400       410       420
              |         |         |         |         |         |
         AAAAATGATATGGTGATTAATTTGAATCAAGAGCTTGTCGTAAACAGCGACAAGACCATC
          K  N  D  M  V  I  N  L  N  Q  E  L  V  V  N  S  D  K  T  I
```

Fig. 13

```
           430         440         450         460         470         480
            |           |           |           |           |           |
GATGGCCGAGGGGTGAAAGTTGAAATCATTAACGGAGGTCTCACCCTCATGAATGTCAAG
 D   G   R   G   V   K   V   E   I   I   N   G   G   L   T   L   M   N   V   K 490         500         510         520         530         540
            |           |           |           |           |           |
AATATAATCATTCATAACATAAATATCCATGATGTTAAAGTGCTTCCAGGAGGCATGATT
 N   I   I   I   H   N   I   N   I   H   D   V   K   V   L   P   G   G   M   I 550         560         570         580         590         600
            |           |           |           |           |           |
AAGTCCAACGATGGTCCACCAATTTTAAGACAAGCAAGTGATGGGGATACTATAAATGTT
 K   S   N   D   G   P   P   I   L   R   Q   A   S   D   G   D   T   I   N   V 610         620         630         640         650         660
            |           |           |           |           |           |
GCTGGTAGTTCCCAAATATGGATAGACCATTGCTCACTCAGCAAGTCTTTCGATGGGCTG
 A   G   S   S   Q   I   W   I   D   H   C   S   L   S   K   S   F   D   G   L 670         680         690         700         710         720
            |           |           |           |           |           |
GTCGATGTCACCCTCGGTAGCACACACGTGACCATTTCCAACTGCAAATTCACCCAACAG
 V   D   V   T   L   G   S   T   H   V   T   I   S   N   C   K   F   T   Q   Q 730         740         750         760         770         780
            |           |           |           |           |           |
TCAAAAGCAATATTGTTGGGAGCAGATGACACCCATGTTCAAGATAAAGGAATGCTAGCA
 S   K   A   I   L   L   G   A   D   D   T   H   V   Q   D   K   G   M   L   A 790         800         810         820         830         840
            |           |           |           |           |           |
ACGGTCGCTTTCAACATGTTCACCGATAACGTTGACCAAAGAATGCCTAGATGTCGATTT
 T   V   A   F   N   M   F   T   D   N   V   D   Q   R   M   P   R   C   R   F 850         860         870         880         890         900
            |           |           |           |           |           |
GGGTTTTTCCAAGTTGTTAACAACAACTACGACAGATGGGGAACGTACGCCATAGGTGGT
 G   F   F   Q   V   V   N   N   N   Y   D   R   W   G   T   Y   A   I   G   G 910         920         930         940         950         960
            |           |           |           |           |           |
AGCTCGGCCCCAACTATACTCTGCCAAGGGAACAGATTCTTGGCCCCTGATGATCAGATC
 S   S   A   P   T   I   L   C   Q   G   N   R   F   L   A   P   D   D   Q   I
```

Fig. 13
(Contiued)

```
            970       980       990      1000      1010      1020
             |         |         |         |         |         |
AAGAAAAATGTCCTAGCGAGGACTGGTACAGGCGCTGCTGAGTCGATGGCGTGGAACTGG
 K  K  N  V  L  A  R  T  G  T  G  A  A  E  S  M  A  W  N  W 1030      1040      1050      1060      1070      1080
             |         |         |         |         |         |
AGATCTGATAAAGACTTGCTTGAAAATGGTGCTATTTTTGTTACATCTGGGTCTGATCCA
 R  S  D  K  D  L  L  E  N  G  A  I  F  V  T  S  G  S  D  P 1090      1100      1110      1120      1130      1140
             |         |         |         |         |         |
GTGCTAACCCCTGTTCAAAGCGCAGGGATGATTCCAGCTGAACCAGGAGAAGCCGCTATA
 V  L  T  P  V  Q  S  A  G  M  I  P  A  E  P  G  E  A  A  I 1150      1160      1170      1180      1190      1200
             |         |         |         |         |         |
AAACTCACTAGTAGTGCTGGTGTATTCTCATGCCGTCCTGGAGCACCTTGCTAAGCACCC
 K  L  T  S  S  A  G  V  F  S  C  R  P  G  A  P  C  -  A  P 1210      1220      1230      1240      1250      1260
             |         |         |         |         |         |
TGCCAATTCTCCTAAGCTTTTGCAATGATCAAAAATACTTTTTTATTTTATTTTTAATAT
 C  Q  F  S  -  A  F  A  M  I  K  N  T  F  L  F  Y  F  -  Y 1270      1280      1290      1300      1310      1320
             |         |         |         |         |         |
TTTATATGTACTGGAAATGAACCATTACCTTCTAGTACTCTATAACATGTTTTGCATTTA
 F  I  C  T  G  N  E  P  L  P  S  S  T  L  -  H  V  L  H  L
```

Fig. 13
(Contiued)

```
*******************************************
* TRANSLATION OF A NUCLEIC ACID SEQUENCE *
*******************************************
Done on DNA sequence AMB_A_ID.

DE   SEQUENCE OF AMB A ID CLONE.

Total number of bases is: 1160.
Analysis done on the complete sequence.
Done on (absolute) phase(s): 1.
Using the Universal genetic code.

------------------------------------------

10        20        30        40        50        60
          |         |         |         |         |         |
     TTGTATTTTACCTTAGCCCTTGTCACTTTGCTGCAACCTGTTCGTTCTGCCGAAGATCTC
        L  Y  F  T  L  A  L  V  T  L  L  Q  P  V  R  S  A  E  D  L 70        80        90       100       110       120
          |         |         |         |         |         |
     CAGGAAATCTTACCTTCAGCTAACGAAACAAGGAGCCTGACAACATGTGGAACATACAAC
        Q  E  I  L  P  S  A  N  E  T  R  S  L  T  T  C  G  T  Y  N 130       140       150       160       170       180
          |         |         |         |         |         |
     ATTATAGACGGGTGCTGGAGGGGCAAAGCCGATTGGGCGGAAAACCGAAAAGCGTTAGCC
        I  I  D  G  C  W  R  G  K  A  D  W  A  E  N  R  K  A  L  A 190       200       210       220       230       240
          |         |         |         |         |         |
     GATTGTGCCCAAGGTTTTGCAAAGGGAACAATCGGCGGAAAAGATGGTGATATATACACG
        D  C  A  Q  G  F  A  K  G  T  I  G  G  K  D  G  D  I  Y  T 250       260       270       280       290       300
          |         |         |         |         |         |
     GTCACCAGTGAGCTAGATGATGATGTTGCAAATCCAAAAGAAGGCACACTCCGGTTTGGT
        V  T  S  E  L  D  D  D  V  A  N  P  K  E  G  T  L  R  F  G 310       320       330       340       350       360
          |         |         |         |         |         |
     GCCGCCCAAAACAGGCCCTTGTGGATTATTTTTGAAAGAGATATGGTGATTCGTTTGGAT
        A  A  Q  N  R  P  L  W  I  I  F  E  R  D  M  V  I  R  L  D 370       380       390       400       410       420
          |         |         |         |         |         |
     AGAGAGTTGGCTATAAACAACGACAAGACCATCGATGGCCGAGGGGCGAAAGTTGAAATC
        R  E  L  A  I  N  N  D  K  T  I  D  G  R  G  A  K  V  E  I
```

Fig. 14

```
        430       440       450       460       470       480
         |         |         |         |         |         |
ATTAACGCTGGTTTCGCCATCTATAATGTCAAGAATATAATCATTCATAACATAATTATG
 I  N  A  G  F  A  I  Y  N  V  K  N  I  I  I  H  N  I  I  M 490       500       510       520       530       540
         |         |         |         |         |         |
CATGATATTGTAGTGAATCCAGGAGGCCTGATTAAGTCCCACGATGGTCCACCAGTTCCA
 H  D  I  V  V  N  P  G  G  L  I  K  S  H  D  G  P  P  V  P 550       560       570       580       590       600
         |         |         |         |         |         |
AGAAAGGGTAGTGATGGTGATGCTATAGGTATTTCTGGTGGTTCACAAATATGGATCGAC
 R  K  G  S  D  G  D  A  I  G  I  S  G  G  S  Q  I  W  I  D 610       620       630       640       650       660
         |         |         |         |         |         |
CATTGCTCCCTCAGTAAGGCTGTTGATGGGCTAATCGATGCTAAACACGGCAGCACACAC
 H  C  S  L  S  K  A  V  D  G  L  I  D  A  K  H  G  S  T  H 670       680       690       700       710       720
         |         |         |         |         |         |
TTCACCGTTTCTAACTGCTTATTCACCCAACACCAATATTTATTATTGTTCTGGGATTTT
 F  T  V  S  N  C  L  F  T  Q  H  Q  Y  L  L  F  W  D  F 730       740       750       760       770       780
         |         |         |         |         |         |
GACGAGCGAGGCATGCTATGTACGGTCGCATTCAACAAGTTCACTGATAACGTTGACCAA
 D  E  R  G  M  L  C  T  V  A  F  N  K  F  T  D  N  V  D  Q 790       800       810       820       830       840
         |         |         |         |         |         |
AGAATGCCTAACTTACGACATGGGTTTGTCCAAGTCGTTAACAACAACTACGAAAGATGG
 R  M  P  N  L  R  H  G  F  V  Q  V  V  N  N  N  Y  E  R  W 850       860       870       880       890       900
         |         |         |         |         |         |
GGATCGTACGCCCTCGGTGGTAGCGCAGGCCCAACCATACTTAGCCAAGGGAACAGATTC
 G  S  Y  A  L  G  G  S  A  G  P  T  I  L  S  Q  G  N  R  F 910       920       930       940       950       960
         |         |         |         |         |         |
TTAGCCTCCGATATCAAGAAAGAGGTCGTAGGGAGGTATGGTGAATCCGCCATGTCAGAG
 L  A  S  D  I  K  K  E  V  V  G  R  Y  G  E  S  A  M  S  E
```

Fig. 14
(Contiued)

```
        970       980       990      1000      1010      1020
         |         |         |         |         |         |
TCGATTAATTGGAACTGGAGATCGTATATGGACGTATTTGAAAATGGTGCTATTTTTGTT
 S  I  N  W  N  W  R  S  Y  M  D  V  F  E  N  G  A  I  F  V 1030      1040      1050      1060      1070      1080
         |         |         |         |         |         |
CCATCCGGGGTTGATCCAGTGCTAACCCCTGAGCAAAACGCAGGGATGATTCCAGCCGAA
 P  S  G  V  D  P  V  L  T  P  E  Q  N  A  G  M  I  P  A  E 1090      1100      1110      1120      1130      1140
         |         |         |         |         |         |
CCAGGAGAAGCCGTTCTAAGACTCACTAGTAGTGCTGGTGTCCTCTCATGCCAACCTGGA
 P  G  E  A  V  L  R  L  T  S  S  A  G  V  L  S  C  Q  P  G 1150      1160
         |         |
GCACCTTGCTAAGCACTGCA
 A  P  C  -  A  L
```

Fig. 14
(Contiued)

```
*******************************************
* TRANSLATION OF A NUCLEIC ACID SEQUENCE *
*******************************************
Done on DNA sequence AMB_A_II.

DE    SEQUENCE OF AMB A II CLONE.

Total number of bases is: 1368.
Analysis done on the complete sequence.
Done on (absolute) phase(s): 1.
Using the Universal genetic code.
```

```
              10        20        30        40        50        60
               |         |         |         |         |         |
          TTGTATTTTACCTTAGCACTTGTCACTTTGGTGCAAGCTGGACGTCTTGGCGAAGAGGTC
            L  Y  F  T  L  A  L  V  T  L  V  Q  A  G  R  L  G  E  E  V 70        80        90       100       110       120
               |         |         |         |         |         |
          GACATCTTACCTTCACCTAACGATACAAGGAGGAGCCTGCAAGGATGTGAAGCACACAAC
            D  I  L  P  S  P  N  D  T  R  R  S  L  Q  G  C  E  A  H  N 130       140       150       160       170       180
               |         |         |         |         |         |
          ATTATAGACAAGTGTTGGAGGTGCAAACCCGATTGGGCGGAGAACCGACAAGCGTTAGGC
            I  I  D  K  C  W  R  C  K  P  D  W  A  E  N  R  Q  A  L  G 190       200       210       220       230       240
               |         |         |         |         |         |
          GATTGTGCGCAAGGTTTTGGAAAGGCAACTCACGGCGGAAAATGGGGTGATATCTACATG
            D  C  A  Q  G  F  G  K  A  T  H  G  G  K  W  G  D  I  Y  M 250       260       270       280       290       300
               |         |         |         |         |         |
          GTCACAAGTGATCAGGATGATGATGTTGTAAATCCAAAAGAAGGCACACTCCGGTTCGGT
            V  T  S  D  Q  D  D  D  V  V  N  P  K  E  G  T  L  R  F  G 310       320       330       340       350       360
               |         |         |         |         |         |
          GCTACCCAGGACAGGCCCTTGTGGATCATTTTTCAAAGAGATATGATTATTTATTTGCAA
            A  T  Q  D  R  P  L  W  I  I  F  Q  R  D  M  I  I  Y  L  Q 370       380       390       400       410       420
               |         |         |         |         |         |
          CAAGAGATGGTCGTAACCAGCGACACGACCATTGATGGTCGAGGGGCGAAAGTTGAGCTC
            Q  E  M  V  V  T  S  D  T  T  I  D  G  R  G  A  K  V  E  L
```

Fig. 15

```
        430       440       450       460       470       480
         |         |         |         |         |         |
GTTTATGGAGGTATCACCCTCATGAATGTCAAGAATGTAATCATTCACAACATAGATATC
 V  Y  G  G  I  T  L  M  N  V  K  N  V  I  I  H  N  I  D  I 490       500       510       520       530       540
         |         |         |         |         |         |
CATGATGTTAGAGTGCTTCCAGGAGGTAGGATTAAGTCCAATGGTGGTCCAGCCATACCA
 H  D  V  R  V  L  P  G  G  R  I  K  S  N  G  G  P  A  I  P 550       560       570       580       590       600
         |         |         |         |         |         |
AGACATCAGAGTGATGGTGATGCTATCCATGTTACGGGTAGTTCAGACATATGGATCGAC
 R  H  Q  S  D  G  D  A  I  H  V  T  G  S  S  D  I  W  I  D 610       620       630       640       650       660
         |         |         |         |         |         |
CATTGCACGCTCAGTAAGTCATTTGATGGGCTCGTCGATGTCAACTGGGGCAGCACAGGA
 H  C  T  L  S  K  S  F  D  G  L  V  D  V  N  W  G  S  T  G 670       680       690       700       710       720
         |         |         |         |         |         |
GTAACCATTTCCAACTGCAAATTCACCCACCACGAAAAAGCTGTTTTGCTCGGGGCTAGT
 V  T  I  S  N  C  K  F  T  H  H  E  K  A  V  L  L  G  A  S 730       740       750       760       770       780
         |         |         |         |         |         |
GACACGCATTTTCAAGATCTGAAAATGCATGTAACGCTTGCATACAACATCTTCACCAAT
 D  T  H  F  Q  D  L  K  M  H  V  T  L  A  Y  N  I  F  T  N 790       800       810       820       830       840
         |         |         |         |         |         |
ACCGTTCACGAAAGAATGCCCAGATGCCGATTTGGGTTTTTCCAAATCGTTAACAACTTC
 T  V  H  E  R  M  P  R  C  R  F  G  F  F  Q  I  V  N  N  F 850       860       870       880       890       900
         |         |         |         |         |         |
TACGACAGATGGGATAAGTACGCCATCGGTGGTAGCTCGAACCCTACTATTCTCAGCCAA
 Y  D  R  W  D  K  Y  A  I  G  G  S  S  N  P  T  I  L  S  Q 910       920       930       940       950       960
         |         |         |         |         |         |
GGGAACAAATTCGTGGCCCCCGATTTCATTTACAAGAAAAACGTCTGTCTAAGGACTGGT
 G  N  K  F  V  A  P  D  F  I  Y  K  K  N  V  C  L  R  T  G
```

Fig. 15
(Contiued)

```
        970       980       990       1000      1010      1020
         |         |         |         |         |         |
GCACAGGAGCCAGAATGGATGACTTGGAACTGGAGAACACAAAACGACGTGCTTGAAAAT
 A  Q  E  P  E  W  M  T  W  N  W  R  T  Q  N  D  V  L  E  N 1030      1040      1050      1060      1070      1080
         |         |         |         |         |         |
GGTGCTATCTTTGTGGCATCTGGGTCTGATCCAGTGCTAACCGCTGAACAAAATGCAGGC
  G  A  I  F  V  A  S  G  S  D  P  V  L  T  A  E  Q  N  A  G 1090      1100      1110      1120      1130      1140
         |         |         |         |         |         |
ATGATGCAAGCTGAACCGGGAGATATGGTTCCACAACTCACCATGAATGCAGGTGTACTC
 M  M  Q  A  E  P  G  D  M  V  P  Q  L  T  M  N  A  G  V  L 1150      1160      1170      1180      1190      1200
         |         |         |         |         |         |
ACATGCTCGCCTGGAGCACCTTGCTAAGCACCTGGCCAATTCCTATGCAACGATCATAAA
  T  C  S  P  G  A  P  C  -  A  P  G  Q  F  L  C  N  D  H  K 1210      1220      1230      1240      1250      1260
         |         |         |         |         |         |
TACTTGCTCACCATAAGTGTTCATTTGATTAGATTTGGACACGAATGATGTAACCGATTC
  Y  L  L  T  I  S  V  H  L  I  R  F  G  H  E  -  C  N  R  F 1270      1280      1290      1300      1310      1320
         |         |         |         |         |         |
GTCTGAATTATGATTTGTTTTGATTCTCAGTTTCATAATATGGCTTCTTGAGAGCAAAAT
 V  -  I  M  I  C  F  D  S  Q  F  H  N  M  A  S  -  E  Q  N 1330      1340      1350      1360
         |         |         |         |
TAGAGAAGAGTGTCTTTGATCAACTACATTTTATGGTTTTTATATTAA
 -  R  R  V  S  L  I  N  Y  I  L  W  F  L  Y  -
```

Fig. 15
(Contiued)

SDS - PAGE WESTERN BLOT
binding of anti-Amb a I antibody
to recombinant Amb a I proteins Sample Loaded
1 - Pollen Extract
2 - JM 109
3 - Amb a I A
4 - Amb a I B
5 - Amb a I C
6 - Amb a II A ically related. King, T. P.,
ALLERGENIC PEPTIDES FROM RAGWEED POLLEN

RELATED APPLICATIONS

This application is a continuation application of U.S. Ser. No. 08/290,448, filed Aug. 15, 1994, now U.S. Pat. No. 5,698,204, which is in turn a continuation application of U.S. Ser. No. 07/529,951, filed May 29, 1990, now abandoned, which in turn is a continuation-in-part application of U.S. Ser. No. 07/325,365, filed Mar. 17, 1989, now abandoned. The contents of these applications are incorporated herein by reference.

FUNDING

Work described herein was supported by the National Institutes of Health (Grant No. AI14908).

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity in people are called allergens. King, T. P., *Adv. Immun.*, 23:77–105 (1976). Anaphylaxis or atopy, which includes the symptoms of hay fever, asthma and hives, is one form of immediate allergy. It can be caused by a variety of atopic allergens, such as products of grasses, trees, weeds, animal dander, insects, and food, drugs and chemicals. The antibodies involved in atopic allergy belong primarily to the IgE class of immunoglobulins. IgE binds to mast cells and basophils. Upon combination of a specific allergen with IgE bound to mast cells, the IgE is cross-linked on the cell surface, resulting in the physiological effects of IgE-antigen interaction. Degranulation results in release of, among other substances, histamine, heparin, a chemotactic factor for eosinophilic leukocytes and the leukotrienes, C4, D4 and E4, which cause prolonged constriction of bronchial smooth muscle cells. Hood, L. E. et al., *Immunology*, (2nd ed.), pp460–462, The Benjamin/Cumming Publishing Co., Inc. (1984). These released substances are the mediators which result in allergic symptoms caused by combination of IgE with a specific allergen. Through them, the effects of an allergen are manifested. Such effects may be systemic or local in nature, depending on the route by which the antigen entered the body and the pattern of deposition of IgE and mast cells. Local manifestations generally occur on epithelial surfaces at the location at which the allergen entered the body.

Systemic effects can include anaphylaxis (anaphylactic shock), which is the result of an IgE-basophil response to circulating (intravascular) antigen.

One allergen of particular concern for many people is Antigen E or *Amb a* I, a poorly-defined constituent (or group of constituents) which is the major allergenic component(s) of short ragweed (*Ambrosia artemisilfolia* I. or *Ambrosia elatior*) pollen and the major cause of late summer hay fever in North America and Canada. Smith, J. J., et al., *Mol. Immun.* 25:355–364 (1988); King, T. P., et al., *Biochem.*, 3:458–468 (1964); King, T. P., *Adv. Immun.*, 23:77–105 (1976). It has been estimated that, on average, as much as 13% of the total serum IgE in ragweed-sensitive individuals is specific for *Amb a* I. Zeiss, C. R., et al., *J. Immun.*, 110:414–421 (1973). *Amb a* I has been claimed to be an acidic, 38,000 molecular weight, non-glycosylated protein which is cleaved during extraction and chromatographic isolation into two non-covalently associated chains: an alpha chain of 26,000 molecular weight and a beta chain of 12,000 molecular weight. Knox, R. B., et al., *Nature*, 255:1066–1068 (1970); Knox, R. B., and Heslop-Harrison, J., *J. Cell Sci.*, 6:1–27 (1970): King, T. P., *Adv. Immun.*, 23:77–105 (1976);/King, T. P., et al., *Archs Biochem. Biophys.*, 212:127–135 (1981). The two-chain and the single chain forms of *Amb a* I, which are both highly reactive with IgE, are allergenically and antigenically related. King, T. P., et al., *Biochemistry*, 3:458–468 (1964). It has been shown, however, that several physical and chemical modifications of *Amb a* I cause a marked loss of antigen and allergenic activity. King, T. P., et al., *Archs Biochem. Biophys.*, 212:127–135 (1981); King, T. P., et al., *Immunochemistry*, 11: 83–92 (1974).

Because ragweed pollen is the chief causative agent of late-summer hay fever in the eastern United States and Canada, it has been the subject of more studies by different laboratories than any other pollen allergen. King, T. P., *Adv. Immun.*, 23:77–105 (1976). Despite extensive study, the immunochemical definition of *Amb a* I is still far from complete. Smith and co-workers have begun characterization of the epitope structure of *Amb a* I, using a series of murine monoclonal antibodies raised against purified, native *Amb a* I. Three non-overlapping, non-repeating antigenic sites were defined (sites A, B, and C) and monoclonal antibodies directed to sites A and B together resulted in inhibition of 80% of human IgE binding to *Amb a* I. The reactivity of the monoclonal antibodies used was greatly diminished when *Amb a* I was physically or chemically modified. Olsen, Ph.D. thesis, University of North Carolina, Chapel Hill (1986); Olson, 3. R., and Klapper, D. G., *J. Immun.*, 136: 2109–2115 (1986). They indicated that the two sites (A and B) are conformationally dependent epitopes. That is, they are either single structures which lose their conformation during modification or composite structures made up of two or more discontinuous peptides which are proximal in the native allergen but separate once the allergen has been modified. Smith, J. J., et al., *Mol. Immun.*, 25:355–365 (1988).

Despite the considerable attention ragweed allergens have received, definition or characterization of the structures or component(s) of the allergen responsible for its adverse effects on people is far from complete and current desensitization therapy involves treatment with a complex, ill-defined extract of ragweed pollen.

SUMMARY OF THE INVENTION

The present invention relates to allergenic proteins or peptides from ragweed, DNAs encoding all or a portion of such allergenic proteins or peptides; to compositions containing such an allergens or portions of the allergen(s); and to methods of administering the allergen(s) or a portion thereof or a composition which includes the allergen(s) or portions thereof to reduce or prevent the adverse effects that exposure to the allergen normally has on ragweed-sensitive individuals (i.e., to desensitize individuals to the allergen or block the effects of the allergen). The present invention further relates to methods of diagnosing sensitivity to ragweed pollen.

It has now been shown that Antigen E or *Amb a* I is not a single protein but, rather, a family or families of proteins to which ragweed-sensitive individuals react. In particular, the present invention relates to DNA encoding an amino acid sequence or peptide present in allergenic proteins from ragweed pollen. It relates to DNA encoding all or a portion of the ragweed allergen *Amb a* I or Antigen E preparation which has been isolated. Such ragweed allergen preparations are heterogeneous in nature and may include, in addition to what is currently referred to as *Amb a* I or Antigen E, other ragweed components which are allergenic (i.e., cause the typical adverse effects observed in a ragweed-sensitive individual upon exposure to ragweed pollen). These may include, for example, what is referred to in the literature as Antigen K and referred to herein as *Amb a* II. The present invention also relates to DNAs encoding similar amino acid sequences (i.e., DNA encoding amino acid sequences of allergens) in types of ragweed other than short ragweed, such as giant ragweed and western ragweed.

BRIEF DESCRIPTION OF THE DRAWINGS

FIG. 2 is the nucleotide sequence of the DNA insert of UNC Clone 1 (referred to as *Amb a* IA) (SEQ ID NO:56), which was isolated from a λgt11 library by screening with monoclonal antibodies specific for components of an *Amb a* I preparation.

FIG. 3 is the nucleotide sequence of the DNA insert of UNC Clone 6 (referred to as *Amb a* IB) (SEQ ID NO:58), which was isolated from a λgt11 library by screening with monoclonal antibodies specific for components of an *Amb a* I preparation.

FIG. 4 is the nucleotide sequence of the DNA insert of UNC Clone 15 (referred to as *Amb a* IC) (SEQ ID NO:60), which was isolated from a λgt11 library by screening with monoclonal antibodies specific for components of an *Amb a* I preparation.

FIG. 5 is the nucleotide sequence of the cDNA insert of IPC Clone 1(SEQ ID NO:62), which was isolated from a λgt10 cDNA library using an oligonucleotide probe whose sequence was deduced from an amino acid sequence known to be present in the ragweed allergen preparation *Amb a* I. The location of the sequence from which the sequence of the oligonucleotide probe was deduced is underlined.

FIG. 6 is the nucleotide sequence of the cDNA insert of IPC Clone 5(SEQ ID NO:64), which was isolated from a λgt10 cDNA library using an oligonucleotide probe whose sequence was deduced from an amino acid sequence known to be present in the ragweed allergen preparation *Amb a* I. The location of the sequence from which the sequence of the oligonucleotide probe was deduced is underlined.

FIG. 7 is the nucleotide sequence of the cDNA insert of IPC Clone 6(SEQ ID NO:66); which was isolated from a λgt10 cDNA library using an oligonucleotide probe whose sequence was deduced from an amino acid sequence known to be present in the ragweed allergen preparation *Amb a* I. The location of the sequence from which the sequence of the oligonucleotide probe was deduced is underlined.

FIG. 11 is the nucleotide sequence (SEQ ID NO:71) and deduced amino acid sequence of a full length *Amb a* IA clone (related to UNC clone 1) (SEQ ID NO:72).

FIG. 12 is the nucleotide sequence (SEQ ID NO:73) and deduced amino acid sequence of a full length *Amb a* IB clone (related to UNC clone 6) (SEQ ID NO:74).

FIG. 13 is the nucleotide sequence (SEQ ID NO:75) and deduced amino acid sequence of a full length *Amb a* IC clone (related to UNC clone 15) (SEQ ID NO:76).

FIG. 14 is the nucleotide sequence (SEQ ID NO:77) and deduced amino acid sequence of a full length *Amb a* ID clone (SEQ ID NO:78).

FIG. 15 is the nucleotide sequence (SEQ ID NO:79) and deduced amino acid sequence of a full length *Amb a* II clone (SEQ ID NO:80).

FIG. 16 is the composite amino acid sequences of the *Amb a* I and *Amb a* II multigene family showing regions of similarity as well as regions of disagreements.

As a result of the work described herein, DNAs encoding proteins or peptides present in ragweed allergens have been identified and isolated and the amino acid sequence of the encoded product has been deduced. In addition, through the use of monoclonal antibodies specific for *Amb a* I or Antigen E, a protein has been obtained from an *Amb a* I preparation. This protein, referred to as affinity purified *Amb a* I, has been shown to have biological activity (human IgE binding ability and ability to bind rabbit *Amb a* I antisera) and, thus, is highly likely to be an allergen. It has also been shown to be encoded by a region of the nucleotide sequences present in two of the isolated DNAS.

Figure 1A:
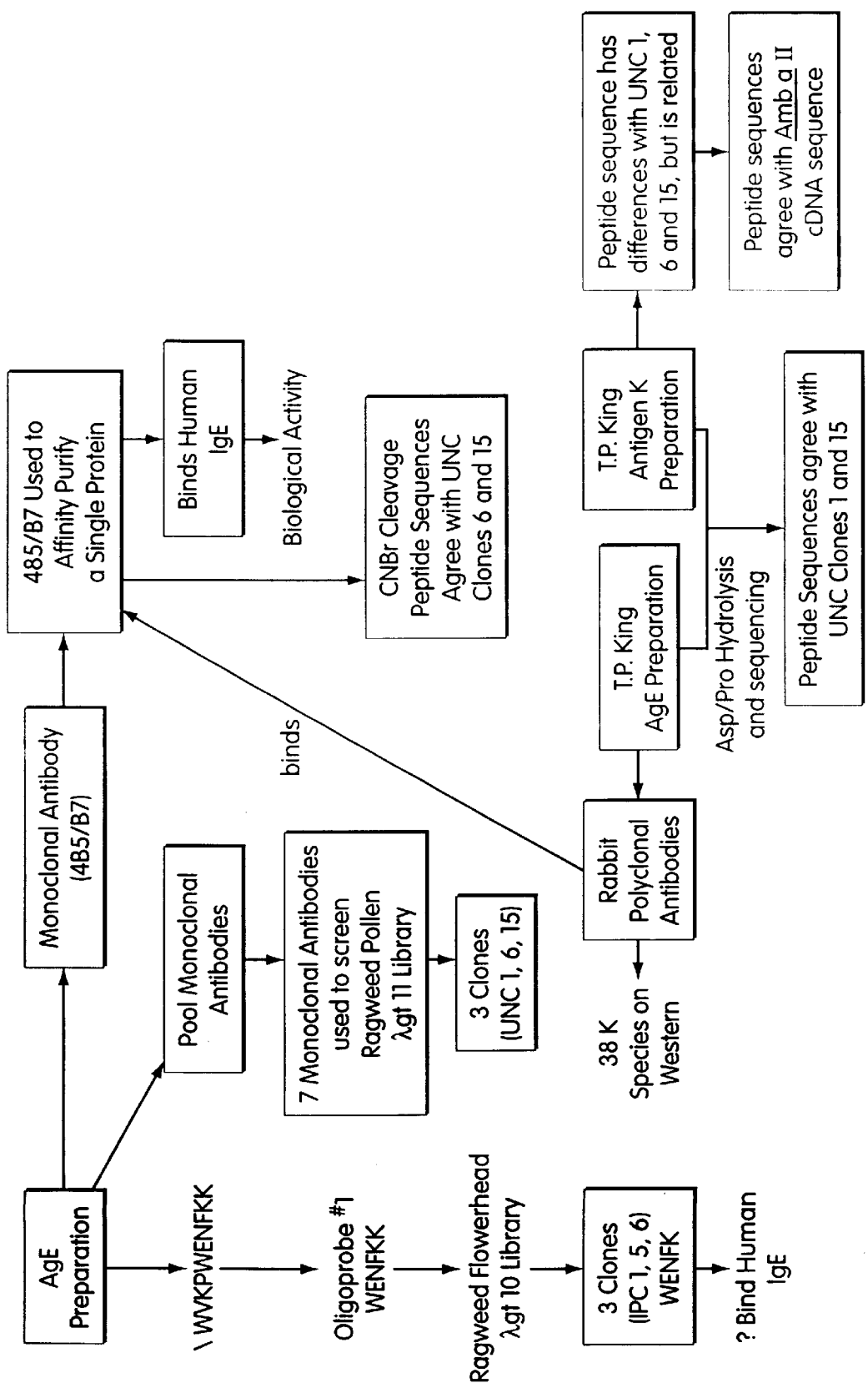
FIG. 1A is a schematic representation of screening of an *Amb a* I or Antigen E preparation, using monoclonal antibodies and oligoprobes.

The following is a description of several approaches which have been used to identify and isolate DNAs encoding proteins or peptides from *Amb a* I or Antigen E preparations, as well as to isolate from an *Amb a* I preparation a protein shown to have *Amb a* I activity. As represented in FIG. 1A, an *Amb a* I or Antigen E preparation, which was prepared from pollen extract by a method based on the method of T. P. King and co-workers, was produced. King, T. P. et al. *Arch. Bloch. and Biophys.*, 212:127–135 (1981). A panel of monoclonal antibodies produced by Klapper and co-workers was used to identify proteins in the preparation. Smith, J. J. et al., *Mol. Immun.*, 25:355–365 (1988). Sequences of several peptides from an Antigen E preparation were determined by conventional techniques.

The following sections describe: 1) use of a pool of these monoclonal antibodies (i.e., a pool of monoclonal antibodies reactive with *Amb a* I) to identify clones containing DNA inserts encoding the reactive product and 2) use of an oligonucleotide probe, constructed from an amino acid sequence present in the *Amb a* I preparation to identify clones containing DNA inserts encoding the amino acid sequence. Each approach resulted in identification of three clones containing DNA encoding an amino acid sequence present in the *Amb a* I or Antigen E preparation. The two sets of clones isolated as described below have been shown to be different from each other.

Use of Monoclonal Antibodies to Identify Clones Containing DNA Inserts Encoding Ragweed Protein A pool of seven monoclonal antibodies specifically reactive with components of the *Amb a* I preparation was used to screen a ragweed pollen λgt11 library, using a known method. Young, R. A. and R. W. Davis, *Proceedings of the National Academy of Sciences, USA*, 80: 1194–1198 (1983). This resulted in identification of three clones, initially designated UNC Clones 1, 6 and 15 and referred to herein as *Amb a* IA, IB and IC, respectively, which expressed a product recognized by at least one of the monoclonal antibodies in the panel. The nomenclature of cDNAs encoding the allergens *Amb a* I and *Amb a* II have been named according to the recommendations of the International Union of Immunological Societies Sub-Committee for Allergen Nomenclature (Marsh et-al., *Annals of Allergy*, 60:499–504 (1988)).

DNA isolated from the three reactive clones was sequenced, using the method of Sanger, F. et al. Sanger, F. et al., *Proc. Natl. Acad. Sci. USA*, 74:5463 (1977). The nucleotide sequences of the three clones are presented in FIGS. 2–4.

Using the partial cDNA sequences presented in FIGS. 2–4, cross-hybridization (as described in Example 2) and PCR methods (as described in Example 3) were used to isolate full-length cDNAs encoding *Amb a* IA (FIG. 11), *Amb a* IB (FIG. 12), *Amb a* IC (FIG. 13) and *Amb a* ID (FIG. 14).

In the course of DNA sequencing of cross-hybridizing cDNAs from a separately constructed λgt10 ragweed flowerhead library, a new cDNA was derived that shared sequence with *Amb a* II peptide sequence (FIG. 15 and FIG. 16). Construction of this library and isolation of the new cDEA are described in Example 2. The composite amino acid sequences of the *Amb a* I and *Amb a* II multigene family are shown in FIG. 16, with the regions of similarity and of disagreement represented. In FIG. 16, the sequence of *Amb a* I is given in standard one-letter code. Sequences for the other *Amb a* I family members are given relative to that of *Amb a* I, with only differences being shown. A dash indicates identity between the two sequences. An asterisk indicates a break in the sequence introduced to maintain maximal alignment. Amino acid numbering is based on the *Amb a* IB sequence. Wherever sequence polymorphism has been observed in a given family member, the dominant sequence is given in superscript and the minor sequence is given in subscript. Polymorphisms in a given family member occur as independent events, except for amino acids 183–189 of *Amb a* ID, in which the polymorphism occurs as a block.

Use of an Oligonucleotide Probe to Identify Clones Containing DNA Inserts Encoding Ragweed Protein As also represented in FIG. 1A, an amino acid sequence (SEQ ID NO:1) (WENFK) in the *Amb a* I preparation, which was identified and sequenced by conventional techniques, was used to deduce the sequence of an oligonucleotide probe (oligoprobe) encoding the amino acid sequence. The amino acid sequence used to deduce the oligonucleotide sequence was VWVKPWENFK (SEQ ID NO:2). A portion of that amino acid sequence (WENFK) was used to deduce the sequence of the oligoprobe, designated AGE#1. AGE#1 was used, as described in Example 1, to screen a cDNA library constructed in λgt10 using polyA$^+$ enriched RNA from pooled short ragweed flower heads. Screening with this oligoprobe resulted in identification of ten duplicated signals. These duplicated signals (clones) were subjected to a secondary screening with the same AGE #1 oligonucleotide probe. Three of the positives (referred to as secondary positives) were clearly detected in duplicate. The clones (designated IPC Clone 1, IPC Clone 5 and IPC Clone 6) identified in this manner were grown under appropriate conditions and verified as positive, by Southern blot analysis.

Figure 8:
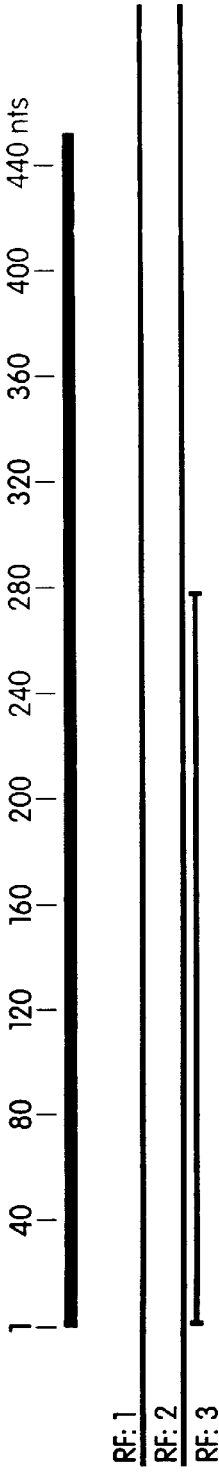
FIG. 8 is a schematic representation of open reading frame analysis of the DNA insert of IPC Clone 1.
Figure 9:
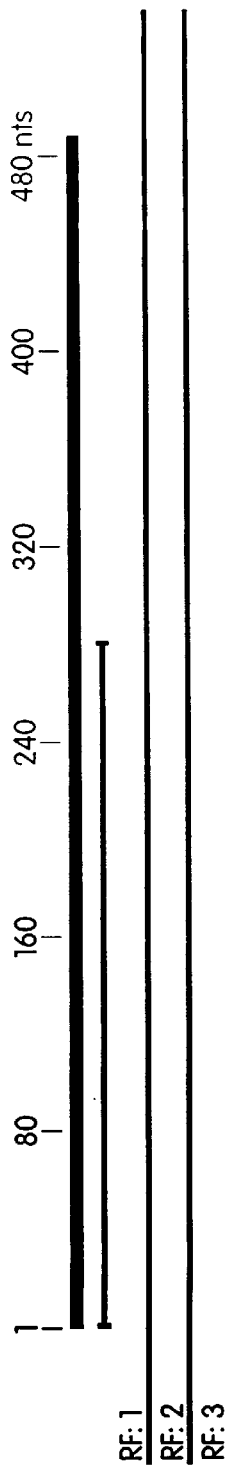
FIG. 9 is a schematic representation of open reading frame analysis of the DNA insert of IPC Clone 5.
Figure 10:
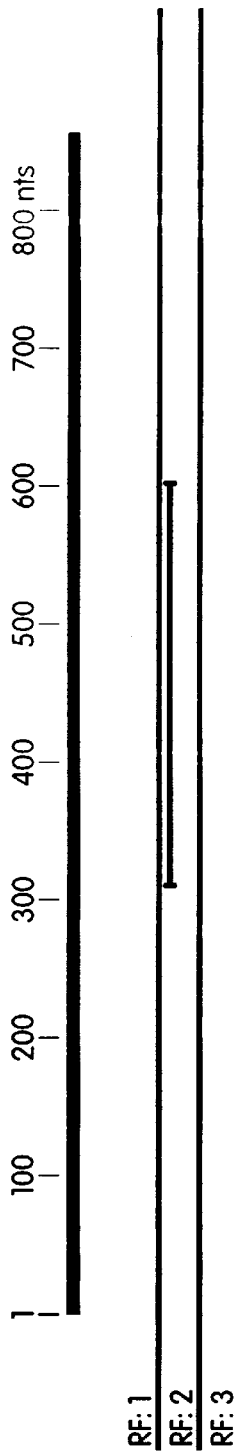
FIG. 10 is a schematic representation of open reading frame analysis of the DNA insert of IPC Clone 6.

The cDNA insert from each of the three clones was isolated and cloned into M13mpl8 and sequenced (FIGS. 5–7). The amino acid sequence was also deduced (FIGS. 8–10). Open reading frames in the sequenced cDNAs were examined (FIGS. 8–10) and the sequence (from which the sequence of the oligonucleotide probe had been deduced) was identified. That the cDNA inserts encode a portion of translated protein was supported by the fact that the surrounding amino acid sequence deduced from the DNA sequence (VWVKP) agreed with the amino acid sequence initially used to deduce the sequence of the oligoprobe (FIGS. 8–10). T cells from allergic patients could be stimulated by a synthetic peptide RAE4 (Table 5). The RAE4 sequence was deduced from IPC Clone 5 (FIG. 8).

As is evident from a comparison of the two "sets" of nucleotide sequences (i.e., set 1, which are the DNAs isolated through use of monoclonal antibodies, and set 2, which are the DNAs isolated through use of the oligoprobe), there is homology among sequences within a set (i.e., within FIGS. 2–4 and within FIGS. 5–7) but little similarity in sequences between sets.

Thus, it is apparent that the *Amb a* I or Antigen E preparation is heterogenous in nature and represents a family (or families) of proteins or that there is considerable polymorphism in *Amb a* I-encoding DNA. This is in contrast to present literature descriptions of *Amb a* I or Antigen E, which refer to Antigen E as a protein, rather than as a group or groups of allergenic proteins, present in ragweed pollen, to which ragweed-sensitive individuals respond.

Additional Demonstration of Isolation of Antigenic Peptides and DNAs of *Amb a* I Additional results further demonstrate that antigenic peptides of *Amb a* I and DNAs encoding them have been identified and isolated. As represented in FIG. 1A, a selected monoclonal antibody (designated 4B5/B7) which recognizes an *Amb a* I preparation unsubjected to denaturing conditions was used to affinity purify from pollen extract a single protein, which is referred to as affinity purified *Amb a* I. This was carried out, using known techniques, by producing the desired monoclonal antibody, isolating it in large quantities from ascites and immobilizing it on Sepharose (Pharmacia). Aqueous pollen extract was passed over the monoclonal antibody-containing column and a protein species was eluted. Antigen E isolated in this manner was shown, using both Western blot (FIG. 17) and ELISA techniques, to bind human IgE, thus demonstrating biological activity expected of an *Amb a* I protein or peptide.

Peptide sequence analysis was carried out as follows: Two peptides were isolated from partial tryptic digestion or cyanogen bromide (CNBr) cleavage of affinity purified *Amb a* I, respectively, and then subjected to peptide sequencing. Because the N-terminal of *Amb a* I is blocked, no amino acid sequence can be obtained from direct N-terminal protein sequence analysis. The result of the sequence analysis of the tryptic peptide demonstrated that the major portion of its amino acid sequence agreed with peptide sequence 45 to 77 encoded by the *Amb a* IA cDNA (Table 1). Table 1 is a comparison of the amino acid sequences of *Amb a* I protein, determined by protein sequence analysis, with the amino acid sequence deduced from *Amb a* I cDNA. The CNBr cleavage peptide sequencing demonstrated that the CNBr cleavage peptide was similar to the peptide sequence 171 to 184 encoded by the *Amb a* IA cDNA (Table 1).

Further peptide sequence analysis was performed from the protein cleavage mixture without isolating individual peptides. The techniques employed involved specific hydrolysis (with 70% formic acid or CNBr) of the putative Asp-Pro and Met-Pro bonds deduced from the cDNA sequences of *Amb a* I. Any primary amino groups were then blocked by reaction with o-phthalaldehyde prior to conventional sequencing from any available N-terminal proline residue.

TABLE 1

Amb a I PROTEIN SEQUENCES[a] COMPARED TO PROTEIN SEQUENCE DEDUCED FROM Amb a IA cDNA SEQUENCES

PARTIAL TRYPTIC DIGEST[b]

| | | | |
|---|---|---|---|
| Amb a IA | cDNA | SEQ ID NO:4 | 45   50   55   60   65   70   75   80   85   90<br>T S G A Y N I I D G C W R G K A D W A E N R K A L A D C A Q G F G K G T V G G K D G D I Y T V T |
| Amb a I[c] | MAJOR[d] | SEQ ID NO:5 | (T)S(G)A Y N I I D G C(W)R G K A D(W)A E N(R K)A L A D C A Q G F(G) |
| | MINOR[e] | SEQ ID NO:6 | (D)                                             (S R) |
| AgE[f] | | SEQ ID NO:7 | (T)S G A Y N I I D G C W R G K A D W A E N R K A L A D C A Q G F G K G T V G G K D G D I Y(T)V (T) |

CMBr CLEAVAGE

| | | | |
|---|---|---|---|
| Amb a IA | cDNA | SEQ ID NO:8 | 175       180       185<br>H D V K V N P G G L I K S N D G |
| Amb a I[g,h] | MAJOR | SEQ ID NO:9 | F D L K V N I G Q L I K(S)N |
| | MINOR | SEQ ID NO:10 | (A)P  N Y(I)P L    (N) |
| AgE[i] | | SEQ ID NO:11 | (E P Y K V )P G G L I K( )N( )G |
| | | | 280   285   290   295   300   305   310   315   320 |
| Amb a IA | cDNA | SEQ ID NO:12 | P R C R H G F F Q V V N N N Y D K W G S Y A I G G S A S P T I L S Q G N R F C A P D E R S |
| Amb a I[i] | MAJOR | SEQ ID NO:13 | P R C R H G F F Q V V N N N Y D R W G(S)Y A I G G S(A)P T I L S Q G N( )F(C)A P(D G Y) |
| | MINOR#1[j] | SEQ ID NO:14 |         F     I     F     D(H)           (N)                V |
| | MINOR#2[k] | SEQ ID NO:15 | P V L(T)P E(Q)S A(G M) |
| | MINOR#3[l] | SEQ ID NO:16 | T S G A Y N I I D G C W R G(K)A(D W)A |
| AgE | MAJOR | SEQ ID NO:17 | P R( )R H G P P Q V V N N N Y D(E W)G S: Y A I G G S A S P T I |
| | MINOR#1[m] | SEQ ID NO:18 | A(W)N(W)R(T E K)D L |
| | MINOR#2[n] | SEQ ID NO:19 | V(I)N L(p Q)E I(P V) |

TABLE 1-continued

Amb a I PROTEIN SEQUENCES[a] COMPARED TO PROTEIN SEQUENCE DEDUCED FROM Amb a IA cDNA SEQUENCES

70% FORMIC ACID HYDROLYSIS OF ASP-PRO PEPTIDE BOND[1]

```
                                  365       370       375       380       385       390       395
Amb a   IA   cDNA SEQ ID      P V L T P E Q S A G M I P A E P G E S A L S L T S S A G V L S C Q P G A P
             NO:20
Amba    I    MAJOR SEQ ID     P V L(N P) E () N A G M I Q A E (P G) E A
             NO:21
             MINOR° SEQ ID                          I
             NO:22
AgE SEQ ID NO:23              P V L T P E Q S A G M I P A E P G E S A L S L T S (S)A G V L ( C) Q P (G A) P
35KD[p,q] SEQ ID NO:24        P Y L T P V Q S A G M I P A E P G E A A I (K) L T S S
```

[a] the amino acids are presented in single letter code; uncertain residues are included in parentheses
[b] the peptides were separated by SDS-PAGE then Western blotted on PVDF membrane for sequence analysis
[c] IPC's affinity purified Amba I preparation
[d] major sequence determined in protein sequence analysis
[e] minor sequence determined in protein sequence analysis
[f] T. P. King's Amba I preparation
[g] the cleavage mixture was separated by SDS-PAGE then Western blotted on PVDF membrane
[h] the sequence is most similar to a IA cDNA sequence among all the cloned cDNA sequence
[i] the primary amine of the cleavage mixture was blocked by o-phtalaldehyde on the 7th step of sequence analysis
[j] similar to the a IIA cDNA sequence 277–315
[k] similar to the a IA cDNA sequence 361–371
[l] similar to the a IA cDNA sequence 45–63
[m] similar to the a IC cDNA sequence 338–347
[n] similar to the a IC cDNA sequence 126–135
[o] matches to a IC cDNA sequence 363
[p] IPC's Amb a I preparation with molecular weight of 35,000 dalton
[q] matches to a IC cDNA sequence 361–386

Results of these assessment (shown in Table 1) demonstrated that two peptide sequences determined from the affinity purified *Amb a* I preparation agreed with that encoded by two portions of *Amb a* IA DNA sequence (277–321 or 361–397). The minor sequences detected in the peptide sequence analysis also corresponded to a portion of peptide sequence encoded by cDNA's of *Amb a* I or *Amb a* II. The above peptide sequence analyses provided strong support that *Amb a* I or Antigen E-encoding DNA had been isolated.

An Antigen E preparation obtained from Dr. T. P. King was also subjected to peptide sequencing. The same peptide sequencing techniques were employed. Four peptides sequences were identified which agreed with the same four segments of peptide sequence encoded by *Amb a* IA DNA (45–92, 171–186, 277–321 and 361–397 in Table 1). This provided additional proof that *Amb a* I or Antigen E-encoding DNA had been isolated.

The same techniques were used with purified Antigen K (*Amb a* II) from Dr. T. P. King. Results demonstrated that two peptide sequences agreed with two portions of peptide sequence encoded by DNA of *Amb a* II (Table 2, see Example 2; FIG. 15). Table 2 is a comparison of the amino acid sequences of *Amb a* II protein, determined by protein sequence analysis, with the amino acid sequence deduced from *Amb a* II cDNA. This finding provided support that ragweed pollen allergen encoding DNA had been isolated.

TABLE 2

Amb a II PROTEIN SEQUENCES[a] COMPARED TO PROTEIN SEQUENCE DEDUCED FROM Amb a IIA cDNA SEQUENCE

CNBr CLEAVAGE[b]

```
                                           280       285       290       295       300       305       310       315       320
Amb a IIA cDNA       SEQ ID NO:25   P R C R F G F F Q I V N N F Y D R W D E Y A I G G S S N P T I L S Q G N K F V A P D F I Y
AgK[c]     MAJOR[d]  SEQ ID NO:26   P R( )R F G F F Q I V N N F Y D R W D(H)Y A I G G S S N P T I L S Q G N(R)F V A P(D  )I(Y)
           MINOR[e,f] SEQ ID NO:27  P V L T P E Q N A G M
Amb a II[g]          SEQ ID NO:28   P(R  R)F G F F Q I V N N F Y D
```

70% FORMIC ACID HYDROLYSIS OF ASP-PRO PEPTIDE BOND[b]

```
                                       365       370       375       380       385       390       395
Amb a IIA cDNA     SEQ ID NO:29   P V L T A E Q N A G M M Q A E P G D M V P Q L T M N A G V L T C S P G A P
AgK     —          SEQ ID NO:30   P V L T A E Q N A G M M Q A E P G D M V P Q L T M N A(G)V(L     S)P G A P
Anb a II[g] MAJOR  SEQ ID NO:31   P V L T A E Q N A G M M Q A E P G D M V P Q L T M N A G V L T(C)S P G A P
        MINOR[h]   SEQ ID NO:32          P           I P          E S A L S        S              (S)
```

[a] the amino acids are presented in single letter code; uncertain residues are included in parentheses
[b] o-phthalaldehyde is reacted with peptide mixture prior to conventional peptide sequence analysis
[c] T. P. King's Amb a II preparation
[d] major sequence determined in protein sequence analysis
[e] minor sequence determined in protein sequence analysis
[f] matches the a IIA cDNA sequence 361–371
[g] matches the a IIA cDNA sequence 361–371
[h] matches to a IA cDNA sequence 361–397

It has been previously reported that Amb a I and Amb a II share some antigenic determinants using rabbit and human antisera (King, T. P., Adv. Immun., 23:77–105 (1976)). However, the exact relationship between the two antigens, until the present invention, has remained unclear. King and colleagues have also reported that different isoforms of antigen E and K (Amb a I and Amb a II) can be isolated by ion-exchange chromatography (King, T. P. et al., Ach. Biochem. Biophys., 212:127–135 (1981)). The different isoforms described, designated A, B, C and D, were interpreted to be produced by limited proteolysis of the intact Amb a I and Amb a II species. It should be noted that these isoforms, designated A, B, C, etc., have no direct relationship with the nomenclature outlined in this invention (i.e., Amb a IA, Amb a IB, etc.).

A 35,000 dalton species coprecipitates from ragweed pollen extract with Amb a II in 45% saturation of ammonium sulfate. Most of these proteins are shown to be agregated by gel filtration chromatography. Some monomeric forms of these proteins were separated from Amb a II by ion exchange chromatography. The sequencing technique, which involved 70% formic acid hydrolysis of putative Asp-Pro bound and o-phthalaldehyde blocking of primary amino groups, demonstrated that the predominant protein corresponds to that encoded by the DNA sequence of Amb a IC. This peptide sequence is referred to as 35 kD in Table 1. This result provided additional support that Amb a I proteins are heterogeneous in nature and are encoded by closely related DNA's.

Figure 17:
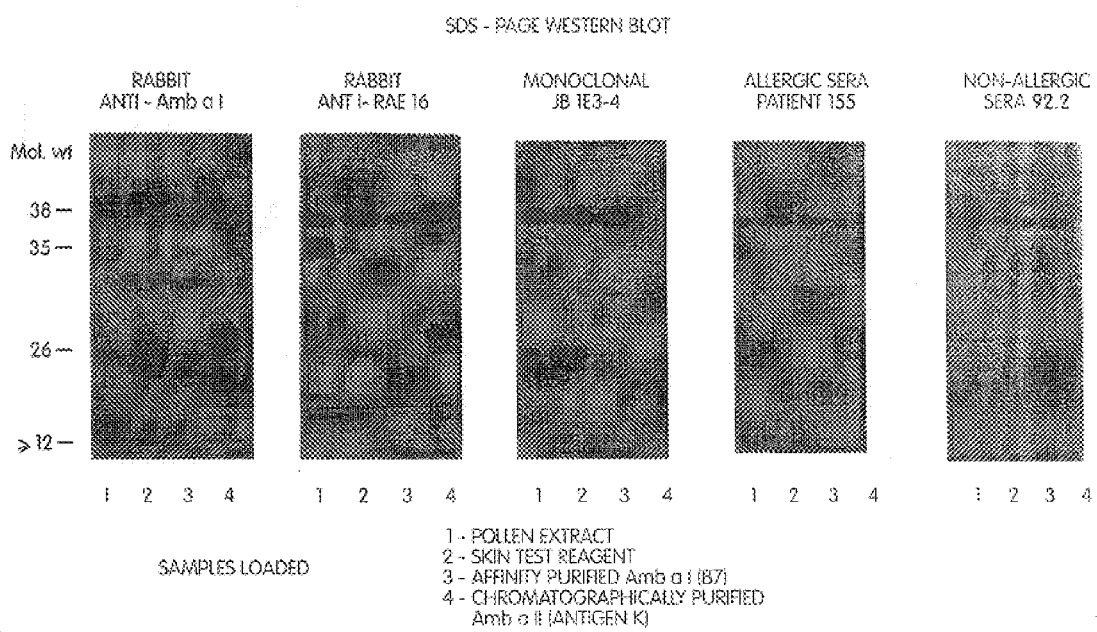
FIG. 17 is a photograph of a Western blot of affinity purified *Amb a* I treated with rabbit anti-*Amb a* I polyclonal antibody, JB1E3-4 anti-*Amb a* I monoclonal antibody or ragweed allergic patient sera.
Figure 18:
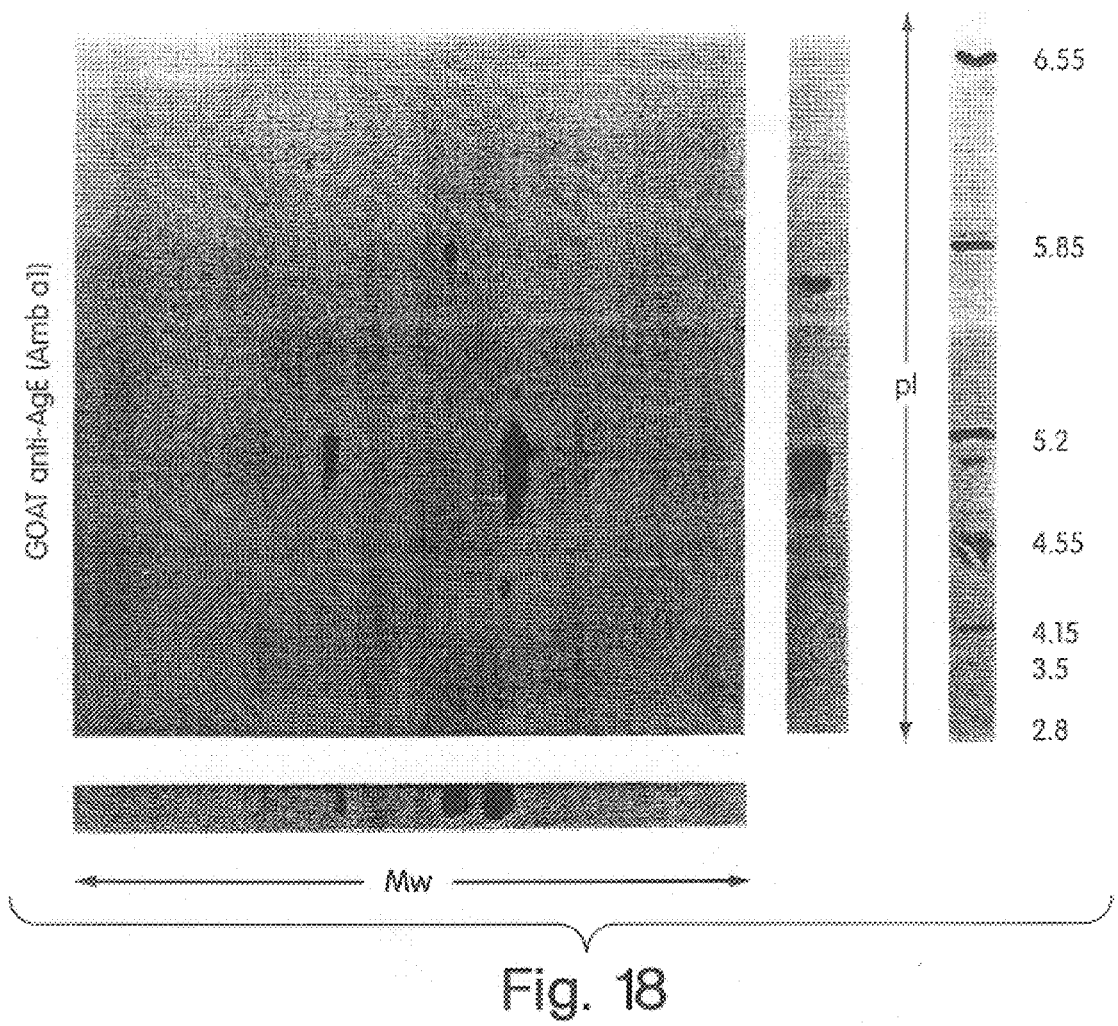
FIG. 18 is a photograph of a two dimensional gel of an aqueous extract of short ragweed pollen, separated on the basis of size and charge and stained with T. P. King's antibody, which recognizes Interrelationships among DNAs and proteins or peptides identified and isolated using the approaches described in the following section have been demonstrated. For ease of presentation, the several approaches used are represented schematically in FIGS. 1A and 1B, to which reference is made in the following discussion.

As is also represented in FIG. 1A, rabbit polyclonal antibodies were produced using the King Antigen E preparation. These antibodies were shown to identify a 38kd protein species on a Western blot of pollen extracts (FIG. 17). A two-dimensional gel of ragweed pollen extract, electrophoresed in one dimension on the basis of charge and in the other dimension on the basis of size and treated with goat anti-Amb antibodies is shown in FIG. 18 Results demonstrate binding to several proteins present in ragweed pollen extract with a relative molecular weight of 38 kD, corresponding to differently charged forms of what was formerly referred to as Amb a I protein. These antibodies were also shown, using a similar technique, to bind to the affinity purified Amb a I described previously (FIG. 17).

It is clear from the antibody reactivity that the 4B5/B7 affinity purified Amb a I has a recognition pattern similar to that of the Amb a I of pollen and skin test reagent with both rabbit polyclonal anti-Amb a I and JB1E3-4 anti-Amb a I monoclonal antibody (FIG. 17). It also has readily detectable IgE reactivity on a Western blot (FIG. 17; patient number 155). It is also clear that chromatographically purified Amb a II (Antigen K) has cross-reactive B-cell epitopes with the affinity purified Amb a I (FIG. 17; anti-Amb a I polyclonal).

As a result of the work described herein, cDNAs encoding allergenic peptides of proteins from a preparation of Amb a I, the major human allergen of ragweed and a preparation ofrAmb a II). have been cloned, isolated and sequenced; the encoded amino acid sequences (of the allergen(s)) have been deduced and peptides derived from Amb a I and Amb a II have been identified and isolated.

Figure 19:
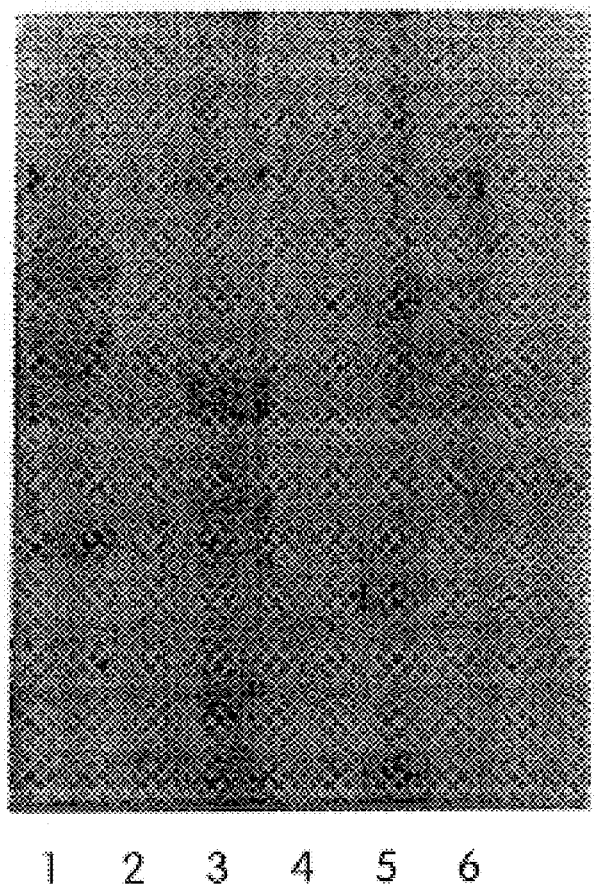
Figure 20:
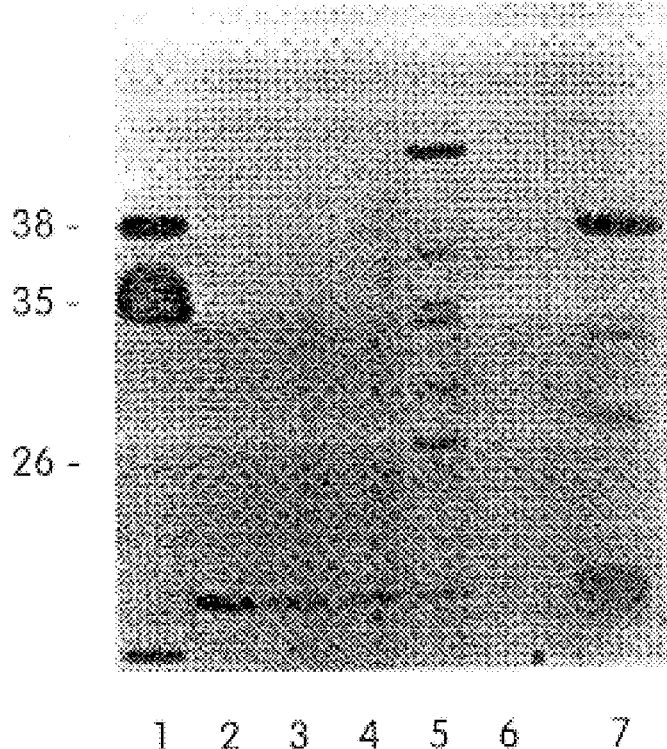

Furthermore, full-length and truncated cDNAs encoding several members of the Amb a I multigene family, as well as Amb a II, were cloned in-frame into the expression vector pTrc99 (Amann et-al. Gene, 69: 301–315, (1988)) and transformed into the JM109 host. Expression of recombinant Amb a I and Amb a II protein was induced by lmM isopropyl-β-D-thiogalactopyranoside, cells were harvested, lysozyme treated, sonicated and insoluble inclusion bodies recovered by a low speed centrifugation. Recombinant Amb a I and Amb a II protein present in the recovered pellet was solubilized in buffer containing 8M urea, 50 mM Tris HCl pH8.0, 50 mM NaCl, 1 mM EDTA, lmM dithiothreitol, lmM phenylmethylsulfonyl fluoride. After solubilization, the crude urea lysate was dialyzed at 4° C. against PBS. The expressed recombinant Amb a I and Amb a II proteins were Western blotted and results are shown in FIGS. 19 and 20. Results demonstrate (FIG. 19) that goat anti-Amb a I antibody binds specifically to several forms of Amb a I (A, B and C), as well as to Amb a II (antigen K). This antigenic cross-reactivity is consistent with the observed sequence homology of the cDNAs (see FIG. 16). They further demonstrate (FIG. 20) that allergic human IgE binds specifically to some members of the Amb a I multigene family. In the case of patient #295, Amb a IA (full-length) and Amb a IC are bound specifically by IgE to a far greater extent than Amb a IB or Amb a II. A high level of variability in the patterns of IgE binding is seen (Table 3 and data not shown), suggesting that different patients respond to the different Amb a I proteins to different extents.

TABLE 3

SUMMARIZED WESTERN BLOT DATA*

| Patient | Pollen | Antigen IA (t) | IA | IB | IC | IIA |
|---------|--------|----------------|-----|-----|-----|-----|
| 151 | + | – | + | – | + | + |
| 222 | +– | +– | +– | +– | +– | + |
| 291 | +++ | + | – | +++ | +– | |
| 295 | +++ | + | +++ | + | +++ | – |
| 296 | ++ | | ++ | | ++ | – |

– no signal over background
+– barely discernable over background
+ clearly positive
++ strongly positive
+++ highly positive
*selected from the total of ten patients screened to date.

An analysis of SDS-PAGE Western blot of IgE binding to several recombinant forms of Amb a I and Amb a II has demonstrated that there is considerable variation in the pattern observed with different patients. Of the ten ragweed allergic patients examined, all possess serum IgE that binds to at least one recombinant Amb a I or Amb a II, with some patient's IgE binding several different recombinant species (summarized in Table 3). Comparison of human IgE binding to recombinant Amb a I and Amb a II proteins with anti-peptide and monoclonal anti-Amb a I antibodies have provided data consistent with the conclusion that the N-terminal portion (historically referred to as the β-region) of Amb a IA includes the major IgE epitape(s). This data (Table 3) is based on the observation that Amb a IA(t) (truncated Amb a IA; amino acid 70–398) binds ragweed allergic patient IgE less well than the full-length Amb a IA (amino acid 10–398). It is expected that the other Amb a I and Amb a II forms possess the same IgE binding properties (see FIG. 20, for example).

T cells from patients allergic to ragweed, previously stimulated with a mixed ragweed pollen extract, can recognize and proliferate in response to pollen extract, ragweed skin test reagent (RWST), affinity purified Amb a I protein and crude bacterial lysates containing recombinant Amb a I gene products IA, IB and It (Table 4). T cells from these patients do not proliferate in the presence of an equivalent amount of control bacterial lysate, JM109. These results demonstrate that each gene product can stimulate some T cell reactivity. The use of crude bacterial lysates as antigens precludes a firm conclusion from the negative responses, since the relative levels of recombinant proteins in lysate have not been determined.

TABLE 4

STIMULATORY RESPONSE[a] OF THE HUMAN T CELL TO
RECOMBINANT RAGWEED PROTEINS

| PATIENT # | POLLEN | RWST[b] | Amb a I[c] | Amb a IB LYSATE | Amb a IC LYSATE | Amb a IA (t) LYSATE | Amb a IA LYSATE | JM109 LYSATE |
|---|---|---|---|---|---|---|---|---|
| 151 | 2° | +++ | + | (+) | + | + | + | (+) | — |
| 222 | 2° | +++ | +++ | +++ | - | ++ | ++ | ++ | — |
| 274 | 2° | ++ | ++ | ++ | + | ++ | | | — |
| 295 | 2° | +++ | | | + | + | + | | — |
| 296 | 2° | +++ | +++ | +++ | +++ | +++ | +++ | | — |
| 316 | 2° | +++ | +++ | +++ | ++ | +++ | +++ | | — |
| 319 | 2° | +++ | +++ | ++ | (+) | +++ | +++ | | — |
| 320 | 2° | ++ | ++ | +++ | + | - | ++ | | — |
| 321 | 2° | +++ | +++ | + | ++ | + | ++ | | — |

[a]proliferation responses as compared to medium control:
(+) 2 fold
+ 2–4 fold
++ 4–10 fold
+++ <10 fold
[b]ragweed skin test reagent from Hollister-Stier
[c]affinity purified Amb a I Uses of the Subject Allergenic Proteins/Peptides and DNA Encoding Same The materials resulting from the work described herein, as well as compositions containing these materials, can be used in methods of diagnosing, treating and preventing ragweed allergy. In addition, the cDNA (or the mRNA from which it was transcribed) can be used to identify similar sequences in any variety or type of ragweed and, thus, to identify or "pull out" sequences which have sufficient homology to hybridize to, for example, DNA from short ragweed pollen. This can be carried out, for example, under conditions of low stringency; those sequences which have sufficient homology (generally greater than 40%) can be selected for further assessment using the method described herein. Alternatively, high stringency conditions can be used.

In this manner, DNA of the present invention can be used to identify, in other types of ragweed (such as giant ragweed or Western ragweed) sequences encoding peptides having amino acid sequences similar to that of *Amb a* I and, thus, to identify allergens in such other types of ragweed. Thus, the present invention includes not only *Amb a* I and other ragweed allergens (e.g., *Amb a* II or Antigen K) encoded by the present DNA sequences, but also other ragweed allergens encoded by DNA which hybridizes to DNA of the present invention.

Proteins or peptides encoded by the cDNA of the present invention can be used, for example, as "purified" allergens. Such purified allergens are useful in the standardization of allergen extracts which are key reagents for the diagnosis and treatment of ragweed allergy. Furthermore, by using peptides based on the sequences listed in FIGS. 2 through 16, anti-peptide antisera or monoclonal antibodies can be made using standard methods. Such reagents can be specifically directed against individual isoforms of *Amb a* I or *Amb a* II (i.e., directed against divergent regions/epitopes of the molecule) or can be specific for all forms of *Amb a* I or *Amb a* II (i.e., directed against common sequences/epitopes). These sera or monoclonal antibodies, directed against *Amb a* I or *Amb a* II, can be used to standardize allergen extracts. One such monospecific anti-peptide antisera has already been successfully produced. This rabbit antisera, directed against an *Amb a* II sequence (amino acid 326–338; designated RAE 50.K with the sequence: CLRTGAQEPEWMT (SEQ ID NO:33)) binds specifically on Western blots to recombinant *Amb a* II but not *Amb a* IA, B or C (data not shown).

Through use of the peptides of the present invention, allergen preparations of consistent, well-defined composition and biological activity can be made and administered for therapeutic purposes (e.g., to modify the allergic response of a ragweed-sensitive individual to a ragweed pollen). Such peptides or proteins (or modified versions thereof, such as are described below) may, for example, modify B-cell response, to a ragweed allergen, T-cell response to a ragweed allergen or both responses. Purified allergens can also be used to study the mechanism of immunotherapy of ragweed allergy and to design modified derivatives or analogues which are more useful in immunotherapy than are the unmodified ("naturally-occurring") peptides.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of a peptide derived from the DNA insert of Clone *Amb a* IA, Clone *Amb a* IB, Clone *Amb a* IC, *Amb a* II, IPC Clone 1, IPC Clone 5 or IPC Clone 6, or their full-length cDNAs) or a modified peptide or peptide analogue (e.g., a peptide in which the amino acid sequence has been altered to modify immunogenicity and/or reduce allergenicity or to which a component has been added for the same purpose). For example, *Amb a* I peptides can be modified using the polyethylene glycol method of A. Sehon and co-workers.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, oral administration, inhalation, transdermal application or rectal administration. Using the structural information now available, it is possible to design a ragweed pollen peptide which, when administered to a ragweed-sensitive individual in sufficient quantities, will modify the individual's allergic response to a ragweed allergen. This can be done, for example, by examining the structures of the ragweed proteins, producing peptides to be examined for their ability to influence B-cell and/or T-cell responses in ragweed-sensitive individuals and selecting appropriate epitopes recognized by the cells. Synthetic amino acid sequences which mimic those of the epitopes and which are capable of down regulating allergic response to ragweed allergen can also be used. Proteins, peptides or antibodies of the present invention can also be used for detecting and diagnosing ragweed allergy. For example, by combining blood or blood products obtained from an individual to be assessed for sensitivity to ragweed allergen with an isolated allergenic peptide of ragweed pollen, under conditions appropriate for binding of components (e.g., antibodies, T cells, B cells) in the blood with the peptide and determining the extent to which such binding occurs.

It is now also possible to design an agent or a drug capable of blocking or inhibiting the ability of ragweed allergens to induce an allergic reaction in ragweed-sensitive individuals. Such agents could be designed, for example, in such a manner that they would bind to relevant anti-ragweed IgEs, thus preventing IgE-allergen binding and subsequent mast cell degranulation. Alternatively, such agents could bind to cellular components of the immune system, resulting in suppression or desensitization of the allergic response to ragweed allergens. A non-restrictive example of this is the use of appropriate B- and T-cell epitope peptidesr, or modifications thereof, based on the cDNA/protein structures of the present invention to suppress the allergic response to ragweed allergens. This can be carried out by defining the structures of B- and T-cell epitope peptides which affect B- and T-cell function in in vitro studies with blood cells from ragweed-sensitive individuals.

The cDNA encoding an allergenic protein or peptide from ragweed can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., *Amb a* I protein or peptide). Cells are cultured under conditions appropriate for expression of the DNA insert (production of the encoded protein or peptide). The expressed product is then recovered, using known techniques. Alternatively, the *Amb a* I allergen or portion thereof can be synthesized using known mechanical or chemical techniques. As used herein, the term protein or peptide refers to proteins or peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of a sequence represented herein (See FIGS. 2–16), or their functional equivalents. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 2–16 hybridizes and/or which encodes a product (e.g., a polypeptide or peptide) having the same functional characteristics of the product encoded by the sequence (or corresponding sequence portion) of FIGS. 2–16. Whether a functional equivalent must meet one or both criteria will depend on its use (e.g., if it is to be used only as an oligoprobe, it need meet only the first criterion and if it is to be used to produce an *Amb a* I allergen, it need only meet the second criterion).

Antibodies against *Amb a* I peptides can be used to isolate additional components of ragweed allergens which can be used for further definition of the characteristics of the *Amb a* I family. Furthermore, anti-peptide sera or monoclonal antibodies directed against *Amb a* I and/or *Amb a* II can be used to standardize and define the content of ragweed skin test reagents (RWST). This use would include RWST other than those derived from *Ambrosia artemisilfolia* I. (e.g., Western, Desert, Giant ragweeds, etc.).

The structural information now available (e.g., DNA, protein/peptide sequences) can alto be used to identify or define T cell epitope peptides and/or B cell epitope peptides which are of importance in ragweed allergic reactions and to elucidate the mediators or mechanisms (e.g., interleukin-2, interleukin-4, gamma interferon) by which these reactions occur. This knowledge should make it possible to design peptide-based ragweed therapeutic agents or drugs which can be used to modulate these responses.

The present invention will now be further illustrated by the following Examples, which are not intended to be limiting in any way.

EXAMPLE 1

Screening of a λgt11cDNA Library Using an Oligonucleotide Probe

PolyA$^+$ enriched RNA extracted from pooled short ragweed flower heads was used to construct a cDNA library in the vector λgt10. The cDNA library was constructed using the Gubler and Hoffman method and the kit supplied by Amersham. Gubler, U. and B. J. Hoffman, *Gene*, 25:263 (1983). A library of $1.4\times10^5$ plaques constituting approximately $7\times10^4$ recombinants was constructed. This library was plated out and screened according to the method of Benton and Davis. Benton, W. D. and R. W. Davis, *Science*, 196:180 (1977).

Screening of the cDNA Library:

An amino acid sequence (VWVKPWENFKK (SEQ ID NO:34)), thought to be derived from antigen E was used to deduce an oligonucleotide probe with which to screen the cDNA library.

| | | | | | | | |
|---|---|---|---|---|---|---|---|
| Amino Acid Sequence | W | E | N | F | K | K | (SEQ ID NO: 35) |
| Deduced Nucleotide | TGG | GAA | AAT | TTC | AAA | AAA | (SEQ ID NO: 36) |
| Sequence | | G | C | T | G | G | (SEQ ID NO: 37) |

AGE #1 OLIGOPROBE

The AGE #1 oligoprobe was end-labeled with P and used to probe 70,000 recombinants using the hybridization conditions listed below:

| | |
|---|---|
| 6 × SSC<br>1 × Denhardt's<br>50 μg/ml *E. coli* tRNA | at 30 degrees C. for 22 hours |

Ten duplicated signals were detected and these clones were subjected to a secondary screening with the same AGE #1 oligoprobe. It was subsequently discovered that the correct amino acid sequence is WENFKE (SEQ ID NO:38).

A summary of the cloning procedure is listed below:

Primary Screen: 70,000 plaques $^{32}$P—AGE #1 oligoprobe

Numerous spots with 10 signals were clearly seen on duplicated filters.

Secondary Screen:

Plaques from the 10 duplicate signals were picked and plated out at low density and rescreened using methods outlined in Clontech's catalog.

Tertiary Screening:

Three secondary positives numbered #1, #5, and #6 were clearly detected in duplicate. Each clone was grown up and verified as positive by Southern Blot analysis.

Sequencing of Positive Clones:

cDNA inserts from each of the clones were isolated then cloned into M13mp18. Each clone was sequenced using the Sanger dideoxy method and the deduced amino acid sequence was determined. Sanger, F. et al., *Proc. Natl. Acad. Sci. USA*, 74:5463 (1977).

Identification of WENFKK and Surrounding Sequence:

The DNA sequences of the cDNA clones are presented in FIGS. 5, 6 and 7. The cDNA clones are not full-length and are less than 500 nucleotides in length. The AGE#1 oligoprobe nucleotide sequence is underlined in FIGS. 5, 6 and 7. Open reading frames in the sequenced cDNAs were examined and are presented in FIGS. 8, 9 and 10. The translated amino acid sequence (WENFK) used to deduce AGE#1 oligoprobe sequence is underlined as well as the N-terminal surrounding sequence (VWVKPWENFK (SEQ ID NO:2); see FIGS. 8, 9 and 10). IPC clones 1 and 5 disagree with the amino acid sequence at only one out of ten residues (i.e., L instead of P). The presence of the correct surrounding sequence (VWVKP (SEQ ID NO:39)) verifies that the cDNAs encode protein in pollen. Furthermore, a synthetic peptide based on the cDNA sequence designated RAE 4, which has the sequence EFPILGGITEVKDNDNSVDFC (SEQ ID NO:40), stimulates ragweed allergic patient T cells, in in-vitro proliferation assays (see Table 5 and sequences in FIGS. 8, 9 and 10).

EXAMPLE 2

Cross-hybridization Methods Used to Obtain full-Length cDNAs

Antigen E is reported to be a protein of approximately 38,000 molecular weight and consequently a full-length cDNA encoding this protein must be at least 1.1 Kb in length (King, T. P et al., *Arch. Biochem. Biophys.*, 212:127 (1981)).

Consequently, IPC clones 1, 5 and 6 as well as UNC clones 1, 6 and 15 (designated *Amb a* IA, IB and IC, respectively) are not full-length.

Figure 1B:
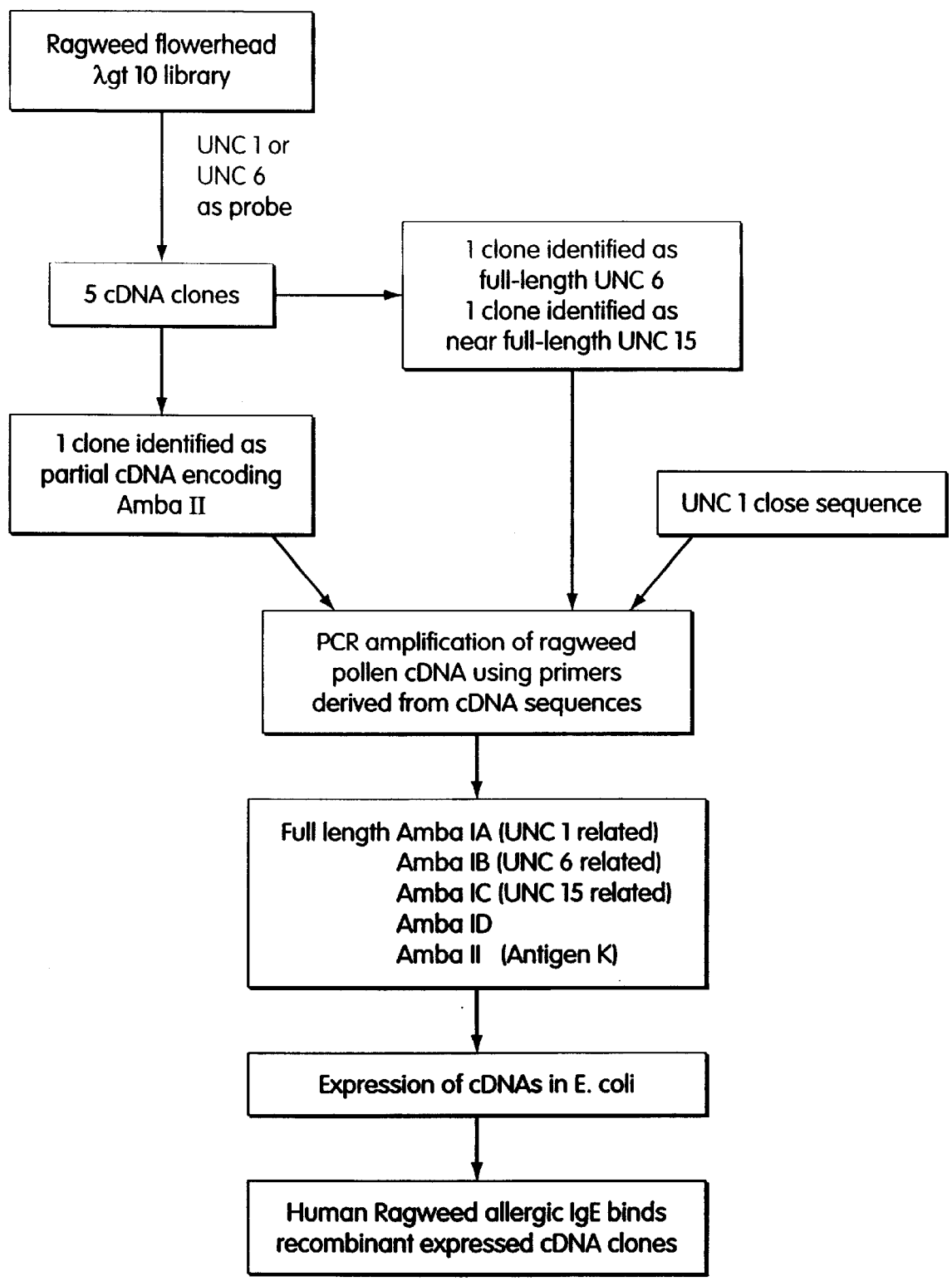
FIG. 1B is a schematic representation of screening of a ragweed flowerhead λgt10 library. It also illustrates the use of cross-hybridization and polymerase chain reaction (PCR) methods to obtain full-length cDNA clones encoding *Amb a* I and *Amb a* II.

In order to isolate full-length clones, nick-translated $^{32}$p-labelled *Amb a* I cDNA probes were used to screen the ragweed flowerhead λgt10 (see Example 1) and the ragweed pollen λgt11 library using standard methods (Maniatis et al., *Molecular Cloning*, Cold Spring Harbor Laboratory, (1982)). Full-length or near full-length cDNAs encoding *Amb a* IB (FIGS. 12 and 16) and *Amb a* IC (FIGS. 13 and 16) were isolated using this method (FIG. 1B). One cross-hybridizing cDNA clone (called K6-5), which has an open reading frame of approximately 145 amino acids (amino acids 253–398; FIG. 15), was found to be significantly divergent from the previously isolated *Amb a* IA, *Amb a* IB, *Amb a* IC and *Amb a* ID and showed complete agreement (Table 2) with a peptide sequence derived from conventionally purified antigen K (a gift from T. P. King, New York). Consequently, this partial cDNA was designated as *Amb a* II (see FIG. 15 and below).

EXAMPLE 3

Polymerase Chain Reaction (PCR) Methods Used to Obtain Full-length cDNAs

PCR methods can be successfully used to isolate both rare message cDNA as well as genomic clones of known sequence (Mullis et al., *Cold Spring Harbor Symposium Quant. Biol.*, 51:263–273 (1986)). 5' and 3' oligonucleotide primers were synthesized and used in a PCR experiment with ragweed pollen cDNA serving as template. The 5' primers were deduced from N-terminal conserved regions of *Amb a* IB (FIG. 12) and *Amb a* IC (FIG. 13). The 3' primers were deduced from *Amb a* IA specific (UNC clone 1, designated *Amb a* IA, FIG. 2) and *Amb a* II specific (clone K6-5, partial 3' sequence of FIG. 15) non-coding strand sequences at the 3' end of the cDNA. A third 3' primer used to PCR clone *Amb a* ID was derived from a conserved region of the C-terminal end of *Amb a* IA, B and C (amino-acids 395–398 corresponding to GAPC.stop). The oligonucleotide primers used to amplify and clone *Amb a* IA, *Amb a* ID and *Amb a* II cDNAs are listed below:

N-terminal primers used to produce full-length *Amb a* IA and *Amb a* II (amino acids 10–15)

|      | ECORI | L | Y | F | T | L | A | (SEQ ID NO: 41) |
|------|-------|---|---|---|---|---|---|-----------------|
| IG38 | GGGAATTC | TTG | TAT | TTT | ACC | TTA | GC | (SEQ ID NO: 42) |
| 5'   |       |   |   |   |   |   | 3' |                 |

N-terminal primer used to produce truncated *Amb a* IA and *Amb a* II (amino acids 70–75)

|      | ECORI | D | G | A | Q | G | F | (SEQ ID NO: 43) |
|------|-------|---|---|---|---|---|---|-----------------|
| IG33 | GGGAATTG | GAG | TGT | GCC | CAA | GGT | TTT G | (SEQ ID NO: 44) |

C-terminal primer used to produce full-length and truncated *Amb a* IA (12–29 nucleotides of the noncoding strand 3' of the TAA stop codon; see FIG. 2).

Pst I

IG32

5' GGGCTGCAG TCATTATAAGTGCTTAGT3' (SEQ ID NO:45)

C-terminal primer used to produce full-length *Amb a* ID (corresponding to the C-terminal conserved GAPC encoding region). The primer is of the non-coding strand and includes the stop codon and an artificially introduced Pst I cloning site (see FIG. 15).

Pst I
IG49

5' GGGCTGCAG TGC TTA GCA AGG TGC TCC3' (SEQ ID NO:46)

C-terminal primer used to produce full-length and truncated Amb a II (44–76 nucleotides of the noncoding strand 3' of the TAA stop codon; see FIG. 15).

Pst I
ASK2

5' GGCCTGCAG CGT GTC CAA ATC TAA TCA AAT GAA CAC TTA TGG3' (SEQ ID NO:47)

First strand cDNA was synthesized from 1 µg RNA with the cDNA synthesis system plus kit (Amersham) using poly dT as primer. This single stranded cDNA was amplified using sets of primers (IG38 plus IG32: IG33 plus IG32; IG38 plus IG49; IG38 plus AgK2; IG33 plus AgK2) according to methods recommended in the GeneAmp kit (US Biochemicals, Cleveland, Ohio). The samples were amplified with a programmable thermal controller; the first five rounds of amplification consisted of denaturation at 94° for 30 sec., annealing of primers to the template at 45° for 1 min. 30 sec., and chain elongation at 70° for 4 min. The final 20 rounds of amplification consisted of denaturation as above, annealing at 55° for 1 min. 30 sec. and elongation as above. The PCR generated bands corresponding to the predicted size on an analytical gel and DNA sequencing confirmed that the cDNAs corresponded to full-length and truncated Amb a IA and Amb a II (FIGS. 11 and 15, respectively) and full-length Amb a ID (FIG. 14).

The near full-length cDNAs presented in FIGS. 11 through 15, have their nucleotide sequences numbered such that the first nucleotide is designated number 1. Although some cDNAs start at what is probably the N-terminal methionine (Amb a IB, FIG. 12; Amb a IC, FIG. 13), some do not (Amb a IA, FIG. 11; Amb a ID, FIG. 14; Amb a II, FIG. 15). Consequently, since the cDNAs are of different lengths, their nucleotide numbers do not necessarily correspond from one sequence to another. The universal genetic code is used to deduce the amino acid sequences from the cDNA sequences and the complete amino acid sequence comparisons between the clones are presented in FIG. 16. In FIG. 16, the amino acids are numbered sequentially from the probably N-terminal methionine (designated number 1) of the Amb a IB sequence.

EXAMPLE 4

T Cell Responses to Ragweed Proteins and Peptides

Figure 21:
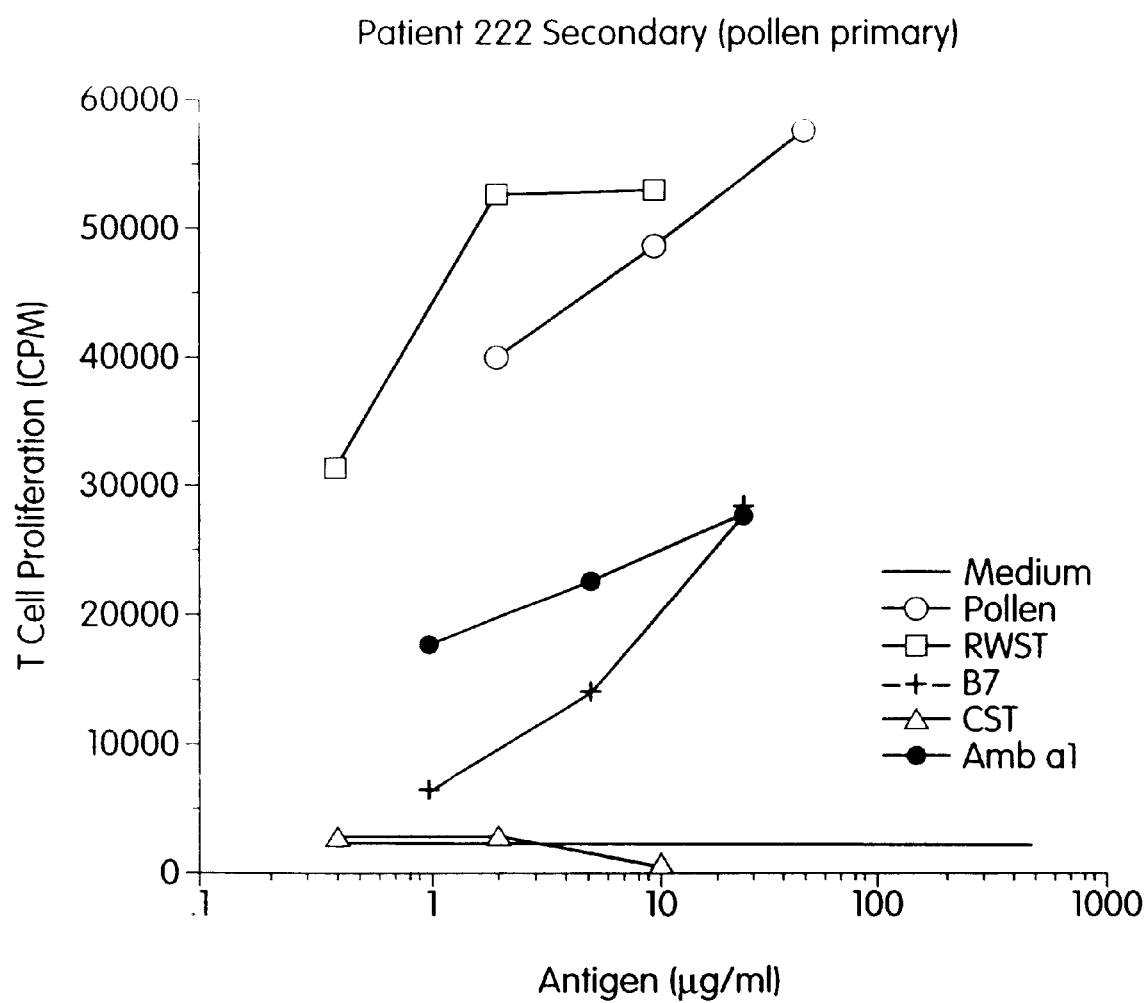

Peripheral blood mononuclear cells (PBMC) were purified from 60 ml of heparinized blood from ragweed-allergic patients. PBMC were subsequently treated as described below, although in individual cases, the length of time of cultivation with IL-2 and IL-4 and the specific ragweed proteins and peptides used for stimulation varied. As an example, ten ml of patient 222 PBMC at $10^6$/ml were cultured at 37° C. for 7 days in the presence of 20 micrograms aqueous ragweed pollen extract/ml RPMI-1640 supplemented with 5% pooled human AB serum. Viable cells were purified by Ficoll-Hypaque centrifugation and cultured for three weeks at 5 units recombinant human IL-2/ml and 5 units recombinant human IL-4/ml. The resting T cells were then restimulated (secondary) with 20 micrograms aqueous ragweed pollen extract/ml at a density of $2\times10^5$ T cells/ml in the presence of X-irradiated (3500 RADS) autologous PBMC ($5\times10^5$/ml) for three days, purified by Ficoll-Hypaque centrifugation and grown in 5 units IL-2/ml and 5 units IL-4/ml for two weeks. For assay, $2\times10^4$ resting secondary T cells were restimulated (tertiary) in the presence of $5\times10^4$ X-irradiated (3500 RADS) autologous PBMC or $2\times10^4$ autologous Epstein-Barr virus-transformed B cells (20,000 RADS) with various concentrations of allergen or their fragments in a volume of 200 microliters in 96-well round bottom assay plates for 3 days. Each well then received 1 microCurie tritiated (methyl) thymidine for 16 hours. The counts incorporated were collected onto glass fiber filters and processed for liquid scintillation counting. FIG. 21 shows the results of a representative assay, demonstrating the reactivity and specificity of the T cell culture to ragweed pollen proteins. Antigens used: IPC aqueous pollen extract (pollen), Hollister-Stier ragweed skin test extract (RWST), ALK cat epithelium skin test extract (CST), affinity 4B5/B7 antibody purified (dialyzed) Amb a I (B7), and chromatographically purified Amb a I (Amb a I). Medium only control is shown as a line with no symbol. Alternatively, PBMC were sometimes carried only into a secondary assay (as outlined above for a tertiary assay) with 20 micrograms aqueous pollen extract for 7 days, followed by culture in 5 units IL-2/ml and 5 units IL-4/ml for 2–3 weeks. One ragweed allergic patient's T cells in secondary assay responded to pollen extract, RWST, B7 or Amb a I, but did not respond to CST or medium only (FIG. 21). Secondary and tertiary assays of a panel of ragweed allergic patients were performed using synthetic peptides derived from the sequences of various ragweed pollen proteins. The results of several experiments are shown in Table 5. Three peptides (RAE16.6, RAE45.15, RAE24.E) which are derived from the sequence of three different Amb a I cDNA's could not stimulate any of the patients' T cells. Another four peptides (RAE15.6, RAE3.D, RAE28.1, RAE26.15) which are also dervied from the sequence of the same three cDNA's could stimulate 35 to 58% of the patients' T cells. One peptide (RAE4) which is derived from the cDNA of IPC Clone 5 could also stimulate 25% of the patients' T cells. These results are consistent with the above cDNA's encoding ragweed pollen proteins. They further demonstrate the opportunity offered by knowledge of the protein structures of the Amb I/II family/ies to identify peptidic fragments which stimulate a response in T cells from ragweed allergic patients and others which do not. By this method it is possible to identify novel therapeutic and diagnostics entities for use in the treatment and the diagnosis of ragweed allergy.

TABLE 5

Human Ragweed-Allergic T Cell Responses to Ragweed Peptides

| PEPTIDE[b] NAME | SEQUENCE BASED ON | NO. PATIENTS TESTED | NUMBER POSITIVE | POSITIVE % |
|---|---|---|---|---|
| RAE 16.6 | Amb a IB | 7 | 0 | 0 |
| RAE 45.15 | Amb a IC | 2 | 0 | 0 |
| RAE 24.E | Amb a IA | 9 | 0 | 0 |
| RAE 4 | Clone #5 | 28 | 7 | 25 |
| RAE 15.6 | Amb a IB | 20 | 7 | 35 |
| RAE 3.D | Amb a IA | 35 | 13 | 37 |
| RAE 28.1 | Amb a IA | 33 | 17 | 52 |
| RAE 26.15 | Amb a IC | 24 | 14 | 58 |

[a]Responses were scored as positive when the T cell proliferative response of ragweed pollen-specific T cells was greater than 2-fold above the culture medium control.
[b]Sequence of named peptide is as follows:

TABLE 5-continued

Human Ragweed-Allergic T Cell Responses to Ragweed Peptides

| PEPTIDE[b] NAME | SEQUENCE BASED ON | NO. PATIENTS TESTED | NUMBER POSITIVE | POSITIVE % |
|---|---|---|---|---|
| RAE 16.6 | RTDKDLLENGAIC (SEQ ID NO: 48) | | | |
| RAE 45.15 | LNQELVVNSDKTIDGRGVK (SEQ ID NO: 49) | | | |
| RAE 24.E | ETRRSLKTSGAYNIIDGCWRGKAD (SEQ ID NO: 50) | | | |
| RAE 4 | EFPILGGITEVKDNDNSVDFC (SEQ ID NO: 51) | | | |
| RAE 15.6 | YTVTSDKDDDVANC (SEQ ID NO: 52) | | | |
| RAE 3.D | GKADWAENRC (SEQ ID NO: 53) | | | |
| RAE 28.1 | LENGAIFVASGVDPVLTPEQ (SEQ ID NO: 54) | | | |
| RAE 26.15 | GFFQVVNNNYDRWGTYA (SEQ ID NO: 55) | | | |

EXAMPLE 5

Antibody-Binding-to Recombinant Affinity Purified *Amb a* I, and Pollen Extract Derived *Amb a* I and *Amb a* II Affinity purified *Amb a* I was electrophoresed, Western transferred (Towbin et al., *Proc. Natl. Acad. Sci. USA*, 76:4350 (1979)) and probed with a variety of antibodies, including IgE from an allergic patient (FIG. 17). In pollen extract *Amb a* I is not only present as an intact 38-KD species, but also characterized by its component 26-KD alpha chains and 12-KD beta chains which are formed by enzymatic cleavage. The intact 38-KD species and the alpha chain are clearly detected using rabbit anti-*Amb a* I, polyclonal affinity purified anti-RAE 16 and monoclonal anti-*Amb a* I JBIE3-4 (FIG. 17; RAE 16 peptide has the sequence RTDKDLLENGAIC derived from amino-acids 342–353 of *Amb a* IB, FIG. 16). Affinity purified *Amb a* I (partial sequence presented in Table 1) as well as chromatographically purified *Amb a* II (partial sequence presented in Table 2) are bound on Western blots by these antibodies as well as by patient IgE (FIG. 17). The goat anti-*Amb a* I polyclonal antibody also binds multiple *Amb a* I and *Amb a* II species on a two dimensional Western blot of pollen extract (FIG. 18). The Western blot was performed as outlined below.

Isoelectric focusing was done on a Hoeffer gel apparatus with 15 μg of crude soluble pollen protein. The gel consisted of 7.5% acrylamide with 3.5% Pharmalytes pH 4.5–5.3 (Pharmacia) and 3.5% Ampholines pH 3.5–10 (LKB), run at 13W for 3.5 hours until a constant voltage was reached. The gel section was placed on a slab of 10% acrylamide SDS-PAGE and electrophoresed for 3.5 hours at 40 mA according to the protocol cited. The proteins were transferred overnight in phosphate buffer to 0.1 micron nitrocellulose (Schleicher and Schuell) at 0.2 A. The blot was rinsed in blot solution (25 mM Tris-HCl pH 7.5, 0.171 M NaCl, 0.05% Tween-20; Sigma). The first antibody incubation was overnight OS at room temperature with a 1:000 dilution of goat anti-*Amb a* I IgG (obtained from Dr. David Marsh) in blot solution. The excess first antibody was removed with three 15 minute rinses with blot solution. The second antibody was a 1:2,500 dilution of biotinylated swine anti-goat IgG (Boehringer-Manneheim) in blot solution for two hours. The blot was then rinsed with blot solution three times for 15 minutes and incubated for 1 hr in blot solution with 2 μCi $I^{125}$ streptavidin (Amersham). The blots were rinsed with blot solution until the waste wash was down to background. The blot was then exposed to film at −80° C. overnight. In the case of one-dimensional SDS-PAGE Western blots (FIGS. 17, 19 and 20) the isoelectric focusing step was omitted. When human sera was used to probe the Western blots (FIGS. 17 and 20), 10% human plasma in 1% milk in blot solution was incubated overnight with the blot prior to using as second antibody biotinylated goat anti-human IgE.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

SEQUENCE LISTING (1) GENERAL INFORMATION:

(iii) NUMBER OF SEQUENCES: 93

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

Trp Glu Asn Phe Lys
1         5

(2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:2:

```
Val Trp Val Lys Pro Trp Glu Asn Phe Lys
 1               5                  10
```

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Val Trp Val Lys Pro
 1               5
```

(2) INFORMATION FOR SEQ ID NO:4:

(i) SEQUENCE CHARACTERISTICS:
        (A) LENGTH: 48 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Thr Ser Gly Ala Tyr Asn Ile Ile Asp Gly Cys Trp Arg Gly Lys Ala
 1               5                  10                  15

Asp Trp Ala Glu Asn Arg Lys Ala Leu Ala Asp Cys Ala Gln Gly Phe
                20                  25                  30

Gly Lys Gly Thr Val Gly Gly Lys Asp Gly Asp Ile Tyr Thr Val Thr
            35                  40                  45
```

(2) INFORMATION FOR SEQ ID NO:5:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Thr Ser Gly Ala Tyr Asn Ile Ile Asp Gly Cys Trp Arg Gly Lys Ala
 1               5                  10                  15

Asp Trp Ala Glu Asn Arg Lys Ala Leu Ala Asp Cys Ala Gln Gly Phe
                20                  25                  30

Gly
```

(2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Asp Ser Gly Ala Tyr Asn Ile Ile Asp Gly Cys Trp Arg Gly Lys Ala
1               5                  10                  15
Asp Trp Ala Glu Asn Ser Arg Ala Leu Ala Asp Cys Ala Gln Gly Phe
            20                  25                  30
Gly
```

(2) INFORMATION FOR SEQ ID NO:7:

(i) SEQUENCE CHARACTERISTICS:
        (A) LENGTH: 48 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Thr Ser Gly Ala Tyr Asn Ile Ile Asp Gly Cys Trp Arg Gly Lys Ala
1               5                  10                  15
Asp Trp Ala Glu Asn Arg Lys Ala Leu Ala Asp Cys Ala Gln Gly Phe
            20                  25                  30
Gly Lys Gly Thr Val Gly Gly Lys Asp Gly Asp Ile Tyr Thr Val Thr
            35                  40                  45
```

(2) INFORMATION FOR SEQ ID NO:8:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

```
His Asp Val Lys Val Asn Pro Gly Gly Leu Ile Lys Ser Asn Asp Gly
1               5                  10                  15
```

(2) INFORMATION FOR SEQ ID NO:9:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

```
Phe Asp Leu Lys Val Asn Ile Gly Gln Leu Ile Lys Ser Asn
1               5                  10
```

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

```
Phe Ala Phe Lys Asn Tyr Ile Pro Leu Leu Ile Asn Ser Asn
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
His Asp Val Lys Val Pro Gly Gly Leu Ile Lys Asn Gly
1               5                   10
```

(2) INFORMATION FOR SEQ ID NO:12:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Pro Arg Cys Arg His Gly Phe Phe Gln Val Val Asn Asn Asn Tyr Asp
1               5                   10                  15
Lys Trp Gly Ser Tyr Ala Ile Gly Gly Ser Ala Ser Pro Thr Ile Leu
                20                  25                  30
Ser Gln Gly Met Arg Phe Cys Ala Pro Asp Glu Arg Ser
            35                  40                  45
```

(2) INFORMATION FOR SEQ ID NO:13:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Pro Arg Cys Arg His Gly Phe Phe Gln Val Val Asn Asn Asn Tyr Asp
1               5                   10                  15
Arg Trp Gly Ser Tyr Ala Ile Gly Gly Ser Ala Pro Thr Ile Leu Ser
                20                  25                  30
```

```
Gln Gly Asn Phe Cys Ala Pro Asp Gly Tyr
        35                  40
```

(2) INFORMATION FOR SEQ ID NO:14:

(i) SEQUENCE CHARACTERISTICS:
        (A) LENGTH: 43 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Pro Arg Cys Arg Phe Gly Phe Phe Gln Ile Val Asn Asn Phe Tyr Asp
1               5                   10                  15

Arg Trp Asp His Tyr Ala Ile Gly Gly Ser Ala Asn Pro Thr Ile Leu
            20                  25                  30

Ser Gln Gly Asn Phe Val Ala Pro Asp Gly Tyr
        35                  40
```

(2) INFORMATION FOR SEQ ID NO:15:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

```
Pro Val Leu Thr Pro Glu Gln Ser Ala Gly Met
1               5                   10
```

(2) INFORMATION FOR SEQ ID NO:16:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

```
Thr Ser Gly Ala Tyr Asn Ile Ile Asp Gly Cys Trp Arg Gly Lys Ala
1               5                   10                  15

Asp Trp Ala
```

(2) INFORMATION FOR SEQ ID NO:17:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

```
Pro Arg Arg His Gly Phe Phe Gln Val Val Asn Asn Tyr Asp Glu
1               5                   10                  15
```

```
Trp Gly Ser Tyr Ala Ile Gly Gly Ser Ala Ser Pro Thr Ile
            20                  25                  30
```

(2) INFORMATION FOR SEQ ID NO:18:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

```
Ala Trp Asn Trp Arg Thr Glu Lys Asp Leu
1               5                   10
```

(2) INFORMATION FOR SEQ ID NO:19:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

```
Val Ile Asn Leu Asp Gln Glu Ile Phe Val
1               5                   10
```

(2) INFORMATION FOR SEQ ID NO:20:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

```
Pro Val Leu Thr Pro Glu Gln Ser Ala Gly Met Ile Pro Ala Glu Pro
1               5                   10                  15
Gly Glu Ser Ala Leu Ser Leu Thr Ser Ser Ala Gly Val Leu Ser Cys
            20                  25                  30
Gln Pro Gly Ala Pro
        35
```

(2) INFORMATION FOR SEQ ID NO:21:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

```
Pro Val Leu Asn Pro Glu Asn Ala Gly Met Ile Gln Ala Glu Pro Gly
1               5                   10                  15
Glu Ala
```

(2) INFORMATION FOR SEQ ID NO:22:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

```
Pro Val Ile Asn Pro Glu Asn Ala Gly Met Ile Gln Ala Glu Pro Gly
1               5                  10                  15
Glu Ala
```

(2) INFORMATION FOR SEQ ID NO:23:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

```
Pro Val Leu Thr Pro Glu Gln Ser Ala Gly Met Ile Pro Ala Glu Pro
1               5                  10                  15
Gly Glu Ser Ala Leu Ser Leu Thr Ser Ser Ala Gly Val Leu Cys Gln
                20                  25                  30
Pro Gly Ala Pro
        35
```

(2) INFORMATION FOR SEQ ID NO:24:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

```
Pro Val Leu Thr Pro Val Gln Ser Ala Gly Met Ile Pro Ala Glu Pro
1               5                  10                  15
Gly Glu Ala Ala Ile Lys Leu Thr Ser Ser
                20                  25
```

(2) INFORMATION FOR SEQ ID NO:25:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

```
Pro Arg Cys Arg Phe Gly Phe Phe Gln Ile Val Asn Asn Phe Tyr Asp
1               5                  10                  15
```

```
Arg Trp Asp Lys Tyr Ala Ile Gly Gly Ser Ser Asn Pro Thr Ile Leu
         20                  25                  30

Ser Gln Gly Asn Lys Phe Val Ala Pro Asp Phe Ile Tyr
         35                  40                  45

(2) INFORMATION FOR SEQ ID NO:26:

(i) SEQUENCE CHARACTERISTICS:
        (A) LENGTH: 43 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

Pro Arg Arg Phe Gly Phe Phe Gln Ile Val Asn Asn Phe Tyr Asp Arg
1               5                  10                  15

Trp Asp His Tyr Ala Ile Gly Gly Ser Ser Asn Pro Thr Ile Leu Ser
         20                  25                  30

Gln Gly Asn Arg Phe Val Ala Pro Asp Ile Tyr
         35                  40

(2) INFORMATION FOR SEQ ID NO:27:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

Pro Val Leu Thr Pro Glu Gln Asn Ala Gly Met
1               5                  10

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:28:

Pro Arg Arg Phe Gly Phe Phe Gln Ile Val Asn Asn Phe Tyr Asp
1               5                  10                  15

(2) INFORMATION FOR SEQ ID NO:29:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:
```

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Thr Cys
                20                  25                  30

Ser Pro Gly Ala Pro
        35
```

(2) INFORMATION FOR SEQ ID NO:30:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Ser Pro
                20                  25                  30

Gly Ala Pro
    35
```

(2) INFORMATION FOR SEQ ID NO:31:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Thr Ser
                20                  25                  30

Pro Gly Ala Pro
        35
```

(2) INFORMATION FOR SEQ ID NO:32:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

```
Pro Val Leu Thr Pro Glu Gln Ser Ala Gly Met Ile Pro Ala Glu Pro
1               5                   10                  15

Gly Glu Ser Ala Leu Ser Leu Thr Ser Asn Ala Gly Val Leu Ser Ser
                20                  25                  30

Pro Gly Ala Pro
        35
```

(2) INFORMATION FOR SEQ ID NO:33:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

```
Cys Leu Arg Thr Gly Ala Gln Glu Pro Glu Trp Met Thr
1               5                   10
```

(2) INFORMATION FOR SEQ ID NO:34:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

```
Val Trp Val Lys Pro Trp Glu Asn Phe Lys Lys
1               5                   10
```

(2) INFORMATION FOR SEQ ID NO:35:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
Trp Glu Asn Phe Lys Lys
1               5
```

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
TGGGAAAATT TCAAAAAA                                           18
```

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA

```
      (xi) SEQUENCE DESCRIPTION: SEQ ID NO:37:

TGGGAGAACT TTAAGAAG                                                18

(2) INFORMATION FOR SEQ ID NO:38:

(i) SEQUENCE CHARACTERISTICS:
           (A) LENGTH: 6 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO:38:

Trp Glu Asn Phe Lys Glu
1               5

(2) INFORMATION FOR SEQ ID NO:39:

(i) SEQUENCE CHARACTERISTICS:
           (A) LENGTH: 5 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO:39:

Val Trp Val Lys Pro
1               5

(2) INFORMATION FOR SEQ ID NO:40:

(i) SEQUENCE CHARACTERISTICS:
           (A) LENGTH: 21 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO:40:

Glu Phe Pro Ile Leu Gly Gly Ile Thr Glu Val Lys Asp Asn Asp Asn
1               5                   10                  15

Ser Val Asp Phe Cys
            20

(2) INFORMATION FOR SEQ ID NO:41:

(i) SEQUENCE CHARACTERISTICS:
           (A) LENGTH: 6 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO:41:

Leu Tyr Phe Thr Leu Ala
1               5
```

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GGGAATTCTT GTATTTTACC TTAGC     25

(2) INFORMATION FOR SEQ ID NO:43:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:43:

Asp Cys Ala Gln Gly Phe
1           5

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GGGAATTCGA CTGTGCCCAA GGTTTTG     27

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GGGCTGCAGT CATTATAAGT GCTTAGT     27

(2) INFORMATION FOR SEQ ID NO:46:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GGGCTGCAGT GCTTAGCAAG GTGCTCC     27

(2) INFORMATION FOR SEQ ID NO:47:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

GGGCTGCAGC GTGTCCAAAT CTAATCAAAT GAACACTTAT GG                42

(2) INFORMATION FOR SEQ ID NO:48:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:48:

Arg Thr Asp Lys Asp Leu Leu Glu Asn Gly Ala Ile Cys
1               5                   10

(2) INFORMATION FOR SEQ ID NO:49:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

Leu Asn Gln Glu Leu Val Val Asn Ser Asp Lys Thr Ile Asp Gly Arg
1               5                   10                  15

Gly Val Lys (2) INFORMATION FOR SEQ ID NO:50:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

Glu Thr Arg Arg Ser Leu Lys Thr Ser Gly Ala Tyr Asn Ile Ile Asp
1               5                   10                  15

Gly Cys Trp Arg Gly Lys Ala Asp
            20

(2) INFORMATION FOR SEQ ID NO:51:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

```
Glu Phe Pro Ile Leu Gly Gly Ile Thr Glu Val Lys Asp Asn Asp Asn
1               5                   10                  15
Ser Val Asp Phe Cys
            20
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

```
Tyr Thr Val Thr Ser Asp Lys Asp Asp Val Ala Asn Cys
1               5                   10
```

(2) INFORMATION FOR SEQ ID NO:53:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:53:

```
Gly Lys Ala Asp Trp Ala Glu Asn Arg Cys
1               5                   10
```

(2) INFORMATION FOR SEQ ID NO:54:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:54:

```
Leu Glu Asn Gly Ala Ile Phe Val Ala Ser Gly Val Asp Pro Val Leu
1               5                   10                  15
Thr Pro Glu Gln
            20
```

(2) INFORMATION FOR SEQ ID NO:55:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:55:

```
Gly Phe Phe Gln Val Val Asn Asn Tyr Asp Arg Trp Gly Thr Tyr
1               5                   10                  15
Ala
```

(2) INFORMATION FOR SEQ ID NO:56:

(i) SEQUENCE CHARACTERISTICS:
       (A) LENGTH: 323 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..321

(xi) SEQUENCE DESCRIPTION: SEQ ID NO:56:

```
GAA TTC GGC TGG AGA ACG AAT AAA GAC GTG CTT GAA AAT GGT GCT ATT      48
Glu Phe Gly Trp Arg Thr Asn Lys Asp Val Leu Glu Asn Gly Ala Ile
1               5                   10                  15

TTT GTT GCA TCC GGG GTC GAT CCA GTG CTA ACC CCT GAG CAA AGC GCA      96
Phe Val Ala Ser Gly Val Asp Pro Val Leu Thr Pro Glu Gln Ser Ala
                20                  25                  30

GGG ATG ATT CCA GCC GAA CCA GGA GAG TCC GCT CTA AGC CTC ACT AGT     144
Gly Met Ile Pro Ala Glu Pro Gly Glu Ser Ala Leu Ser Leu Thr Ser
            35                  40                  45

AGT GCT GGT GTA CTC TCA TGC CAA CCC GGA GCA CCT TGC TAA GCA CCC     192
Ser Ala Gly Val Leu Ser Cys Gln Pro Gly Ala Pro Cys  *  Ala Pro
        50                  55                  60

GAC CAA TTA CTA AGC ACT TAT AAT GAT CAT TAA TAC TTT TTT TTA TTT     240
Asp Gln Leu Leu Ser Thr Tyr Asn Asp His  *  Tyr Phe Phe Leu Phe
    65                  70                  75                  80

TAT TTT TGA TAT TTT ATA TGT ACT AAG GTA ATG GAA ATG AAC CTT TAC     288
Tyr Phe  *  Tyr Phe Ile Cys Thr Lys Val Met Glu Met Asn Leu Tyr
                85                  90                  95

CTT CTA GTA CTC TAA AAA AAA AAA AAA CCG AAT TC                      323
Leu Leu Val Leu  *  Lys Lys Lys Lys Pro Asn
                100                 105
```

(2) INFORMATION FOR SEQ ID NO:57:

(i) SEQUENCE CHARACTERISTICS:
       (A) LENGTH: 61 amino acids
       (B) TYPE: amino acid
       (D) TOPOLOGY: linear (ii) MOLECULE TYPE: protein (xi) SEQUENCE DESCRIPTION: SEQ ID NO:57:

```
Glu Phe Gly Trp Arg Thr Asn Lys Asp Val Leu Glu Asn Gly Ala Ile
1               5                   10                  15

Phe Val Ala Ser Gly Val Asp Pro Val Leu Thr Pro Glu Gln Ser Ala
                20                  25                  30

Gly Met Ile Pro Ala Glu Pro Gly Glu Ser Ala Leu Ser Leu Thr Ser
            35                  40                  45

Ser Ala Gly Val Leu Ser Cys Gln Pro Gly Ala Pro Cys
        50                  55                  60
```

(2) INFORMATION FOR SEQ ID NO:58:

(i) SEQUENCE CHARACTERISTICS:
        (A) LENGTH: 1328 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1328

(xi) SEQUENCE DESCRIPTION: SEQ ID NO:58:

```
TAC ATC TTG TAT TTT ACC TTA GCC CTT GTC ACT TTG CTG CAA CCT GTT      48
Tyr Ile Leu Tyr Phe Thr Leu Ala Leu Val Thr Leu Leu Gln Pro Val
 1               5                  10                  15

CGT TCT GCA GAA GAT GTT GAA GAA TTC TTA CCT TCA GCT AAC GAA ACA      96
Arg Ser Ala Glu Asp Val Glu Glu Phe Leu Pro Ser Ala Asn Glu Thr
             20                  25                  30

AGG AGG AGC CTG AAA GCA TGT GAA GCA CAC AAC ATT ATA GAC AAG TGC     144
Arg Arg Ser Leu Lys Ala Cys Glu Ala His Asn Ile Ile Asp Lys Cys
         35                  40                  45

TGG AGG TGC AAA GCC GAT TGG GCG AAT AAC CGA CAA GCG TTA GCC GAT     192
Trp Arg Cys Lys Ala Asp Trp Ala Asn Asn Arg Gln Ala Leu Ala Asp
 50                  55                  60

TGT GCC CAA GGT TTT GCA AAG GGA ACC TAC GGT GGA AAA CAT GGT GAT     240
Cys Ala Gln Gly Phe Ala Lys Gly Thr Tyr Gly Gly Lys His Gly Asp
 65                  70                  75                  80

GTC TAC ACG GTC ACC AGT GAT AAA GAT GAT GAT GTT GCA AAT CCA AAA     288
Val Tyr Thr Val Thr Ser Asp Lys Asp Asp Asp Val Ala Asn Pro Lys
                 85                  90                  95

GAA GGC ACA CTC CGG TTT GCT GCT GCC CAA AAC AGG CCC TTG TGG ATC     336
Glu Gly Thr Leu Arg Phe Ala Ala Ala Gln Asn Arg Pro Leu Trp Ile
            100                 105                 110

ATT TTT AAA AGA AAT ATG GTG ATT CAT TTG AAT CAA GAG CTT GTC GTA     384
Ile Phe Lys Arg Asn Met Val Ile His Leu Asn Gln Glu Leu Val Val
        115                 120                 125

AAC AGC GAC AAG ACC ATC GAT GGC CGA GGG GTG AAA GTT AAC ATC GTT     432
Asn Ser Asp Lys Thr Ile Asp Gly Arg Gly Val Lys Val Asn Ile Val
    130                 135                 140

AAC GCC GGT CTC ACC CTC ATG AAT GTC AAG AAT ATA ATC ATT CAT AAC     480
Asn Ala Gly Leu Thr Leu Met Asn Val Lys Asn Ile Ile Ile His Asn
145                 150                 155                 160

ATA AAT ATC CAT GAT ATT AAA GTT TGT CCA GGA GGC ATG ATT AAG TCC     528
Ile Asn Ile His Asp Ile Lys Val Cys Pro Gly Gly Met Ile Lys Ser
                165                 170                 175

AAC GAT GGT CCA CCA ATT TTA AGA CAA CAA AGT GAT GGT GAT GCT ATA     576
Asn Asp Gly Pro Pro Ile Leu Arg Gln Gln Ser Asp Gly Asp Ala Ile
            180                 185                 190

AAT GTT GCT GGT AGT TCA CAA ATA TGG ATC GAC CAT TGC TCG CTC AGT     624
Asn Val Ala Gly Ser Ser Gln Ile Trp Ile Asp His Cys Ser Leu Ser
        195                 200                 205

AAG GCT TCC GAT GGG CTG CTC GAT ATC ACC CTC GGC AGC TCA CAC GTG     672
Lys Ala Ser Asp Gly Leu Leu Asp Ile Thr Leu Gly Ser Ser His Val
    210                 215                 220

ACC GTT TCC AAC TGC AAA TTC ACC CAA CAC CAA TTT GTA TTA TTG CTC     720
Thr Val Ser Asn Cys Lys Phe Thr Gln His Gln Phe Val Leu Leu Leu
225                 230                 235                 240

GGG GCT GAT GAC ACC CAT TAT CAA GAT AAA GGC ATG CTA GCA ACG GTA     768
Gly Ala Asp Asp Thr His Tyr Gln Asp Lys Gly Met Leu Ala Thr Val
                245                 250                 255
```

| | | |
|---|---|---|
| GCA TTC AAC ATG TTC ACC GAT CAC GTT GAC CAA AGA ATG CCT AGA TGT | | 816 |
| Ala Phe Asn Met Phe Thr Asp His Val Asp Gln Arg Met Pro Arg Cys | | |
| 260 265 270 | | |
| AGA TTT GGG TTT TTC CAA GTC GTT AAC AAC AAC TAC GAC AGA TGG GGA | | 864 |
| Arg Phe Gly Phe Phe Gln Val Val Asn Asn Asn Tyr Asp Arg Trp Gly | | |
| 275 280 285 | | |
| ACG TAC GCC ATC GGT GGT AGC TCG GCC CCA ACT ATA CTC AGC CAA GGG | | 912 |
| Thr Tyr Ala Ile Gly Gly Ser Ser Ala Pro Thr Ile Leu Ser Gln Gly | | |
| 290 295 300 | | |
| AAC AGA TTC TTC GCC CCC GAT GAT ATC ATC AAG GAA AAT GTC TTA GCG | | 960 |
| Asn Arg Phe Phe Ala Pro Asp Asp Ile Ile Lys Glu Asn Val Leu Ala | | |
| 305 310 315 320 | | |
| AGG ACT GGT ACT GGC AAC GCA GAG TCG ATG TCG TGG AAC TGG AGA ACA | | 1008 |
| Arg Thr Gly Thr Gly Asn Ala Glu Ser Met Ser Trp Asn Trp Arg Thr | | |
| 325 330 335 | | |
| GAT AAA GAC TTG CTT GAA AAT GGT GCT ATT TTT CTC CCA TCC GGG TCT | | 1056 |
| Asp Lys Asp Leu Leu Glu Asn Gly Ala Ile Phe Leu Pro Ser Gly Ser | | |
| 340 345 350 | | |
| GAT CCA GTG CTA ACC CCT GAG CAA AAA GCA GGG ATG ATT CCA GCT GAA | | 1104 |
| Asp Pro Val Leu Thr Pro Glu Gln Lys Ala Gly Met Ile Pro Ala Glu | | |
| 355 360 365 | | |
| CCA GGA GAA GCC GTT CTA AGA CTC ACT AGT AGT GCT GGT GTA CTC TCA | | 1152 |
| Pro Gly Glu Ala Val Leu Arg Leu Thr Ser Ser Ala Gly Val Leu Ser | | |
| 370 375 380 | | |
| TGC CAT CAA GGA GCA CCT TGC TAA GCA CCT GGC CAA TTC CTA AGC TTT | | 1200 |
| Cys His Gln Gly Ala Pro Cys * Ala Pro Gly Gln Phe Leu Ser Phe | | |
| 385 390 395 400 | | |
| TAT AAT AAT CAT AAA TAC TTA TTT TAT TTT ATT TTT GAT ATT TTA TAT | | 1248 |
| Tyr Asn Asn His Lys Tyr Leu Phe Tyr Phe Ile Phe Asp Ile Leu Tyr | | |
| 405 410 415 | | |
| GAA CCA TTA CGT TCA AGT ACT CTA TTA ACA TGT TTT AAA TTC ATA AGA | | 1296 |
| Glu Pro Leu Arg Ser Ser Thr Leu Leu Thr Cys Phe Lys Phe Ile Arg | | |
| 420 425 430 | | |
| GTT TAT TGA TAA AAA AAA AAA AAA CCG AAT TC | | 1328 |
| Val Tyr * * Lys Lys Lys Lys Pro Asn | | |
| 435 440 | | |

(2) INFORMATION FOR SEQ ID NO:59:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:59:

Tyr Ile Leu Tyr Phe Thr Leu Ala Leu Val Thr Leu Leu Gln Pro Val
 1            5                10              15

Arg Ser Ala Glu Asp Val Glu Phe Leu Pro Ser Ala Asn Glu Thr
            20              25             30

Arg Arg Ser Leu Lys Ala Cys Glu Ala His Asn Ile Ile Asp Lys Cys
         35               40              45

Trp Arg Cys Lys Ala Asp Trp Ala Asn Asn Arg Gln Ala Leu Ala Asp
    50              55              60

Cys Ala Gln Gly Phe Ala Lys Gly Thr Tyr Gly Gly Lys His Gly Asp
 65            70               75             80

Val Tyr Thr Val Thr Ser Asp Lys Asp Asp Val Ala Asn Pro Lys
            85              90             95

```
Glu Gly Thr Leu Arg Phe Ala Ala Gln Asn Arg Pro Leu Trp Ile
            100                 105                 110
Ile Phe Lys Arg Asn Met Val Ile His Leu Asn Gln Glu Leu Val Val
            115                 120                 125
Asn Ser Asp Lys Thr Ile Asp Gly Arg Gly Val Lys Val Asn Ile Val
130                 135                 140
Asn Ala Gly Leu Thr Leu Met Asn Val Lys Asn Ile Ile His Asn
145                 150                 155                 160
Ile Asn Ile His Asp Ile Lys Val Cys Pro Gly Gly Met Ile Lys Ser
                165                 170                 175
Asn Asp Gly Pro Pro Ile Leu Arg Gln Gln Ser Asp Gly Asp Ala Ile
            180                 185                 190
Asn Val Ala Gly Ser Ser Gln Ile Trp Ile Asp His Cys Ser Leu Ser
            195                 200                 205
Lys Ala Ser Asp Gly Leu Leu Asp Ile Thr Leu Gly Ser Ser His Val
210                 215                 220
Thr Val Ser Asn Cys Lys Phe Thr Gln His Gln Phe Val Leu Leu Leu
225                 230                 235                 240
Gly Ala Asp Asp Thr His Tyr Gln Asp Lys Gly Met Leu Ala Thr Val
                245                 250                 255
Ala Phe Asn Met Phe Thr Asp His Val Asp Gln Arg Met Pro Arg Cys
            260                 265                 270
Arg Phe Gly Phe Phe Gln Val Val Asn Asn Asn Tyr Asp Arg Trp Gly
            275                 280                 285
Thr Tyr Ala Ile Gly Gly Ser Ser Ala Pro Thr Ile Leu Ser Gln Gly
290                 295                 300
Asn Arg Phe Phe Ala Pro Asp Asp Ile Ile Lys Glu Asn Val Leu Ala
305                 310                 315                 320
Arg Thr Gly Thr Gly Asn Ala Glu Ser Met Ser Trp Asn Trp Arg Thr
                325                 330                 335
Asp Lys Asp Leu Leu Glu Asn Gly Ala Ile Phe Leu Pro Ser Gly Ser
            340                 345                 350
Asp Pro Val Leu Thr Pro Glu Gln Lys Ala Gly Met Ile Pro Ala Glu
            355                 360                 365
Pro Gly Glu Ala Val Leu Arg Leu Thr Ser Ser Ala Gly Val Leu Ser
370                 375                 380
Cys His Gln Gly Ala Pro Cys
385                 390

(2) INFORMATION FOR SEQ ID NO:60:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..300

(xi) SEQUENCE DESCRIPTION: SEQ ID NO:60:

GAA TTC GGC TGG AGA ACG AAT AAA GAC GTG CTT GAA AAT GGT GCT ATT      48
Glu Phe Gly Trp Arg Thr Asn Lys Asp Val Leu Glu Asn Gly Ala Ile
1               5                   10                  15
```

```
TTT GTT GCA TCC GGG GTC GAT CCA GTG CTA ACC CCT GAG CAA AGC GCA      96
Phe Val Ala Ser Gly Val Asp Pro Val Leu Thr Pro Glu Gln Ser Ala
            20                  25                  30

GGG ATG ATT CCA GCC GAA CCA GGA GAG TCC GCT CTA AGC CTC ACT AGT     144
Gly Met Ile Pro Ala Glu Pro Gly Glu Ser Ala Leu Ser Leu Thr Ser
            35                  40                  45

AGT GCT GGT GTA CTC TCA TGC CAA CCC GGA GCA CCT TGC TAA GCA CCC     192
Ser Ala Gly Val Leu Ser Cys Gln Pro Gly Ala Pro Cys  *  Ala Pro
            50                  55                  60

GAC CAA TTA CTA AGC ACT TAT AAT GAT CAT TAA TAC TTT TTT TTA TTT     240
Asp Gln Leu Leu Ser Thr Tyr Asn Asp His  *  Tyr Phe Phe Leu Phe
65                  70                  75                  80

TAT TTT TGA TAT TTT ATA TGT ACT AAG GTA ATG GAA ATG AAC CTT TAC     288
Tyr Phe  *  Tyr Phe Ile Cys Thr Lys Val Met Glu Met Asn Leu Tyr
            85                  90                  95

CTT CTT AGT ACT CTAAAAAAAA AAAAAACCGA ATTC                          324
Leu Leu Ser Thr
            100
```

(2) INFORMATION FOR SEQ ID NO:61:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:61:

```
Glu Phe Gly Trp Arg Thr Asn Lys Asp Val Leu Glu Asn Gly Ala Ile
1               5                   10                  15

Phe Val Ala Ser Gly Val Asp Pro Val Leu Thr Pro Glu Gln Ser Ala
            20                  25                  30

Gly Met Ile Pro Ala Glu Pro Gly Glu Ser Ala Leu Ser Leu Thr Ser
            35                  40                  45

Ser Ala Gly Val Leu Ser Cys Gln Pro Gly Ala Pro Cys
            50                  55                  60
```

(2) INFORMATION FOR SEQ ID NO:62:

(i) SEQUENCE CHARACTERISTICS:
        (A) LENGTH: 452 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
GAATTCCGAT TCTTGGAGGA ATTACCGAAG TTAAAGACAA TGATAACAGC GTCGATTTCG     60

ACGAGCTTGC TAAATTCGCC ATCGCTGAAC ACAACAAGAA GGAGAATGCT GCTCTGGAGT    120

TTGGAAAAGT AATAGAAAAA AAGCAGCAGG CGGTACAGGG CACCATGTAT TATATAAAAG    180

TGGAAGCAAA TGATGGTGGT GAGAAGAAAA CTTATGAAGC CAAGGTGTGG GTTAAGCTAT    240

GGGAAAATTT CAAGGAATTG CAGGAACTCA AACTTGTTTG ATGGACGGGT GTGTGCTATG    300

ACAAAATAGC TCGAGCAGGT GAAGCATGAA TGTATAAATA TTCTTTTTAA GTTTAATAAT    360

AAACATTTCT TGTAATATGG TACAGGTTTA TGTACTTTGG TATGTATAAC AGAAAACATA    420

TCATAAATTC AAACTTAGAA TTTTGGGAAT TC                                  452
```

(2) INFORMATION FOR SEQ ID NO:63:

(i) SEQUENCE CHARACTERISTICS:
        (A) LENGTH: 452 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
GAATTCCCAA AATTCTAAGT TTGAATTTAT GATATGTTTT CTGTTATACA TACCAAAGTA    60
CATAAACCTG TACCATATTA CAAGAAATGT TTATTATTAA ACTTAAAAAG AATATTTATA   120
CATTCATGCT TCACCTGCTC GAGCTATTTT GTCATAGCAC ACACCCGTCC ATCAAACAAG   180
TTTGAGTTCC TGCAATTCCT TGAAATTTTC CCATAGCTTA ACCCACACCT TGGCTTCATA   240
AGTTTTCTTC TCACCACCAT CATTTGCTTC CACTTTTATA TAATACATGG TGCCCTGTAC   300
CGCCTGCTGC TTTTTTTCTA TTACTTTTCC AAACTCCAGA GCAGCATTCT CCTTCTTGTT   360
GTGTTCAGCG ATGGCGAATT TAGCAAGCTC GTCGAAATCG ACGCTGTTAT CATTGTCTTT   420
AACTTCGGTA ATTCCTCCAA GAATCGGAAT TC                                 452
```

(2) INFORMATION FOR SEQ ID NO:64:

(i) SEQUENCE CHARACTERISTICS:
        (A) LENGTH: 488 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

```
GAATTCCCGA TTCTTGGAGG AATTACCGAA GTTAAAGACA ATGATAACAG CGTCGATTTC    60
GACGAGCTTG CTAAATTCGC CATCACTGAA CACAACAAGA AGGAGAATGC TGCTCTGGAG   120
TTTGGAAAAG TAATAGAAAA AAAGCAGCAG GCGGTACAGG GCACCATGTA TTATATAAAA   180
GCGGAAGCAA ATGATGGTGG TGAGAAGAAA ACTTATGAAG CCAAGGTGTG GGTTAAGCTA   240
TGGGAAAATT TCAAGGAATT TGCAAGGAAC TCAAACCTTG TTTGATGATG CCACCTCACC   300
TTAACTCCAT ATGGACGGTG TGCTATGACA AAATAGCTCA AGGAGGTGAA GCATAAATGT   360
ATAAATATTC TTTTTAAGTT TAATAATAAA CATTTCTTGT AATATAGTAC AAGTTTATGT   420
ACTTTGGTAT GTATAACAGA AAACATATCA TAAATTCAAA CTTAATGTTT TTTTTCTCG   480
CGGAATTC                                                            488
```

(2) INFORMATION FOR SEQ ID NO:65:

(i) SEQUENCE CHARACTERISTICS:
        (A) LENGTH: 488 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

```
GAATTCCGCG AGAAAAAAAA ACATTAAGTT TGAATTTATG ATATGTTTTC TGTTATACAT    60
ACCAAAGTAC ATAAACTTGT ACTATATTAC AAGAAATGTT TATTATTAAA CTTAAAAGA   120
ATATTTATAC ATTTATGCTT CACCTCCTTG AGCTATTTTG TCATAGCACA CCGTCCATAT   180
GGAGTTAAGG TGAGGTGGCA TCATCAAACA AGGTTTGAGT TCCTTGCAAA TTCCTTGAAA   240
```

```
TTTTCCCATA GCTTAACCCA CACCTTGGCT TCATAAGTTT TCTTCTCACC ACCATCATTT    300

GCTTCCGCTT TTATATAATA CATGGTGCCC TGTACCGCCT GCTGCTTTTT TTCTATTACT    360

TTTCCAAACT CCAGAGCAGC ATTCTCCTTC TTGTTGTGTT CAGTGATGGC GAATTTAGCA    420

AGCTCGTCGA AATCGACGCT GTTATCATTG TCTTTAACTT CGGTAATTCC TCCAAGAATC    480

GGGAATTC                                                              488
```

(2) INFORMATION FOR SEQ ID NO:66:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

```
TCGATTCGCT GTCGATGAAC ACAACAAGAA GCAGAATACC CTGCTGGAAT TTAAGAAGGT     60

ACTGAATACA AAGGAGCAGG TAGTAGCTGG TATAATGTAT TATATCACAC TTGAAGCAAC    120

TGATGGTGGT GAGAAAAAGA CTTATGAAGC CAAGGTTTGG GTTAAGCCAT GGGAAAACTT    180

CAAAGAATTC                                                            190
```

(2) INFORMATION FOR SEQ ID NO:67:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

```
GAATTCTTTG AAGTTTTCCC ATGGCTTAAC CCAAACCTTG GCTTCATAAG TCTTTTTCTC     60

ACCACCATCA GTTGCTTCAA GTGTGATATA ATACATTATA CCAGCTACTA CCTGCTCCTT    120

TGTATTCAGT ACCTTCTTAA ATTCCAGCAG GGTATTCTGC TTCTTGTTGT GTTCATCGAC    180

AGCGAATCGA                                                            190
```

(2) INFORMATION FOR SEQ ID NO:68:

(i) SEQUENCE CHARACTERISTICS:
        (A) LENGTH: 92 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:68:

```
Ile Pro Ile Leu Gly Gly Ile Thr Glu Val Lys Asp Asn Asp Asn Ser
 1               5                  10                  15

Val Asp Phe Asp Glu Leu Ala Lys Phe Ala Ile Ala Glu His Asn Lys
                20                  25                  30

Lys Glu Asn Ala Ala Leu Glu Phe Gly Lys Val Ile Glu Lys Lys Gln
            35                  40                  45

Gln Ala Val Gln Gly Thr Met Tyr Tyr Ile Lys Val Glu Ala Asn Asp
        50                  55                  60
```

Gly Gly Glu Lys Lys Thr Tyr Glu Ala Lys Val Trp Val Lys Leu Trp
65                  70                  75                  80

Glu Asn Phe Lys Glu Leu Gln Glu Leu Lys Leu Val
                85                  90

(2) INFORMATION FOR SEQ ID NO:69:

(i) SEQUENCE CHARACTERISTICS:
        (A) LENGTH: 94 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:69:

Glu Phe Pro Ile Leu Gly Gly Ile Thr Glu Val Lys Asp Asn Asp Asn
1               5                   10                  15

Ser Val Asp Phe Asp Glu Leu Ala Lys Phe Ala Ile Thr Glu His Asn
                20                  25                  30

Lys Lys Glu Asn Ala Ala Leu Glu Phe Gly Lys Val Ile Glu Lys Lys
                35                  40                  45

Gln Gln Ala Val Gln Gly Thr Met Tyr Tyr Ile Lys Ala Glu Ala Asn
50                  55                  60

Asp Gly Gly Glu Lys Lys Thr Tyr Glu Ala Lys Val Trp Val Lys Leu
65                  70                  75                  80

Trp Glu Asn Phe Lys Glu Phe Ala Arg Asn Ser Asn Leu Val
                85                  90

(2) INFORMATION FOR SEQ ID NO:70:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:70:

Val Asp Glu His Asn Lys Lys Gln Asn Thr Leu Leu Glu Phe Lys Lys
1               5                   10                  15

Val Leu Asn Thr Lys Glu Gln Val Val Ala Gly Ile Met Tyr Tyr Ile
                20                  25                  30

Thr Leu Glu Ala Thr Asp Gly Gly Glu Lys Lys Thr Tyr Glu Ala Lys
                35                  40                  45

Val Trp Val Lys Pro Trp Glu Asn Phe Lys Glu Phe
50                  55                  60

(2) INFORMATION FOR SEQ ID NO:71:

(i) SEQUENCE CHARACTERISTICS:
        (A) LENGTH: 1196 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1161

(xi) SEQUENCE DESCRIPTION: SEQ ID NO:71:

| | | | | | | | | | | | | | | | | |
|---|---|---|---|---|---|---|---|---|---|---|---|---|---|---|---|---|
| TTG | TAT | TTT | ACC | TTA | GCC | CTT | GTC | ACT | TTG | CTG | CAA | CCT | GTT | CGT | TCT | 48 |
| Leu | Tyr | Phe | Thr | Leu | Ala | Leu | Val | Thr | Leu | Leu | Gln | Pro | Val | Arg | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GCC | GAA | GAT | CTC | CAG | GAA | ATC | TTA | CCA | GTT | AAC | GAA | ACA | AGG | AGG | CTG | 96 |
| Ala | Glu | Asp | Leu | Gln | Glu | Ile | Leu | Pro | Val | Asn | Glu | Thr | Arg | Arg | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| ACA | ACA | AGT | GGA | GCA | TAC | AAC | ATT | ATA | GAC | GGG | TGC | TGG | AGG | GGC | AAA | 144 |
| Thr | Thr | Ser | Gly | Ala | Tyr | Asn | Ile | Ile | Asp | Gly | Cys | Trp | Arg | Gly | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| GCC | GAT | TGG | GCG | GAA | AAC | CGA | AAA | GCG | TTA | GCC | GAT | TGT | GCC | CAA | GGT | 192 |
| Ala | Asp | Trp | Ala | Glu | Asn | Arg | Lys | Ala | Leu | Ala | Asp | Cys | Ala | Gln | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| TTT | GGG | AAG | GGA | ACA | GTG | GGC | GGA | AAA | GAT | GGT | GAT | ATA | TAC | ACG | GTC | 240 |
| Phe | Gly | Lys | Gly | Thr | Val | Gly | Gly | Lys | Asp | Gly | Asp | Ile | Tyr | Thr | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ACC | AGT | GAG | CTA | GAT | GAT | GAT | GTT | GCA | AAT | CCA | AAA | GAA | GGC | ACA | CTC | 288 |
| Thr | Ser | Glu | Leu | Asp | Asp | Asp | Val | Ala | Asn | Pro | Lys | Glu | Gly | Thr | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| CGG | TTT | GGT | GCC | GCC | CAA | AAC | AGG | CCC | TTG | TGG | ATC | ATT | TTT | GAA | AGA | 336 |
| Arg | Phe | Gly | Ala | Ala | Gln | Asn | Arg | Pro | Leu | Trp | Ile | Ile | Phe | Glu | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| GAT | ATG | GTG | ATT | CGT | TTG | GAT | AAA | GAG | ATG | GTG | GTA | AAC | AGT | GAC | AAG | 384 |
| Asp | Met | Val | Ile | Arg | Leu | Asp | Lys | Glu | Met | Val | Val | Asn | Ser | Asp | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| ACC | ATC | GAT | GGC | CGA | GGG | GCG | AAA | GTT | GAA | ATC | ATT | AAC | GCT | GGT | TTC | 432 |
| Thr | Ile | Asp | Gly | Arg | Gly | Ala | Lys | Val | Glu | Ile | Ile | Asn | Ala | Gly | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| ACC | CTT | AAT | GGT | GTC | AAG | AAT | GTA | ATC | ATT | CAT | AAC | ATA | AAT | ATG | CAT | 480 |
| Thr | Leu | Asn | Gly | Val | Lys | Asn | Val | Ile | Ile | His | Asn | Ile | Asn | Met | His | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GAT | GTT | AAA | GTG | AAT | CCA | GGA | GGC | CTG | ATT | AAG | TCC | AAC | GAT | GGT | CCA | 528 |
| Asp | Val | Lys | Val | Asn | Pro | Gly | Gly | Leu | Ile | Lys | Ser | Asn | Asp | Gly | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| GCA | GCT | CCA | AGA | GCT | GGT | AGT | GAT | GGT | GAT | GCT | ATA | AGT | ATT | TCT | GGT | 576 |
| Ala | Ala | Pro | Arg | Ala | Gly | Ser | Asp | Gly | Asp | Ala | Ile | Ser | Ile | Ser | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| AGT | TCA | CAA | ATA | TGG | ATC | GAC | CAT | TGT | TCG | CTC | AGT | AAG | TCT | GTT | GAT | 624 |
| Ser | Ser | Gln | Ile | Trp | Ile | Asp | His | Cys | Ser | Leu | Ser | Lys | Ser | Val | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| GGG | CTG | GTA | GAT | GCC | AAG | CTC | GGC | ACC | ACA | CGC | TTA | ACC | GTT | TCC | AAC | 672 |
| Gly | Leu | Val | Asp | Ala | Lys | Leu | Gly | Thr | Thr | Arg | Leu | Thr | Val | Ser | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| AGC | TTA | TTC | ACC | CAA | CAC | CAG | TTT | GTA | CTA | TTA | TTC | GGG | GCT | GGT | GAC | 720 |
| Ser | Leu | Phe | Thr | Gln | His | Gln | Phe | Val | Leu | Leu | Phe | Gly | Ala | Gly | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GAA | AAT | ATT | GAA | GAT | AGA | GGC | ATG | CTA | GCA | ACG | GTC | GCT | TTC | AAC | ACG | 768 |
| Glu | Asn | Ile | Glu | Asp | Arg | Gly | Met | Leu | Ala | Thr | Val | Ala | Phe | Asn | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| TTC | ACT | GAT | AAC | GTT | GAC | CAA | AGA | ATG | CCT | AGA | TGT | CGA | CAT | GGG | TTT | 816 |
| Phe | Thr | Asp | Asn | Val | Asp | Gln | Arg | Met | Pro | Arg | Cys | Arg | His | Gly | Phe | |
| | | | 260 | | | | | 265 | | | | | 270 | | | |

| | | | | | | | | | | | | | | | | |
|---|---|---|---|---|---|---|---|---|---|---|---|---|---|---|---|---|
| TTC | CAA | GTC | GTT | AAC | AAC | AAC | TAT | GAT | AAA | TGG | GGA | TCG | TAT | GCC | ATC | 864 |
| Phe | Gln | Val | Val | Asn | Asn | Asn | Tyr | Asp | Lys | Trp | Gly | Ser | Tyr | Ala | Ile | |
| | | 275 | | | | | 280 | | | | | 285 | | | | |

| | | | | | | | | | | | | | | | | |
|---|---|---|---|---|---|---|---|---|---|---|---|---|---|---|---|---|
| GGT | GGT | AGC | GCG | TCC | CCA | ACC | ATA | CTC | AGC | CAA | GGG | AAC | AGA | TTC | TGC | 912 |
| Gly | Gly | Ser | Ala | Ser | Pro | Thr | Ile | Leu | Ser | Gln | Gly | Asn | Arg | Phe | Cys | |
| | 290 | | | | | 295 | | | | | 300 | | | | | |

```
GCC CCC GAT GAA CGC AGC AAG AAA AAT GTC CTA GGA AGG CAT GGT GAA        960
Ala Pro Asp Glu Arg Ser Lys Lys Asn Val Leu Gly Arg His Gly Glu
305                 310                 315                 320

GCC GCC GCA GAG TCG ATG AAG TGG AAC TGG AGA ACG AAT AAA GAC GTG       1008
Ala Ala Ala Glu Ser Met Lys Trp Asn Trp Arg Thr Asn Lys Asp Val
                325                 330                 335

CTT GAA AAT GGT GCT ATT TTT GTT GCA TCC GGG GTC GAT CCA GTG CTA       1056
Leu Glu Asn Gly Ala Ile Phe Val Ala Ser Gly Val Asp Pro Val Leu
            340                 345                 350

ACC CCT GAG CAA AGC GCA GGG ATG ATT CCA GCC GAA CCA GGA GAG TCC       1104
Thr Pro Glu Gln Ser Ala Gly Met Ile Pro Ala Glu Pro Gly Glu Ser
        355                 360                 365

GCT CTA AGC CTC ACT AGT AGT GCT GGT GTA CTC TCA TGC CAA CCC GGA       1152
Ala Leu Ser Leu Thr Ser Ser Ala Gly Val Leu Ser Cys Gln Pro Gly
370                 375                 380

GCA CCT TGC TAA GCA CCC GAC CAA TTA CTA AGC ACT TAT AAT               1194
Ala Pro Cys *
385

GA                                                                    1196

(2) INFORMATION FOR SEQ ID NO:72:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:72:

Leu Tyr Phe Thr Leu Ala Leu Val Thr Leu Leu Gln Pro Val Arg Ser
  1               5                  10                  15

Ala Glu Asp Leu Gln Glu Ile Leu Pro Val Asn Glu Thr Arg Arg Leu
              20                  25                  30

Thr Thr Ser Gly Ala Tyr Asn Ile Ile Asp Gly Cys Trp Arg Gly Lys
          35                  40                  45

Ala Asp Trp Ala Glu Asn Arg Lys Ala Leu Ala Asp Cys Ala Gln Gly
      50                  55                  60

Phe Gly Lys Gly Thr Val Gly Gly Lys Asp Gly Asp Ile Tyr Thr Val
 65                  70                  75                  80

Thr Ser Glu Leu Asp Asp Val Ala Asn Pro Lys Glu Gly Thr Leu
              85                  90                  95

Arg Phe Gly Ala Ala Gln Asn Arg Pro Leu Trp Ile Ile Phe Glu Arg
             100                 105                 110

Asp Met Val Ile Arg Leu Asp Lys Glu Met Val Val Asn Ser Asp Lys
         115                 120                 125

Thr Ile Asp Gly Arg Gly Ala Lys Val Glu Ile Ile Asn Ala Gly Phe
     130                 135                 140

Thr Leu Asn Gly Val Lys Asn Val Ile Ile His Asn Ile Asn Met His
145                 150                 155                 160

Asp Val Lys Val Asn Pro Gly Gly Leu Ile Lys Ser Asn Asp Gly Pro
                165                 170                 175

Ala Ala Pro Arg Ala Gly Ser Asp Gly Asp Ala Ile Ser Ile Ser Gly
            180                 185                 190

Ser Ser Gln Ile Trp Ile Asp His Cys Ser Leu Ser Lys Ser Val Asp
        195                 200                 205

Gly Leu Val Asp Ala Lys Leu Gly Thr Thr Arg Leu Thr Val Ser Asn
    210                 215                 220
```

```
Ser Leu Phe Thr Gln His Gln Phe Val Leu Leu Phe Gly Ala Gly Asp
225                 230                 235                 240

Glu Asn Ile Glu Asp Arg Gly Met Leu Ala Thr Val Ala Phe Asn Thr
            245                 250                 255

Phe Thr Asp Asn Val Asp Gln Arg Met Pro Arg Cys Arg His Gly Phe
        260                 265                 270

Phe Gln Val Val Asn Asn Asn Tyr Asp Lys Trp Gly Ser Tyr Ala Ile
    275                 280                 285

Gly Gly Ser Ala Ser Pro Thr Ile Leu Ser Gln Gly Asn Arg Phe Cys
    290                 295                 300

Ala Pro Asp Glu Arg Ser Lys Lys Asn Val Leu Gly Arg His Gly Glu
305                 310                 315                 320

Ala Ala Ala Glu Ser Met Lys Trp Asn Trp Arg Thr Asn Lys Asp Val
            325                 330                 335

Leu Glu Asn Gly Ala Ile Phe Val Ala Ser Gly Val Asp Pro Val Leu
            340                 345                 350

Thr Pro Glu Gln Ser Ala Gly Met Ile Pro Ala Glu Pro Gly Glu Ser
            355                 360                 365

Ala Leu Ser Leu Thr Ser Ser Ala Gly Val Leu Ser Cys Gln Pro Gly
370                 375                 380

Ala Pro Cys
385

(2) INFORMATION FOR SEQ ID NO:73:

(i) SEQUENCE CHARACTERISTICS:
        (A) LENGTH: 1349 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1323

(xi) SEQUENCE DESCRIPTION: SEQ ID NO:73:

ATG GGG ATC AAA CAC TGT TGT TAC ATC TTG TAT TTT ACC TTA GCC CTT      48
Met Gly Ile Lys His Cys Cys Tyr Ile Leu Tyr Phe Thr Leu Ala Leu
1               5                   10                  15

GTC ACT TTG CTG CAA CCT GTT CGT TCT GCA GAA GAT GTT GAA GAA TTC      96
Val Thr Leu Leu Gln Pro Val Arg Ser Ala Glu Asp Val Glu Glu Phe
            20                  25                  30

TTA CCT TCA GCT AAC GAA ACA AGG AGG AGC CTG AAA GCA TGT GAA GCA     144
Leu Pro Ser Ala Asn Glu Thr Arg Arg Ser Leu Lys Ala Cys Glu Ala
        35                  40                  45

CAC AAC ATT ATA GAC AAG TGC TGG AGG TGC AAA GCC GAT TGG GCG AAT     192
His Asn Ile Ile Asp Lys Cys Trp Arg Cys Lys Ala Asp Trp Ala Asn
    50                  55                  60

AAC CGA CAA GCG TTA GCC GAT TGT GCC CAA GGT TTT GCA AAG GGA ACC     240
Asn Arg Gln Ala Leu Ala Asp Cys Ala Gln Gly Phe Ala Lys Gly Thr
65                  70                  75                  80

TAC GGT GGA AAA CAT GGT GAT GTC TAC ACG GTC ACC AGT GAT AAA GAT     288
Tyr Gly Gly Lys His Gly Asp Val Tyr Thr Val Thr Ser Asp Lys Asp
                85                  90                  95

GAT GAT GTT GCA AAT CCA AAA GAA GGC ACA CTC CGG TTT GCT GCT GCC     336
Asp Asp Val Ala Asn Pro Lys Glu Gly Thr Leu Arg Phe Ala Ala Ala
            100                 105                 110
```

```
                                                -continued

CAA AAC AGG CCC TTG TGG ATC ATT TTT AAA AGA AAT ATG GTG ATT CAT      384
Gln Asn Arg Pro Leu Trp Ile Ile Phe Lys Arg Asn Met Val Ile His
        115                 120                 125

TTG AAT CAA GAG CTT GTC GTA AAC AGC GAC AAG ACC ATC GAT GGC CGA      432
Leu Asn Gln Glu Leu Val Val Asn Ser Asp Lys Thr Ile Asp Gly Arg
    130                 135                 140

GGG GTG AAA GTT AAC ATC GTT AAC GCC GGT CTC ACC CTC ATG AAT GTC      480
Gly Val Lys Val Asn Ile Val Asn Ala Gly Leu Thr Leu Met Asn Val
145                 150                 155                 160

AAG AAT ATA ATC ATT CAT AAC ATA AAT ATC CAT GAT ATT AAA GTT TGT      528
Lys Asn Ile Ile Ile His Asn Ile Asn Ile His Asp Ile Lys Val Cys
                165                 170                 175

CCA GGA GGC ATG ATT AAG TCC AAC GAT GGT CCA CCA ATT TTA AGA CAA      576
Pro Gly Gly Met Ile Lys Ser Asn Asp Gly Pro Pro Ile Leu Arg Gln
            180                 185                 190

CAA AGT GAT GGT GAT GCT ATA AAT GTT GCT GGT AGT TCA CAA ATA TGG      624
Gln Ser Asp Gly Asp Ala Ile Asn Val Ala Gly Ser Ser Gln Ile Trp
        195                 200                 205

ATC GAC CAT TGC TCG CTC AGT AAG GCT TCC GAT GGG CTG CTC GAT ATC      672
Ile Asp His Cys Ser Leu Ser Lys Ala Ser Asp Gly Leu Leu Asp Ile
    210                 215                 220

ACC CTC GGC AGC TCA CAC GTG ACC GTT TCC AAC TGC AAA TTC ACC CAA      720
Thr Leu Gly Ser Ser His Val Thr Val Ser Asn Cys Lys Phe Thr Gln
225                 230                 235                 240

CAC CAA TTT GTA TTA TTG CTC GGG GCT GAT GAC ACC CAT TAT CAA GAT      768
His Gln Phe Val Leu Leu Leu Gly Ala Asp Asp Thr His Tyr Gln Asp
                245                 250                 255

AAA GGC ATG CTA GCA ACG GTA GCA TTC AAC ATG TTC ACC GAT CAC GTT      816
Lys Gly Met Leu Ala Thr Val Ala Phe Asn Met Phe Thr Asp His Val
            260                 265                 270

GAC CAA AGA ATG CCT AGA TGT AGA TTT GGG TTT TTC CAA GTC GTT AAC      864
Asp Gln Arg Met Pro Arg Cys Arg Phe Gly Phe Phe Gln Val Val Asn
        275                 280                 285

AAC AAC TAC GAC AGA TGG GGA ACG TAC GCC ATC GGT GGT AGC TCG GCC      912
Asn Asn Tyr Asp Arg Trp Gly Thr Tyr Ala Ile Gly Gly Ser Ser Ala
    290                 295                 300

CCA ACT ATA CTC AGC CAA GGG AAC AGA TTC TTC GCC CCC GAT GAT ATC      960
Pro Thr Ile Leu Ser Gln Gly Asn Arg Phe Phe Ala Pro Asp Asp Ile
305                 310                 315                 320

ATC AAG AAA AAT GTC TTA GCG AGG ACT GGT ACT GGC AAC GCA GAG TCG     1008
Ile Lys Lys Asn Val Leu Ala Arg Thr Gly Thr Gly Asn Ala Glu Ser
                325                 330                 335

ATG TCG TGG AAC TGG AGA ACA GAT AGA GAC TTG CTT GAA AAT GGT GCT     1056
Met Ser Trp Asn Trp Arg Thr Asp Arg Asp Leu Leu Glu Asn Gly Ala
            340                 345                 350

ATT TTT CTC CCA TCC GGG TCT GAT CCA GTG CTA ACC CCT GAG CAA AAA     1104
Ile Phe Leu Pro Ser Gly Ser Asp Pro Val Leu Thr Pro Glu Gln Lys
        355                 360                 365

GCA GGG ATG ATT CCA GCT GAA CCA GGA GAA GCC GTT CTA AGA CTC ACT     1152
Ala Gly Met Ile Pro Ala Glu Pro Gly Glu Ala Val Leu Arg Leu Thr
    370                 375                 380

AGT AGT GCT GGT GTA CTC TCA TGC CAT CAA GGA GCA CCT TGC TAA GCA     1200
Ser Ser Ala Gly Val Leu Ser Cys His Gln Gly Ala Pro Cys  *  Ala
385                 390                 395                 400

CCT GGC CAA TTC CTA AGC TTT TAT AAT AAT CAT AAA TAC TTA TTT TAT     1248
Pro Gly Gln Phe Leu Ser Phe Tyr Asn Asn His Lys Tyr Leu Phe Tyr
                405                 410                 415

TTT ATT TTT GAT ATT TTA TAT GAA CCA TTA CGT TCA AGT ACT CTA TTA     1296
Phe Ile Phe Asp Ile Leu Tyr Glu Pro Leu Arg Ser Ser Thr Leu Leu
            420                 425                 430
```

```
ACA TGT TTT AAA TTC ATA AGA GTT TAT TGA TAA AAA AAA AAA AAA CCG    1344
Thr Cys Phe Lys Phe Ile Arg Val Tyr *   *
        435                 440

AAT TC                                                             1349
```

(2) INFORMATION FOR SEQ ID NO:74:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:74:

```
Met Gly Ile Lys His Cys Cys Tyr Ile Leu Tyr Phe Thr Leu Ala Leu
 1               5                  10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
           100                 105                 110

Gln Asn Arg Pro Leu Trp Ile Ile Phe Lys Arg Asn Met Val Ile His
       115                 120                 125

Leu Asn Gln Glu Leu Val Val Asn Ser Asp Lys Thr Ile Asp Gly Arg
   130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
           180                 185                 190

Gln Ser Asp Gly Asp Ala Ile Asn Val Ala Gly Ser Ser Gln Ile Trp
       195                 200                 205

Ile Asp His Cys Ser Leu Ser Lys Ala Ser Asp Gly Leu Leu Asp Ile
   210                 215                 220

Thr Leu Gly Ser Ser His Val Thr Val Ser Asn Cys Lys Phe Thr Gln
225                 230                 235                 240

His Gln Phe Val Leu Leu Gly Ala Asp Asp Thr His Tyr Gln Asp
                245                 250                 255

Lys Gly Met Leu Ala Thr Val Ala Phe Asn Met Phe Thr Asp His Val
           260                 265                 270

Asp Gln Arg Met Pro Arg Cys Arg Phe Gly Phe Gln Val Val Asn
       275                 280                 285

Asn Asn Tyr Asp Arg Trp Gly Thr Tyr Ala Ile Gly Ser Ser Ala
   290                 295                 300

Pro Thr Ile Leu Ser Gln Gly Asn Arg Phe Phe Ala Pro Asp Asp Ile
305                 310                 315                 320
```

```
Ile Lys Lys Asn Val Leu Ala Arg Thr Gly Thr Gly Asn Ala Glu Ser
            325                 330                 335

Met Ser Trp Asn Trp Arg Thr Asp Arg Asp Leu Leu Glu Asn Gly Ala
            340                 345                 350

Ile Phe Leu Pro Ser Gly Ser Asp Pro Val Leu Thr Pro Glu Gln Lys
            355                 360                 365

Ala Gly Met Ile Pro Ala Glu Pro Gly Glu Ala Val Leu Arg Leu Thr
370                 375                 380

Ser Ser Ala Gly Val Leu Ser Cys His Gln Gly Ala Pro Cys
385                 390                 395
```

(2) INFORMATION FOR SEQ ID NO:75:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1302

(xi) SEQUENCE DESCRIPTION: SEQ ID NO:75:

```
ATG GGG ATC AAA CAA TGT TGT TAC ATC TTG TAT TTT ACC TTA GCA CTT      48
Met Gly Ile Lys Gln Cys Cys Tyr Ile Leu Tyr Phe Thr Leu Ala Leu
1               5                   10                  15

GTC GCT TTG CTG CAA CCT GTT CGT TCT GCC GAA GGT GTC GGG GAA ATC      96
Val Ala Leu Leu Gln Pro Val Arg Ser Ala Glu Gly Val Gly Glu Ile
                20                  25                  30

TTA CCT TCA GTT AAC GAA ACG AGG AGC CTG CAA GCA TGT GAA GCA CTC     144
Leu Pro Ser Val Asn Glu Thr Arg Ser Leu Gln Ala Cys Glu Ala Leu
            35                  40                  45

AAC ATT ATA GAC AAG TGC TGG AGG GGC AAA GCC GAT TGG GAG AAC AAC     192
Asn Ile Ile Asp Lys Cys Trp Arg Gly Lys Ala Asp Trp Glu Asn Asn
        50                  55                  60

CGA CAA GCG TTA GCC GAC TGT GCC CAA GGT TTT GCA AAG GGA ACC TAC     240
Arg Gln Ala Leu Ala Asp Cys Ala Gln Gly Phe Ala Lys Gly Thr Tyr
65                  70                  75                  80

GGC GGA AAA TGG GGT GAT GTC TAC ACG GTC ACC AGC AAT CTA GAT GAT     288
Gly Gly Lys Trp Gly Asp Val Tyr Thr Val Thr Ser Asn Leu Asp Asp
                85                  90                  95

GAT GTT GCA AAT CCA AAA GAA GGC ACA CTC CGG TTT GCT GCC GCC CAA     336
Asp Val Ala Asn Pro Lys Glu Gly Thr Leu Arg Phe Ala Ala Ala Gln
            100                 105                 110

AAC AGG CCC TTG TGG ATC ATT TTT AAA AAT GAT ATG GTG ATT AAT TTG     384
Asn Arg Pro Leu Trp Ile Ile Phe Lys Asn Asp Met Val Ile Asn Leu
        115                 120                 125

AAT CAA GAG CTT GTC GTA AAC AGC GAC AAG ACC ATC GAT GGC CGA GGG     432
Asn Gln Glu Leu Val Val Asn Ser Asp Lys Thr Ile Asp Gly Arg Gly
    130                 135                 140

GTG AAA GTT GAA ATC ATT AAC GGA GGT CTC ACC CTC ATG AAT GTC AAG     480
Val Lys Val Glu Ile Ile Asn Gly Gly Leu Thr Leu Met Asn Val Lys
145                 150                 155                 160

AAT ATA ATC ATT CAT AAC ATA AAT ATC CAT GAT GTT AAA GTG CTT CCA     528
Asn Ile Ile Ile His Asn Ile Asn Ile His Asp Val Lys Val Leu Pro
                165                 170                 175

GGA GGC ATG ATT AAG TCC AAC GAT GGT CCA CCA ATT TTA AGA CAA GCA     576
Gly Gly Met Ile Lys Ser Asn Asp Gly Pro Pro Ile Leu Arg Gln Ala
            180                 185                 190
```

```
AGT GAT GGG GAT ACT ATA AAT GTT GCT GGT AGT TCC CAA ATA TGG ATA      624
Ser Asp Gly Asp Thr Ile Asn Val Ala Gly Ser Ser Gln Ile Trp Ile
            195                 200                 205

GAC CAT TGC TCA CTC AGC AAG TCT TTC GAT GGG CTG GTC GAT GTC ACC      672
Asp His Cys Ser Leu Ser Lys Ser Phe Asp Gly Leu Val Asp Val Thr
        210                 215                 220

CTC GGT AGC ACA CAC GTG ACC ATT TCC AAC TGC AAA TTC ACC CAA CAG      720
Leu Gly Ser Thr His Val Thr Ile Ser Asn Cys Lys Phe Thr Gln Gln
225                 230                 235                 240

TCA AAA GCA ATA TTG TTG GGA GCA GAT GAC ACC CAT GTT CAA GAT AAA      768
Ser Lys Ala Ile Leu Leu Gly Ala Asp Asp Thr His Val Gln Asp Lys
            245                 250                 255

GGA ATG CTA GCA ACG GTC GCT TTC AAC ATG TTC ACC GAT AAC GTT GAC      816
Gly Met Leu Ala Thr Val Ala Phe Asn Met Phe Thr Asp Asn Val Asp
        260                 265                 270

CAA AGA ATG CCT AGA TGT CGA TTT GGG TTT TTC CAA GTT GTT AAC AAC      864
Gln Arg Met Pro Arg Cys Arg Phe Gly Phe Phe Gln Val Val Asn Asn
    275                 280                 285

AAC TAC GAC AGA TGG GGA ACG TAC GCC ATA GGT GGT AGC TCG GCC CCA      912
Asn Tyr Asp Arg Trp Gly Thr Tyr Ala Ile Gly Gly Ser Ser Ala Pro
    290                 295                 300

ACT ATA CTC TGC CAA GGG AAC AGA TTC TTG GCC CCT GAT GAT CAG ATC      960
Thr Ile Leu Cys Gln Gly Asn Arg Phe Leu Ala Pro Asp Asp Gln Ile
305                 310                 315                 320

AAG AAA AAT GTC CTA GCG AGG ACT GGT ACA GGC GCT GCT GAG TCG ATG     1008
Lys Lys Asn Val Leu Ala Arg Thr Gly Thr Gly Ala Ala Glu Ser Met
            325                 330                 335

GCG TGG AAC TGG AGA TCT GAT AAA GAC TTG CTT GAA AAT GGT GCT ATT     1056
Ala Trp Asn Trp Arg Ser Asp Lys Asp Leu Leu Glu Asn Gly Ala Ile
        340                 345                 350

TTT GTT ACA TCT GGG TCT GAT CCA GTG CTA ACC CCT GTT CAA AGC GCA     1104
Phe Val Thr Ser Gly Ser Asp Pro Val Leu Thr Pro Val Gln Ser Ala
    355                 360                 365

GGG ATG ATT CCA GCT GAA CCA GGA GAA GCC GCT ATA AAA CTC ACT AGT     1152
Gly Met Ile Pro Ala Glu Pro Gly Glu Ala Ala Ile Lys Leu Thr Ser
    370                 375                 380

AGT GCT GGT GTA TTC TCA TGC CGT CCT GGA GCA CCT TGC TAA GCA CCC     1200
Ser Ala Gly Val Phe Ser Cys Arg Pro Gly Ala Pro Cys  *  Ala Pro
385                 390                 395                 400

TGC CAA TTC TCC TAA GCT TTT GCA ATG ATC AAA AAT ACT TTT TTA TTT     1248
Cys Gln Phe Ser  *  Ala Phe Ala Met Ile Lys Asn Thr Phe Leu Phe
                405                 410                 415

TAT TTT TAA TAT TTT ATA TGT ACT GGA AAT GAA CCA TTA CCT TCT AGT     1296
Tyr Phe  *  Tyr Phe Ile Cys Thr Gly Asn Glu Pro Leu Pro Ser Ser
            420                 425                 430

ACT CTA TAA CAT GTT TTG CAT TTA                                     1320
Thr Leu  *
        435

(2) INFORMATION FOR SEQ ID NO:76:

(i) SEQUENCE CHARACTERISTICS:
          (A) LENGTH: 397 amino acids
          (B) TYPE: amino acid
          (D) TOPOLOGY: linear (ii) MOLECULE TYPE: protein (xi) SEQUENCE DESCRIPTION: SEQ ID NO:76:

Met Gly Ile Lys Gln Cys Cys Tyr Ile Leu Tyr Phe Thr Leu Ala Leu
 1               5                  10                  15
```

```
Val Ala Leu Leu Gln Pro Val Arg Ser Ala Glu Gly Val Gly Glu Ile
             20                  25                  30

Leu Pro Ser Val Asn Glu Thr Arg Ser Leu Gln Ala Cys Glu Ala Leu
             35                  40                  45

Asn Ile Ile Asp Lys Cys Trp Arg Gly Lys Ala Asp Trp Glu Asn Asn
             50                  55                  60

Arg Gln Ala Leu Ala Asp Cys Ala Gln Gly Phe Ala Lys Gly Thr Tyr
 65                  70                  75                  80

Gly Gly Lys Trp Gly Asp Val Tyr Thr Val Thr Ser Asn Leu Asp Asp
                 85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
            115                 120                 125

Asn Gln Glu Leu Val Val Asn Ser Asp Lys Thr Ile Asp Gly Arg Gly
            130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
            165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
            195                 200                 205

Asp His Cys Ser Leu Ser Lys Ser Phe Asp Gly Leu Val Asp Val Thr
            210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
            245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Phe Gln Val Val Asn Asn
            275                 280                 285

Asn Tyr Asp Arg Trp Gly Thr Tyr Ala Ile Gly Gly Ser Ser Ala Pro
            290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
            325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
            355                 360                 365

Gly Met Ile Pro Ala Glu Pro Gly Glu Ala Ala Ile Lys Leu Thr Ser
            370                 375                 380

Ser Ala Gly Val Phe Ser Cys Arg Pro Gly Ala Pro Cys
385                 390                 395
```

(2) INFORMATION FOR SEQ ID NO:77:

(i) SEQUENCE CHARACTERISTICS:
        (A) LENGTH: 1160 base pairs
        (B) TYPE: nucleic acid -continued

```
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..1148

(xi) SEQUENCE DESCRIPTION: SEQ ID NO:77:

TTG TAT TTT ACC TTA GCC CTT GTC ACT TTG CTG CAA CCT GTT CGT TCT        48
Leu Tyr Phe Thr Leu Ala Leu Val Thr Leu Leu Gln Pro Val Arg Ser
 1               5                  10                  15

GCC GAA GAT CTC CAG GAA ATC TTA CCT TCA GCT AAC GAA ACA AGG AGC        96
Ala Glu Asp Leu Gln Glu Ile Leu Pro Ser Ala Asn Glu Thr Arg Ser
             20                  25                  30

CTG ACA ACA TGT GGA ACA TAC AAC ATT ATA GAC GGG TGC TGG AGG GGC       144
Leu Thr Thr Cys Gly Thr Tyr Asn Ile Ile Asp Gly Cys Trp Arg Gly
         35                  40                  45

AAA GCC GAT TGG GCG GAA AAC CGA AAA GCG TTA GCC GAT TGT GCC CAA       192
Lys Ala Asp Trp Ala Glu Asn Arg Lys Ala Leu Ala Asp Cys Ala Gln
     50                  55                  60

GGT TTT GCA AAG GGA ACA ATC GGC GGA AAA GAT GGT GAT ATA TAC ACG       240
Gly Phe Ala Lys Gly Thr Ile Gly Gly Lys Asp Gly Asp Ile Tyr Thr
 65                  70                  75                  80

GTC ACC AGT GAG CTA GAT GAT GAT GTT GCA AAT CCA AAA GAA GGC ACA       288
Val Thr Ser Glu Leu Asp Asp Asp Val Ala Asn Pro Lys Glu Gly Thr
                 85                  90                  95

CTC CGG TTT GGT GCC GCC CAA AAC AGG CCC TTG TGG ATT ATT TTT GAA       336
Leu Arg Phe Gly Ala Ala Gln Asn Arg Pro Leu Trp Ile Ile Phe Glu
             100                 105                 110

AGA GAT ATG GTG ATT CGT TTG GAT AGA GAG TTG GCT ATA AAC AAC GAC       384
Arg Asp Met Val Ile Arg Leu Asp Arg Glu Leu Ala Ile Asn Asn Asp
         115                 120                 125

AAG ACC ATC GAT GGC CGA GGG GCG AAA GTT GAA ATC ATT AAC GCT GGT       432
Lys Thr Ile Asp Gly Arg Gly Ala Lys Val Glu Ile Ile Asn Ala Gly
     130                 135                 140

TTC GCC ATC TAT AAT GTC AAG AAT ATA ATC ATT CAT AAC ATA ATT ATG       480
Phe Ala Ile Tyr Asn Val Lys Asn Ile Ile Ile His Asn Ile Ile Met
145                 150                 155                 160

CAT GAT ATT GTA GTG AAT CCA GGA GGC CTG ATT AAG TCC CAC GAT GGT       528
His Asp Ile Val Val Asn Pro Gly Gly Leu Ile Lys Ser His Asp Gly
                 165                 170                 175

CCA CCA GTT CCA AGA AAG GGT AGT GAT GGT GAT GCT ATA GGT ATT TCT       576
Pro Pro Val Pro Arg Lys Gly Ser Asp Gly Asp Ala Ile Gly Ile Ser
             180                 185                 190

GGT GGT TCA CAA ATA TGG ATC GAC CAT TGC TCC CTC AGT AAG GCT GTT       624
Gly Gly Ser Gln Ile Trp Ile Asp His Cys Ser Leu Ser Lys Ala Val
         195                 200                 205

GAT GGG CTA ATC GAT GCT AAA CAC GGC AGC ACA CAC TTC ACC GTT TCT       672
Asp Gly Leu Ile Asp Ala Lys His Gly Ser Thr His Phe Thr Val Ser
     210                 215                 220

AAC TGC TTA TTC ACC CAA CAC CAA TAT TTA TTA TTG TTC TGG GAT TTT       720
Asn Cys Leu Phe Thr Gln His Gln Tyr Leu Leu Leu Phe Trp Asp Phe
225                 230                 235                 240

GAC GAG CGA GGC ATG CTA TGT ACG GTC GCA TTC AAC AAG TTC ACT GAT       768
Asp Glu Arg Gly Met Leu Cys Thr Val Ala Phe Asn Lys Phe Thr Asp
                 245                 250                 255

AAC GTT GAC CAA AGA ATG CCT AAC TTA CGA CAT GGG TTT GTC CAA GTC       816
Asn Val Asp Gln Arg Met Pro Asn Leu Arg His Gly Phe Val Gln Val
             260                 265                 270
```

```
GTT AAC AAC AAC TAC GAA AGA TGG GGA TCG TAC GCC CTC GGT GGT AGC      864
Val Asn Asn Asn Tyr Glu Arg Trp Gly Ser Tyr Ala Leu Gly Gly Ser
            275                 280                 285

GCA GGC CCA ACC ATA CTT AGC CAA GGG AAC AGA TTC TTA GCC TCC GAT      912
Ala Gly Pro Thr Ile Leu Ser Gln Gly Asn Arg Phe Leu Ala Ser Asp
    290                 295                 300

ATC AAG AAA GAG GTC GTA GGG AGG TAT GGT GAA TCC GCC ATG TCA GAG      960
Ile Lys Lys Glu Val Val Gly Arg Tyr Gly Glu Ser Ala Met Ser Glu
305                 310                 315                 320

TCG ATT AAT TGG AAC TGG AGA TCG TAT ATG GAC GTA TTT GAA AAT GGT     1008
Ser Ile Asn Trp Asn Trp Arg Ser Tyr Met Asp Val Phe Glu Asn Gly
            325                 330                 335

GCT ATT TTT GTT CCA TCC GGG GTT GAT CCA GTG CTA ACC CCT GAG CAA     1056
Ala Ile Phe Val Pro Ser Gly Val Asp Pro Val Leu Thr Pro Glu Gln
    340                 345                 350

AAC GCA GGG ATG ATT CCA GCC GAA CCA GGA GAA GCC GTT CTA AGA CTC     1104
Asn Ala Gly Met Ile Pro Ala Glu Pro Gly Glu Ala Val Leu Arg Leu
                355                 360                 365

ACT AGT AGT GCT GGT GTC CTC TCA TGC CAA CCT GGA GCA CCT TGC TAA     1152
Thr Ser Ser Ala Gly Val Leu Ser Cys Gln Pro Gly Ala Pro Cys *
370                 375                 380

GCA CTG CA                                                          1160
```

(2) INFORMATION FOR SEQ ID NO:78:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:78:

```
Leu Tyr Phe Thr Leu Ala Leu Val Thr Leu Leu Gln Pro Val Arg Ser
  1               5                  10                  15

Ala Glu Asp Leu Gln Glu Ile Leu Pro Ser Ala Asn Glu Thr Arg Ser
             20                  25                  30

Leu Thr Thr Cys Gly Thr Tyr Asn Ile Ile Asp Gly Cys Trp Arg Gly
         35                  40                  45

Lys Ala Asp Trp Ala Glu Asn Arg Lys Ala Leu Ala Asp Cys Ala Gln
     50                  55                  60

Gly Phe Ala Lys Gly Thr Ile Gly Gly Lys Asp Gly Asp Ile Tyr Thr
 65                  70                  75                  80

Val Thr Ser Glu Leu Asp Asp Val Ala Asn Pro Lys Glu Gly Thr
                 85                  90                  95

Leu Arg Phe Gly Ala Ala Gln Asn Arg Pro Leu Trp Ile Ile Phe Glu
                100                 105                 110

Arg Asp Met Val Ile Arg Leu Asp Arg Glu Leu Ala Ile Asn Asn Asp
            115                 120                 125

Lys Thr Ile Asp Gly Arg Gly Ala Lys Val Glu Ile Ile Asn Ala Gly
        130                 135                 140

Phe Ala Ile Tyr Asn Val Lys Asn Ile Ile Ile His Asn Ile Ile Met
145                 150                 155                 160

His Asp Ile Val Val Asn Pro Gly Gly Leu Ile Lys Ser His Asp Gly
                165                 170                 175

Pro Pro Val Pro Arg Lys Gly Ser Asp Gly Asp Ala Ile Gly Ile Ser
            180                 185                 190
```

```
Gly Gly Ser Gln Ile Trp Ile Asp His Cys Ser Leu Ser Lys Ala Val
        195                 200                 205

Asp Gly Leu Ile Asp Ala Lys His Gly Ser Thr His Phe Thr Val Ser
        210                 215                 220

Asn Cys Leu Phe Thr Gln His Gln Tyr Leu Leu Phe Trp Asp Phe
225                 230                 235                 240

Asp Glu Arg Gly Met Leu Cys Thr Val Ala Phe Asn Lys Phe Thr Asp
                245                 250                 255

Asn Val Asp Gln Arg Met Pro Asn Leu Arg His Gly Phe Val Gln Val
            260                 265                 270

Val Asn Asn Tyr Glu Arg Trp Gly Ser Tyr Ala Leu Gly Gly Ser
        275                 280                 285

Ala Gly Pro Thr Ile Leu Ser Gln Gly Asn Arg Phe Leu Ala Ser Asp
        290                 295                 300

Ile Lys Lys Glu Val Val Gly Arg Tyr Gly Ser Ala Met Ser Glu
305                 310                 315                 320

Ser Ile Asn Trp Asn Trp Arg Ser Tyr Met Asp Val Phe Glu Asn Gly
                325                 330                 335

Ala Ile Phe Val Pro Ser Gly Val Asp Pro Val Leu Thr Pro Glu Gln
            340                 345                 350

Asn Ala Gly Met Ile Pro Ala Glu Pro Gly Glu Ala Val Leu Arg Leu
        355                 360                 365

Thr Ser Ser Ala Gly Val Leu Ser Cys Gln Pro Gly Ala Pro Cys
        370                 375                 380
```

(2) INFORMATION FOR SEQ ID NO:79:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1366

(xi) SEQUENCE DESCRIPTION: SEQ ID NO:79:

```
TTG TAT TTT ACC TTA GCA CTT GTC ACT TTG GTG CAA GCT GGA CGT CTT        48
Leu Tyr Phe Thr Leu Ala Leu Val Thr Leu Val Gln Ala Gly Arg Leu
1               5                   10                  15

GGC GAA GAG GTC GAC ATC TTA CCT TCA CCT AAC GAT ACA AGG AGG AGC        96
Gly Glu Glu Val Asp Ile Leu Pro Ser Pro Asn Asp Thr Arg Arg Ser
            20                  25                  30

CTG CAA GGA TGT GAA GCA CAC AAC ATT ATA GAC AAG TGT TGG AGG TGC       144
Leu Gln Gly Cys Glu Ala His Asn Ile Ile Asp Lys Cys Trp Arg Cys
        35                  40                  45

AAA CCC GAT TGG GCG GAG AAC CGA CAA GCG TTA GGC GAT TGT GCG CAA       192
Lys Pro Asp Trp Ala Glu Asn Arg Gln Ala Leu Gly Asp Cys Ala Gln
    50                  55                  60

GGT TTT GGA AAG GCA ACT CAC GGC GGA AAA TGG GGT GAT ATC TAC ATG       240
Gly Phe Gly Lys Ala Thr His Gly Gly Lys Trp Gly Asp Ile Tyr Met
65                  70                  75                  80

GTC ACA AGT GAT CAG GAT GAT GAT GTT GTA AAT CCA AAA GAA GGC ACA       288
Val Thr Ser Asp Gln Asp Asp Asp Val Val Asn Pro Lys Glu Gly Thr
                85                  90                  95
```

```
CTC CGG TTC GGT GCT ACC CAG GAC AGG CCC TTG TGG ATC ATT TTT CAA        336
Leu Arg Phe Gly Ala Thr Gln Asp Arg Pro Leu Trp Ile Ile Phe Gln
            100                 105                 110

AGA GAT ATG ATT ATT TAT TTG CAA CAA GAG ATG GTC GTA ACC AGC GAC        384
Arg Asp Met Ile Ile Tyr Leu Gln Gln Glu Met Val Val Thr Ser Asp
            115                 120                 125

ACG ACC ATT GAT GGT CGA GGG GCG AAA GTT GAG CTC GTT TAT GGA GGT        432
Thr Thr Ile Asp Gly Arg Gly Ala Lys Val Glu Leu Val Tyr Gly Gly
    130                 135                 140

ATC ACC CTC ATG AAT GTC AAG AAT GTA ATC ATT CAC AAC ATA GAT ATC        480
Ile Thr Leu Met Asn Val Lys Asn Val Ile Ile His Asn Ile Asp Ile
145                 150                 155                 160

CAT GAT GTT AGA GTG CTT CCA GGA GGT AGG ATT AAG TCC AAT GGT GGT        528
His Asp Val Arg Val Leu Pro Gly Gly Arg Ile Lys Ser Asn Gly Gly
                165                 170                 175

CCA GCC ATA CCA AGA CAT CAG AGT GAT GGT GAT GCT ATC CAT GTT ACG        576
Pro Ala Ile Pro Arg His Gln Ser Asp Gly Asp Ala Ile His Val Thr
            180                 185                 190

GGT AGT TCA GAC ATA TGG ATC GAC CAT TGC ACG CTC AGT AAG TCA TTT        624
Gly Ser Ser Asp Ile Trp Ile Asp His Cys Thr Leu Ser Lys Ser Phe
            195                 200                 205

GAT GGG CTC GTC GAT GTC AAC TGG GGC AGC ACA GGA GTA ACC ATT TCC        672
Asp Gly Leu Val Asp Val Asn Trp Gly Ser Thr Gly Val Thr Ile Ser
    210                 215                 220

AAC TGC AAA TTC ACC CAC CAC GAA AAA GCT GTT TTG CTC GGG GCT AGT        720
Asn Cys Lys Phe Thr His His Glu Lys Ala Val Leu Leu Gly Ala Ser
225                 230                 235                 240

GAC ACG CAT TTT CAA GAT CTG AAA ATG CAT GTA ACG CTT GCA TAC AAC        768
Asp Thr His Phe Gln Asp Leu Lys Met His Val Thr Leu Ala Tyr Asn
                245                 250                 255

ATC TTC ACC AAT ACC GTT CAC GAA AGA ATG CCC AGA TGC CGA TTT GGG        816
Ile Phe Thr Asn Thr Val His Glu Arg Met Pro Arg Cys Arg Phe Gly
            260                 265                 270

TTT TTC CAA ATC GTT AAC AAC TTC TAC GAC AGA TGG GAT AAG TAC GCC        864
Phe Phe Gln Ile Val Asn Asn Phe Tyr Asp Arg Trp Asp Lys Tyr Ala
            275                 280                 285

ATC GGT GGT AGC TCG AAC CCT ACT ATT CTC AGC CAA GGG AAC AAA TTC        912
Ile Gly Gly Ser Ser Asn Pro Thr Ile Leu Ser Gln Gly Asn Lys Phe
    290                 295                 300

GTG GCC CCC GAT TTC ATT TAC AAG AAA AAC GTC TGT CTA AGG ACT GGT        960
Val Ala Pro Asp Phe Ile Tyr Lys Lys Asn Val Cys Leu Arg Thr Gly
305                 310                 315                 320

GCA CAG GAG CCA GAA TGG ATG ACT TGG AAC TGG AGA ACA CAA AAC GAC       1008
Ala Gln Glu Pro Glu Trp Met Thr Trp Asn Trp Arg Thr Gln Asn Asp
                325                 330                 335

GTG CTT GAA AAT GGT GCT ATC TTT GTG GCA TCT GGG TCT GAT CCA GTG       1056
Val Leu Glu Asn Gly Ala Ile Phe Val Ala Ser Gly Ser Asp Pro Val
            340                 345                 350

CTA ACC GCT GAA CAA AAT GCA GGC ATG ATG CAA GCT GAA CCG GGA GAT       1104
Leu Thr Ala Glu Gln Asn Ala Gly Met Met Gln Ala Glu Pro Gly Asp
            355                 360                 365

ATG GTT CCA CAA CTC ACC ATG AAT GCA GGT GTA CTC ACA TGC TCG CCT       1152
Met Val Pro Gln Leu Thr Met Asn Ala Gly Val Leu Thr Cys Ser Pro
    370                 375                 380

GGA GCA CCT TGC TAA GCA CCT GGC CAA TTC CTA TGC AAC GAT CAT AAA       1200
Gly Ala Pro Cys  *  Ala Pro Gly Gln Phe Leu Cys Asn Asp His Lys
385                 390                 395                 400
```

```
TAC TTG CTC ACC ATA AGT GTT CAT TTG ATT AGA TTT GGA CAC GAA TGA                1248
Tyr Leu Leu Thr Ile Ser Val His Leu Ile Arg Phe Gly His Glu  *
                405                 410                 415

TGT AAC CGA TTC GTC TGA ATT ATG ATT TGT TTT GAT TCT CAG TTT CAT                1296
Cys Asn Arg Phe Val  *  Ile Met Ile Cys Phe Asp Ser Gln Phe His
                420                 425                 430

AAT ATG GCT TCT TGA GAG CAA AAT TAG AGA AGA GTG TCT TTG ATC AAC                1344
Asn Met Ala Ser  *  Glu Gln Asn  *  Arg Arg Val Ser Leu Ile Asn
                435                 440                 445

TAC ATT TTA TGG TTT TTA TAT T AA                                               1368
Tyr Ile Leu Trp Phe Leu Tyr
            450             455
```

(2) INFORMATION FOR SEQ ID NO:80:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO:80:

```
Leu Tyr Phe Thr Leu Ala Leu Val Thr Leu Val Gln Ala Gly Arg Leu
 1               5                  10                  15

Gly Glu Glu Val Asp Ile Leu Pro Ser Pro Asn Asp Thr Arg Arg Ser
                20                  25                  30

Leu Gln Gly Cys Glu Ala His Asn Ile Ile Asp Lys Cys Trp Arg Cys
            35                  40                  45

Lys Pro Asp Trp Ala Glu Asn Arg Gln Ala Leu Gly Asp Cys Ala Gln
        50                  55                  60

Gly Phe Gly Lys Ala Thr His Gly Gly Lys Trp Gly Asp Ile Tyr Met
 65                 70                  75                  80

Val Thr Ser Asp Gln Asp Asp Val Val Asn Pro Lys Glu Gly Thr
                85                  90                  95

Leu Arg Phe Gly Ala Thr Gln Asp Arg Pro Leu Trp Ile Ile Phe Gln
                100                 105                 110

Arg Asp Met Ile Ile Tyr Leu Gln Gln Glu Met Val Val Thr Ser Asp
                115                 120                 125

Thr Thr Ile Asp Gly Arg Gly Ala Lys Val Glu Leu Val Tyr Gly Gly
        130                 135                 140

Ile Thr Leu Met Asn Val Lys Asn Val Ile His Asn Ile Asp Ile
145                 150                 155                 160

His Asp Val Arg Val Leu Pro Gly Gly Arg Ile Lys Ser Asn Gly Gly
                165                 170                 175

Pro Ala Ile Pro Arg His Gln Ser Asp Gly Asp Ala Ile His Val Thr
                180                 185                 190

Gly Ser Ser Asp Ile Trp Ile Asp His Cys Thr Leu Ser Lys Ser Phe
            195                 200                 205

Asp Gly Leu Val Asp Val Asn Trp Gly Ser Thr Gly Val Thr Ile Ser
        210                 215                 220

Asn Cys Lys Phe Thr His His Glu Lys Ala Val Leu Leu Gly Ala Ser
225                 230                 235                 240

Asp Thr His Phe Gln Asp Leu Lys Met His Val Thr Leu Ala Tyr Asn
                245                 250                 255

Ile Phe Thr Asn Thr Val His Glu Arg Met Pro Arg Cys Arg Phe Gly
                260                 265                 270
```

```
Phe Phe Gln Ile Val Asn Asn Phe Tyr Asp Arg Trp Asp Lys Tyr Ala
        275                 280                 285

Ile Gly Gly Ser Ser Asn Pro Thr Ile Leu Ser Gln Gly Asn Lys Phe
        290                 295                 300

Val Ala Pro Asp Phe Ile Tyr Lys Lys Asn Val Cys Leu Arg Thr Gly
305                 310                 315                 320

Ala Gln Glu Pro Glu Trp Met Thr Trp Asn Trp Arg Thr Gln Asn Asp
                325                 330                 335

Val Leu Glu Asn Gly Ala Ile Phe Val Ala Ser Gly Ser Asp Pro Val
        340                 345                 350

Leu Thr Ala Glu Gln Asn Ala Gly Met Met Gln Ala Glu Pro Gly Asp
        355                 360                 365

Met Val Pro Gln Leu Thr Met Asn Ala Gly Val Leu Thr Cys Ser Pro
370                 375                 380

Gly Ala Pro Cys
385
```

(2) INFORMATION FOR SEQ ID NO:81:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:81:

```
Ala Pro Asp Gln Leu Leu Ser Thr Tyr Asn Asp His
1               5                   10
```

(2) INFORMATION FOR SEQ ID NO:82:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:82:

```
Tyr Phe Phe Leu Phe Tyr Phe
1               5
```

(2) INFORMATION FOR SEQ ID NO:83:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:83:

```
Tyr Phe Ile Cys Thr Lys Val Met Glu Met Asn Leu Tyr
1               5                   10

Leu Leu Val Leu
        15
```

(2) INFORMATION FOR SEQ ID NO:84:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:84:

Lys Lys Lys Lys Pro Asn
1               5

(2) INFORMATION FOR SEQ ID NO:85:

(i) SEQUENCE CHARACTERISTICS:
            (A) LENGTH: 42 amino acids
            (B) TYPE: amino acid
            (D) TOPOLOGY: linear (ii) MOLECULE TYPE: protein (xi) SEQUENCE DESCRIPTION: SEQ ID NO:85:

Ala Pro Gly Gln Phe Leu Ser Phe Tyr Asn Asn His Lys Tyr Leu Phe Tyr
1               5                   10                  15

Phe Ile Phe Asp Ile Leu Tyr Glu Pro Leu Arg Ser Ser Thr Leu Leu
            20                  25                  30

Thr Cys Phe Lys Phe Ile Arg Val Tyr
        35                  40

(2) INFORMATION FOR SEQ ID NO:86:

(i) SEQUENCE CHARACTERISTICS:
            (A) LENGTH: 17 amino acids
            (B) TYPE: amino acid
            (D) TOPOLOGY: linear (ii) MOLECULE TYPE: protein (xi) SEQUENCE DESCRIPTION: SEQ ID NO:86:

Tyr Phe Ile Cys Thr Lys Val Met Glu Met Asn Leu Tyr
1               5                   10

Leu Leu Ser Thr
            15

(2) INFORMATION FOR SEQ ID NO:87:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO:87:

Ala Pro Cys Gln Phe Ser
1               5

(2) INFORMATION FOR SEQ ID NO:88:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:88:

Ala Phe Ala Met Ile Lys Asn Thr Phe Leu Phe Tyr Phe
1               5                   10

(2) INFORMATION FOR SEQ ID NO:89:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:89:

```
Tyr Phe Ile Cys Thr Gly Asn Glu Pro Leu Pro Ser Ser
1               5                   10

Thr Leu
    15
```

(2) INFORMATION FOR SEQ ID NO:90:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:90:

```
Ala Pro Gly Gln Phe Leu Cys Asn Asp His Lys Tyr Leu Leu Thr Ile Ser Val
1               5                   10                  15

His Leu Ile Arg Phe Gly His Glu
    20                  25
```

(2) INFORMATION FOR SEQ ID NO:91:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:91:

```
Cys Asn Arg Phe Val
1               5
```

(2) INFORMATION FOR SEQ ID NO:92:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:92:

```
Ile Met Ile Cys Phe Asp Ser Gln Phe His Asn Met Ala Ser
1               5                   10
```

(2) INFORMATION FOR SEQ ID NO:93:

(i) SEQUENCE CHARACTERISTICS:
        (A) LENGTH: 14 amino acids
        (B) TYPE: amino acid
        (D) TOPOLOGY: linear (ii) MOLECULE TYPE: protein -continued (xi) SEQUENCE DESCRIPTION: SEQ ID NO:93:

```
Arg Arg Val Ser Leu Ile Asn Tyr Ile Leu Trp Phe Leu Tyr
1               5                   10
```

What is claimed is:

1. An isolated peptide selected from the group consisting of a peptide comprising an epitope-containing portion of the amino acid sequence of a ragweed pollen allergen *Amb a* IA SEQ ID NO:72, a peptide comprising an epitope-containing portion of the amino acid sequence of a ragweed pollen allergen *Amb a* IB SEQ ID NO:74, a peptide comprising an epitope-containing portion of the amino acid sequence of a ragweed pollen allergen *Amb a* IC SEQ ID NO:76, and a peptide comprising an epitope-containing portion of the amino acid sequence of a ragweed pollen allergen *Amb a* ID SEQ ID NO:78, provided that the peptide does not comprise the full-length amino acid sequence of *Amb a* IA, *Amb a* IB, *Amb a* IC, or *Amb a* ID, the peptide stimulates T cells specific for a ragweed pollen allergen, and the epitope-containing portion of the peptide is recognized by a T cell receptor specific for a ragweed pollen allergen.

2. An isolated peptide which stimulates T cells specific for a ragweed pollen allergen, wherein the ragweed pollen allergen comprises an amino acid sequence selected from the group consisting of SEQ ID NO:72, SEQ ID NO:74:, SEQ ID NO:76, and SEQ ID NO:78, provided that the peptide does not comprise the full length amino acid sequence of SEQ ID NO:72, SEQ ID NO:74, SEQ ID NO:76, or SEQ ID NO:78.

3. An isolated peptide having at least one T cell epitope recognized by a T cell receptor specific for a ragweed pollen allergen, wherein the ragweed pollen allergen comprises an amino acid sequence selected from the group consisting of SEQ ID NO:72, SEQ ID NO:74, SEQ ID NO:76, and SEQ ID NO:78, provided that the peptide does not comprise the full length amino acid sequence of SEQ ID NO:72, SEQ ID NO:74, SEQ ID NO:76, or SEQ ID NO:78.

4. An isolated peptide which stimulates T cells specific for a ragweed pollen allergen, wherein the ragweed pollen allergen comprises an amino acid sequence selected from the group consisting of SEQ ID NO:72, SEQ ID NO:74:, SEQ ID NO:76, and SEQ ID NO:78, provided that the peptide does not comprise the full length amino acid sequence of SEQ ID NO:72, SEQ ID NO:74, SEQ ID NO:76, or SEQ ID NO:78.

5. The isolated peptide of claim 1, 2, 3, or 4, comprising a portion of the amino acid sequence of *Amb a* IA SEQ ID NO:72.

6. The isolated peptide of claim 1, 2, 3, or 4, comprising a portion of the amino acid sequence of *Amb a* IB SEQ ID NO:74.

7. The isolated peptide of claim 1, 2, 3, or 4, comprising a portion of the amino acid sequence of *Amb a* IC SEQ ID NO:76.

8. The isolated peptide of claim 1, 2, 3, or 4, comprising a portion of the amino acid sequence of *Amb a* ID SEQ ID NO:78.

9. The isolated peptide of claim 1, 2, 3, or 4, wherein the ragweed pollen allergen comprises the amino acid sequence of SEQ ID NO:72.

10. The isolated peptide of claim 1, 2, 3, or 4, wherein the ragweed pollen allergen comprises the amino acid sequence of SEQ ID NO:74.

11. The isolated peptide of claim 1, 2, 3, or 4, wherein the ragweed pollen allergen comprises the amino acid sequence of SEQ ID NO:76.

12. The isolated peptide of claim 1, 2, 3, or 4, wherein the ragweed pollen allergen comprises the amino acid sequence of SEQ ID NO:78.

13. A composition comprising at least one peptide of claim 1, 2, 3, or 4 and a carrier.

14. A composition comprising at least two peptides of claim 1, 2, 3, or 4.

15. A composition comprising at least two peptides of claim 1, 2, 3, or 4 and a pharmaceutically acceptable carrier.

* * * * *